United States Patent [19]

Terada et al.

[11] Patent Number: 4,847,272
[45] Date of Patent: Jul. 11, 1989

[54] THIANAPHTHENE DERIVATIVES

[75] Inventors: Atsusuke Terada; Yoshiya Amemiya; Keiichi Matsuda; Takeshi Oshima, all of Tokyo, Japan

[73] Assignee: Sankyo Company Limited, Tokyo, Japan

[21] Appl. No.: 7,375

[22] Filed: Jan. 27, 1987

[30] Foreign Application Priority Data

Jan. 28, 1986 [JP] Japan .................................. 61-16501
Sep. 27, 1986 [JP] Japan .................................. 61-228769

[51] Int. Cl.⁴ .................. C07D 409/06; A61K 31/415
[52] U.S. Cl. .................................... 514/337; 514/397; 546/274; 548/336
[58] Field of Search ................. 514/337, 397; 546/274; 548/336

[56] References Cited

U.S. PATENT DOCUMENTS 4,410,539 10/1983 Cross et al. ......................... 546/274
4,496,572 1/1985 Cross et al. ......................... 546/274
4,611,059 9/1986 Sih ....................................... 546/274

Primary Examiner—Jane T. Fan
Attorney, Agent, or Firm—Frishauf, Holtz, Goodman & Woodward

[57] ABSTRACT

Compounds of formula (I):

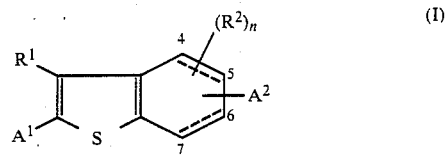

(wherein n is 0 or 1, $R^1$ and $R^2$ are hydrogen or alkyl, one of $A^1$ and $A^2$ is —Z—Y and the other is —W—COOH, where W and Z are alkenylene or alkylene and Y is imidazolyl or pyridyl, and the broken lines represent two single bonds or one single bond and one double bond) and their salts, esters and amides have the ability to inhibit the synthesis of thromboxane $A_2$ and hence are useful in the treatment or prophylaxis of thrombotic conditions. They may be prepared by introducing an imidazolyl or pyridyl group into the corresponding compound in which Y is replaced by an active group or atom.

44 Claims, No Drawings

THIANAPHTHENE DERIVATIVES

BACKGROUND TO THE INVENTION

The present invention relates to a series of thianaphthene derivatives which have been found to have certain valuable therapeutic activities. The invention also provides processes for preparing these compounds and methods of using them.

The compounds of the invention have the ability to inhibit blood platelet aggregation and to inhibit the biosynthesis of thromboxane $A_2$ (hereinafter referred to, as is conventional, as "$TXA_2$").

The compounds of the present invention may be regarded as derivatives of thianaphthene ["The Merck Index", Tenth Edition (1983) monograph 9142], which has the formula (A):

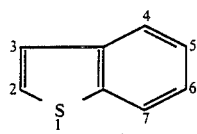

In accordance with the recommendations of the International Union of Pure and Applied Chemistry, Commission on Nomenclature of Organic Chemistry, the compounds of the present invention are named semi-systematically, taking thianaphthene as the parent compound. For the avoidance of doubt, the numbering system employed herein is that shown on the above formula (A).

$TXA_2$ plays an important role in inducing blood platelet aggregation, and inhibiting its biosynthesis is believed to reduce the extent of blood platelet aggregation, apart from any direct effect the compounds may have on such aggregation. It is known that $TXA_2$ is produced from prostaglandin endoperoxide $PGH_2$ via $PGG_2$. It is known that the activity of $TXA_2$ is generally opposite to that of $PGI_2$, which causes vasodilation and prevents platelet aggregation. Accordingly, it has been suggested that the balance within the blood between $TXA_2$ and $PGI_2$ is a controlling factor in the development and/or cure of thrombosis. Accordingly, it is desirable for the treatment or prophylaxis of thromboembolisms to inhibit selectively the biosynthesis of $TXA_2$ and thereby to enhance the activity of $PGI_2$ (which has an inhibitory effect on platelet aggregation) and also to increase the level of $PGI_2$ as a result of accumulation of $PGH_2$. It is believed that an effective inhibitor of the biosynthesis of $TXA_2$ would be of considerable value in the treatment or prophylaxis of a variety of diseases and disorders associated with the circulatory system. It is, however, important that this inhibitory activity should not be accompanied by inhibition of the enzymes responsible for the synthesis of other prostaglandins.

Various compounds have been proposed for such use. A proposal has been made to use certain thianaphthene derivatives for this purpose and those compounds disclosed in European Patent Specification No. 73663B1 and the corresponding U.S. Pat. No. 4,496,572 do exhibit the necessary activity.

We have now discovered that certain thianaphthenes in which the 6-membered ring is partially saturated have an outstanding ability to inhibit $TXA_2$ synthesis which is an order of magnitude or more better than that of known compounds which are currently available for this purpose. Although superficially similar to the compounds of the invention, the compounds of EP 73663B1 have a fully unsaturated and aromatized thianaphthene ring system. On the contrary, the compounds of the invention have a partially saturated 6-membered ring. The aromaticity of the prior compounds leads to a rigidity of molecular structure and configuration and a fluidity of electron flow which are not possessed by the compounds of the present invention and which would be expected to have a major influence on the biological properties of the compounds. It is, therefore, surprising that the compounds of the invention possess biological properties similar in nature to those of the prior compounds, especially since the activity concerned relates to the inhibition of enzymes, where it would be expected that the difference between the prior compounds and the compounds of the invention would have a substantial influence.

BRIEF SUMMARY OF INVENTION

The compounds of the present invention are those compounds of formula (I):

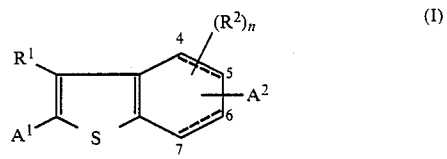

in which:

$R^1$ and $R^2$ are independently selected from the group consisting of hydrogen atoms, $C_1$–$C_4$ alkyl groups, $C_6$–$C_{10}$ carbocyclic aryl groups and substituted $C_6$–$C_{10}$ carbocyclic aryl groups having at least one subtituent selected from the group consisting of substituents (a);

n is 1 or 2;

one of $A^1$ and $A^2$ represents a group of formula —Z—Y in which Y represents an imidazolyl or pyridyl group and Z represents a methylene, ethylene, trimethylene or vinylene group or a methylene, ethylene, trimethylene or vinylene group having at least one substituent selected from the group consisting of substituents (b);

the other of $A^1$ and $A^2$ represents a group of formula —W—COOH, where W represents a direct bond, a methylene group, a methine group (i.e. a group of formula =CH— attached by its double bond to the thianaphthene system), an ethylene group, a vinylene group or a substituted methylene, methine, ethylene or vinylene group having at least one substituent selected from the group consisting of substituents (c), provided that W only represents said methine group when $A^1$ represents said group of formula —Z—Y;

$A^2$ is at the 5- or 6-position on the thianaphthene system;

each broken line represents a single or double carbon-carbon bond between the 4 and 5 or the 6 and 7 positions, provided that, when $A^2$ is at the 5-position, there is a single bond between the 6 and 7 positions, and that, when $A^2$ is at the 6-position, there is a single bond between the 4 and 5 positions;

substituents (a): $C_1$–$C_4$ alkyl groups, $C_1$–$C_4$ alkoxy groups, $C_2$–$C_6$ aliphatic carboxylic acyloxy groups, aromatic carboxylic acyloxy groups, $C_2$–$C_5$ aliphatic carboxylic acylamino groups, aromatic carboxylic acylamino groups, trifluoromethyl groups, halogen atoms, nitro groups, cyano groups, amino groups, $C_1$–$C_4$ alkylamino groups, dialkylamino groups in which each alkyl part is $C_1$–$C_4$, carboxy groups and esters and amides of said carboxy groups, the aromatic parts of said aromatic acyloxy and aromatic acylamino groups being $C_6$–$C_{10}$ carbocyclic aryl groups which are unsubstituted or have at least one substituent selected from the group consisting of $C_1$–$C_4$ alkyl groups, $C_1$–$C_4$ alkoxy groups and halogen atoms;

substituents (b): $C_1$–$C_4$ alkyl groups, $C_3$–$C_6$ cycloalkyl groups, $C_6$–$C_{10}$ aryl groups, substituted $C_6$–$C_{10}$ aryl groups having at least one substituent selected from the group consisting of substituents (a) and heterocyclic groups having from 5 to 10 ring atoms, of which from 1 to 3 are hetero-atoms selected from the group consisting of nitrogen, oxygen and sulfur heteroatoms, said heterocyclic groups being unsubstituted or having at least one substituent selected from the group consisting of substituents (a), substituents (c) and oxygen atoms; and substituents (c): $C_1$–$C_4$ alkyl groups, $C_6$–$C_{10}$ aryl groups and substituted $C_6$–$C_{10}$ aryl groups having at least one substituent selected from the group consisting of substituents (a);

and pharmaceutically acceptable salts, amides and esters thereof.

The invention further provides a pharmaceutical composition comprising an inhibitor of $TXA_2$ biosynthesis in admixture with a pharmaceutically acceptable carrier or diluent, wherein said inhibitor is selected from the group consisting of compounds of formula (I) and pharmaceutically acceptable esters, amides and salts thereof.

The invention still further provides a method for the treatment or prophylaxis of diseases and disorders arising from an imbalance in the level of $TXA_2$ in an animal, normally mammal, including human being, which comprises administering to said animal an effective amount of an inhibitor of the biosynthesis of $TXA_2$, wherein said inhibitor is selected from the group consisting of compounds of formula (I) and pharmaceutically acceptable esters, amides and salts thereof.

The invention also provides methods of preparing the compounds of formula (I) and their esters, amides and salts, as described in more detail hereafter.

DETAILED DESCRIPTION OF INVENTION

In more detail, the compounds of the invention may be represented by the two formulae ($I^i$) and ($I^{ii}$):

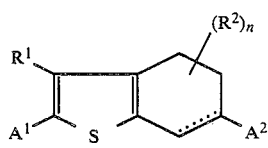

(I$^i$)

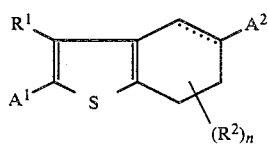

(I$^{ii}$)

(in which $R^1$, $R^2$, $A^1$, $A^2$ and n are as defined above and the dotted line means a single or double carbon-carbon bond) and, more specifically, the compounds may be represented by the formula ($I^{iii}$), ($I^{iv}$) and ($I^v$):

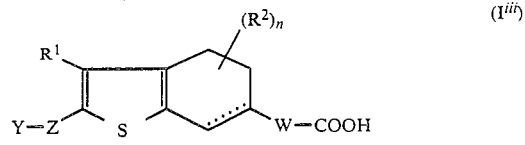

(I$^{iii}$)

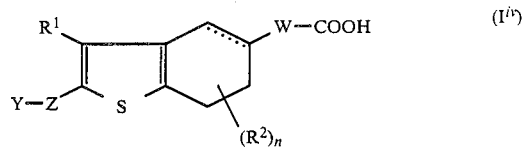

(I$^{iv}$)

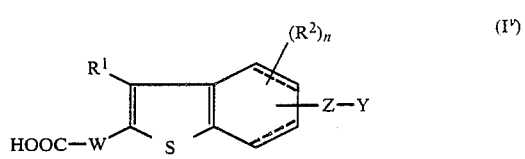

(I$^v$)

(in which $R^1$, $R^2$, W, Y, Z, n and the dotted and broken lines are as defined above).

In the compounds of the invention, where $R^1$, $R^2$, substituent (a), the substituent on substituted aromatic acyloxy or acylamino groups, substituent (b) or substituent (c) is a $C_1$–$C_4$ alkyl group, this may be a straight or branched chain group and examples include the methyl, ethyl, propyl, isopropyl, butyl, isobutyl, sec-butyl and t-butyl groups.

Where $R^1$, $R^2$, substituent (b) or substituent (c) represents an aryl group, this is a carbocyclic aryl group having from 6 to 10, preferably 6 or 10, ring carbon atoms and may be unsubstituted or substituted with at least one of the substituents defined above as substituents (a). Examples of such groups include the phenyl, 1-naphthyl and 2-naphthyl groups and such groups having at least one of substituents (a), for example the o-tolyl, m-tolyl, p-tolyl, o-methoxyphenyl, m-methoxyphenyl, p-methoxyphenyl, o-chlorophenyl, m-chlorophenyl, p-chlorophenyl, o-fluorophenyl, m-fluorophenyl, p-fluorophenyl, o-nitrophenyl, m-nitrophenyl, p-nitrophenyl, o-cyanophenyl, m-cyanophenyl, p-cyanophenyl, 2,4-dichlorophenyl, 3,5-dichlorophenyl, 2,4-dimethoxyphenyl, 2,4,6-trimethoxyphenyl, 3,5-dimethoxyphenyl, 2,4-dimethylphenyl, 2,4,6-trimethylphenyl, 2-methoxy-4-methylphenyl, o-acetoxyphenyl, p-benzoyloxyphenyl, p-(p-toluoyloxy)-phenyl, p-acetamidophenyl, p-benzamidophenyl, p-trifluoromethylphenyl, 3-methyl-1-naphthyl and 7-methyl-1-naphthyl groups.

Where substituent (a) or the substituent on aromatic acyloxy or acylamino groups is a $C_1$–$C_4$ alkoxy group, this is more preferably a $C_1$–$C_3$ group and may be a straight or branched chain group. Examples include the methoxy, ethoxy, propoxy, isopropoxy, butoxy and t-butoxy groups.

Where substituent (a) represents a $C_2$–$C_5$ aliphatic carboxylic acyloxy group, this may be a straight or branched chain group and is preferably an alkanoyloxy or alkenoyloxy, more preferably alkanoyloxy, group. Examples include the acetoxy, propionyloxy, butyryloxy, isobutyryloxy, valeryloxy, isovaleryloxy and pivaloyloxy groups.

Where substituent (a) represents a carbocyclic aromatic carboxylic acyloxy group, the aromatic part may be as defined above in relation to the substituted and unsubstituted $C_6$–$C_{10}$ aryl groups, the acyloxy group being an arylcarbonyloxy group. Preferred such groups include the benzoyloxy, o-toluoyloxy, m-toluoyloxy, p-toluoyloxy, o-anisoyloxy, m-anisoyloxy, p-anisoyloxy, o-chlorobenzoyloxy, m-chlorobenzoyloxy and p-chlorobenzoyloxy groups.

Where substituent (a) represents an aliphatic acylamino group, this may be a straight or branched chain group having from 2 to 5 carbon atoms and is preferably an alkanoylamino or alkenoylamino, more preferably alkanoylamino, group. Examples include the acetamido, propionylamino, butyrylamino, isobutyrylamino, valeramido, isovaleramido and pivaloylamino groups.

Where substituent (a) represents a carbocyclic aromatic carboxylic acylamino group, the aromatic part may be as exemplified above in relation to the unsubstituted and substituted $C_6$–$C_{10}$ aryl groups, the group being an arylcarbonylamino group. Examples of such groups include the benzamido, o-toluoylamino, n-toluoylamino, p-toluoylamino, o-anisoylamino, m-anisoylamino, p-anisoylamino, o-chlorobenzamido, m-chlorobenzamido and p-chlorobenzamido groups.

Where substituent (a) represents a halogen atom, this is preferably a fluorine, chlorine or bromine atom.

Where substituent (a) is an alkylamino or dialkylamino group, the or each alkyl part is a $C_1$–$C_4$ alkyl group and examples include the methylamino, ethylamino, propylamino, butylamino, dimethylamino and diethylamino groups.

Where substituent (a) represents an ester or amide of a carboxy group, this may be as described in more detail hereafter in relation to such esters and amides.

In the case of substituents (a) and the substituents on aromatic acyloxy and acylamino groups, there is no particular limitation in principle to the number of such substituents, the only constraints being the number of substitutable positions and possibly steric constraints. Hence, where the group to be substituted is a phenyl group, provided steric hindrance is not a problem, the maximum number of substituents is five. Where the group to be substituted is a naphthyl group, again provided steric hindrance is not a problem, the maximum number of substituents is seven. However, more commonly, the number of such substituents will be from 1 to 3.

Where substituent (b) represents a cycloalkyl group, this has from 3 to 6 ring atoms and may be a cyclopropyl, cyclobutyl, cyclopentyl or cyclohexyl group.

Where substituent (b) represents a heterocyclic group, this may be a monocyclic or bicyclic heterocyclic group having from 5 to 10, more preferably 5 or 6, ring atoms, of which at least one, and preferably from 1 to 3, are hetero-atoms selected from the group consisting of nitrogen, oxygen and sulfur hetero-atoms. The heterocyclic ring is preferably, although not necessarily, aromatic in character and it may be unsubstituted or have at least one substituent selected from the group consisting of substituents (a), substituents (b) and oxygen atoms. Examples of such groups include the furyl, thienyl, imidazolyl, thiazolyl, oxazolyl, isoxazolyl, pyridyl, quinolyl, isoquinolyl and indolyl groups, which may be unsubstituted or substituted as defined above.

Y represents an imidazolyl or pyridyl group, preferably the 1-imidazolyl group or the 3-pyridyl group.

Z represents the aforementioned methylene, ethylene, trimethylene or vinylene group, any of which may be unsubstituted or may have at least one substituent selected from the group consisting of substituents (b), as exemplified above.

W may represent a direct bond between the carboxy group and the hydrogenated thianaphthene ring or it may represent a methylene, methine, ethylene or vinylene group, any of which may be unsubstituted or may have at least one substituent selected from the group consisting of substituents (c), e.g. as exemplified above. Self-evidently, W cannot represent a methine group (i.e. a group =CH— joined by the double bond to the hydrogenated thianaphthene system) either when $A^1$ represents said group of formula —W—COOH or when $A^2$ represents said group of formula —W—COOH and is attached to a carbon atom which already forms part of a ring double bond. In other words, W can only represent a methine group when $A^2$ represents said group of formula —W—COOH and both broken lines in formula (I) represent single bonds.

The substituent or substituents represented by $R^2$ may be present at any of the 4, 5, 6 and 7 positions, provided that (in the case of the 5 and 6 positions) these are not already occupied by the group represented by $A^2$.

Preferred classes of compounds of the present invention are as follows:

1. Compounds of formula (I), ($I^{iii}$), ($I^{iv}$) and ($I^v$), defined above, in which:

$A^1$, $A^2$, Y and the broken and dotted lines are as defined above;

$R^1$ and $R^2$ are independently selected from the group consisting of hydrogen atoms and $C_1$–$C_4$ alkyl groups;

n is 1;

Z represents a methylene, ethylene, trimethylene or vinylene group or a methylene, ethylene, trimethylene or vinylene group having at least one substituent selected from the group consisting of substituents (b');

W represents a direct bond or a methylene, methine, ethylene or vinylene group; and substituents (b')

$C_1$–$C_4$ alkyl groups, cyclohexyl groups, phenyl groups and substituted phenyl groups having at least one substituent selected from the group consisting of $C_1$–$C_4$ alkyl groups, $C_1$–$C_4$ alkoxy groups and halogen atoms.

2. Compounds of formula ($I^{iii}$), defined above, in which:

Y and the dotted line are as defined above;

$R^1$ and $R^2$ are independently selected from the group consisting of hydrogen atoms and $C_1$–$C_4$ alkyl groups;

n is 1;

Z represents a methylene, ethylene, trimethylene or vinylene group or a methylene, ethylene, trimethylene or vinylene group having at least one substituent selected from the group consisting of substituents (b'), defined above; and W represents a direct bond or a methylene, methine, ethylene or vinylene group.

3. Compounds of formula ($I^{iii}$), defined above, in which:

Y and the dotted line are as defined above;

$R^1$ and $R^2$ are independently selected from the group consisting of hydrogen atoms, methyl groups and ethyl groups;

n is 1;

Z represents a methylene or ethylene group or a methylene or ethylene group having at least one substituent selected from the group consisting of substituents (b″);

W represents a direct bond; and substituents (b″)

methyl groups, ethyl groups, phenyl groups and substituted phenyl groups having at least one substituent selected from the group consisting of methyl groups, ethyl groups, methoxy groups, ethoxy groups and halogen atoms.

4. Compounds of formula ($I^{iv}$), defined above, in which:

Y and the dotted line are as defined above;

$R^1$ and $R^2$ are independently selected from the group consisting of hydrogen atoms and $C_1$-$C_4$ alkyl groups;

n is 1;

Z represents a methylene, ethylene, trimethylene or vinylene group or a methylene, ethylene, trimethylene or vinylene group having at least one substituent selected from the group consisting of substituents (b′), defined above; and W represents a direct bond or a methylene, methine, ethylene or vinylene group.

5. Compounds of formula ($I^{iv}$), defined above, in which:

Y and the dotted line are as defined above;

$R^1$ and $R^2$ are independently selected from the group consisting of hydrogen atoms, methyl groups and ethyl groups;

n is 1;

Z represents a methylene or ethylene group or a methylene or ethylene group having at least one substituent selected from the group consisting of substituents (b″), defined above; and W represents a direct bond.

6. Compounds of formula ($I^{vi}$):

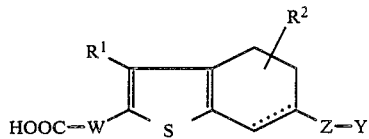

in which:

Y and the dotted line are as defined above;

$R^1$ and $R^2$ are independently selected from the group consisting of hydrogen atoms and $C_1$-$C_4$ alkyl groups;

Z represents a methylene, ethylene, trimethylene or vinylene group or a methylene, ethylene, trimethylene or vinylene group having at least one substituent selected from the group consisting of substituents (b′), defined above; and W represents a direct bond or a methylene, methine, ethylene or vinylene group.

7. Compounds of formula ($I^{vi}$), defined above, in which:

Y and the dotted line are as defined above;

$R^1$ and $R^2$ are independently selected from the group consisting of hydrogen atoms, methyl groups and ethyl groups;

Z represents a methylene group; and

W represents a direct bond.

8. Compounds of formula ($I^{vii}$):

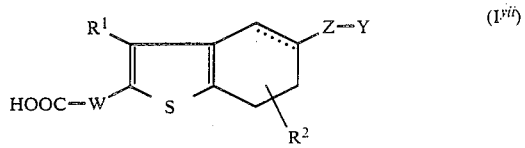

in which:

Y and the dotted line are as defined above;

$R^1$ and $R^2$ are independently selected from the group consisting of hydrogen atoms and $C_1$-$C_4$ alkyl groups;

Z represents a methylene, ethylene, trimethylene or vinylene group or a methylene, ethylene, trimethylene or vinylene group having at least one substituent selected from the group consisting of substituents (b′), defined above; and W represents a direct bond or a methylene, methine, ethylene or vinylene group.

9. Compounds of formula ($I^{vii}$), defined above, in which:

Y and the dotted line are as defined above;

$R^1$ and $R^2$ are independently selected from the group consisting of hydrogen atoms, methyl groups and ethyl groups;

Z represents a methylene group; and

W represents a direct bond.

The compounds of the invention necessarily contain at least one carboxy group in the group of formula —W—COOH, which may be at any of the 2, 5 and 6 positions. Where substituent (a) also represents a carboxy group, then the compounds may contain one or more additional carboxy groups. Such carboxy groups may, independently of each other, form esters, amides and salts and, where such esters, amides or salts are formed and where there are two or more carboxy groups in the compound, the groups may be the same or different.

Where the carboxy group is esterified, the nature of the resulting ester is not critical to the present invention. In principle, the compounds of the invention, being carboxylic acids, will form esters with any ester-forming alcohol and all such esters form part of the present invention. However, where the esters are to be employed for therapeutic purposes, it is, of course, necessary that the resulting esters should be pharmaceutically acceptable, which, as is understood in the art, means that the esters should not have reduced activity (or unacceptably reduced activity) and should not have increased toxicity (or unacceptably increased toxicity) as compared with the free acid. However, where the ester is to be employed for other purposes, for example as an intermediate in the preparation of other compounds, even this criterion does not apply.

Examples of such esters include: $C_1$-$C_6$, more preferably $C_1$-$C_4$, alkyl esters, for example the methyl, ethyl, propyl, isopropyl, butyl, isobutyl, sec-butyl, t-butyl, pentyl and hexyl esters; aralkyl and diarylalkyl esters, such as the benzyl, p-nitrobenzyl and benzhydryl esters; alkoxycarbonylalkyl esters, in which the alkoxy and alkyl parts are both $C_1$-$C_4$, especially alkoxycarbonylmethyl esters, such as the ethoxycarbonylmethyl and t-butoxycarbonylmethyl esters; alkoxycarbonyloxyalkyl esters in which the alkoxy and alkyl parts are both $C_1$-$C_4$, especially 2-(alkoxycarbonyloxy)ethyl esters, such as the 2-methoxycarbonyloxyethyl, 2-ethoxycarbonyloxyethyl and 2-t-butoxycarbonyloxyethyl esters;

and other specific esters, such as the phthalidyl, substituted phthalidyl, phenacyl, substituted phenacyl (e.g. p-nitrophenacyl) and (5-methyl-2-oxo-1,3-dioxolen-4-yl)methyl esters.

Likewise, where one or more of the carboxy groups has formed an amide, the precise nature of the amide is not critical, provided that, where the amide is to be used for therapeutic purposes, the resulting amide is pharmaceutically acceptable. Accordingly, one or more of these carboxy groups can be replaced by a carbamoyl group or a substituted carbamoyl group, preferably an alkylcarbamoyl or dialkylcarbamoyl group in which the or each alkyl group is a $C_1$–$C_4$ alkyl group (e.g. as defined above in relation to $R^1$ and $R^2$), for example a methylcarbamoyl, ethylcarbamoyl, dimethylcarbamoyl or diethylcarbamoyl group.

One or more of these carboxy groups may also form salts with appropriate bases. Additionally, since the imidazolyl and pyridyl nitrogen atoms (in the group represented by Y) are basic in character, the compounds of the invention also form acid addition salts. The nature of such salts is likewise not critical, provided that, where they are to be used for therapeutic purposes, the salts are pharmaceutically acceptable. A wide range of acids can form acid addition salts with the compounds of the invention and examples of such acids include: mineral acids, such as hydrochloric acid, hydrobromic acid, nitric acid and phosphoric acid; organic carboxylic acids, such as acetic acid, trifluoroacetic acid, asparaginic acid, glutamic acid, oxalic acid, tartaric acid, citric acid, maleic acid, fumaric acid, lactic acid, salicylic acid, malonic acid and succinic acid; and organic sulfonic acids, such as methanesulfonic acid, benzenesulfonic acid and p-toluenesulfonic acid.

Examples of salts with bases include: salts with metals, especially alkali metals and alkaline earth metals, such as the lithium, sodium, potassium, calcium and magnesium salts; the ammonium salt; salts with organic amines, such as cyclohexylamine, diisopropylamine or triethylamine; and salts with basic amino acids, such as lysine or arginine.

The compounds of the invention may contain several asymmetric carbon atoms and, accordingly, optical isomers of the compounds are possible. Although the various optical isomers are all represented herein by a single formula, the present invention embraces both the individual isolated isomers and mixtures thereof.

Examples of specific compounds of the invention are given in the following formulae (I-1) to (I-8), in which the substituents are as defined in the corresponding one of Tables 1 to 8 [i.e. Table 1 relates to formula (I-1), Table 2 relates to formula (I-2) and so on]. The compounds of the invention are hereinafter, where appropriate, identified by the numbers appended to them in these Tables. In the Tables, the following abbreviations are used:

| Bz  | benzyl       |
|-----|--------------|
| Et  | ethyl        |
| cHx | cyclohexyl   |
| Imid | 1-imidazolyl |
| Me  | methyl       |
| Np  | 1-naphthyl   |
| Pen | 1-propenyl   |
| Ph  | phenyl       |
| Pr  | propyl       |
| iPr | isopropyl    |
| Pyr | 3-pyridyl    |
| Sty | styryl       |

| Vin | vinyl |
|-----|-------|

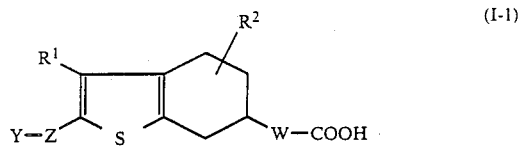

(I-1)

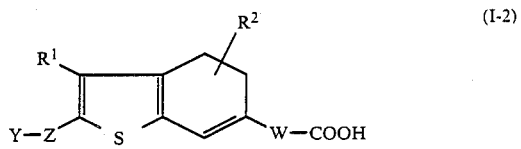

(I-2)

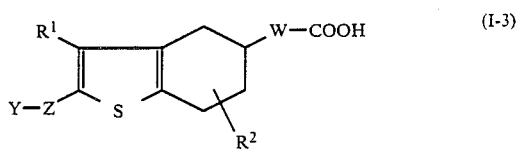

(I-3)

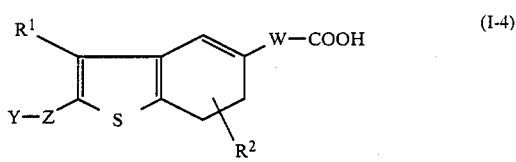

(I-4)

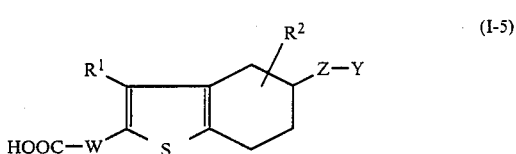

(I-5)

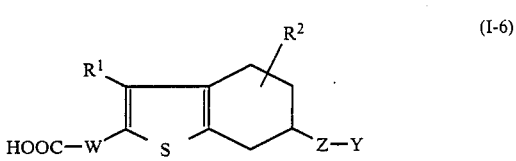

(I-6)

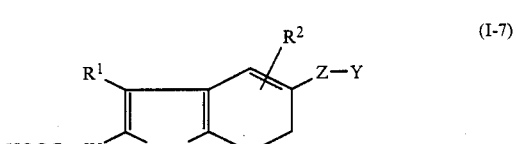

(I-7)

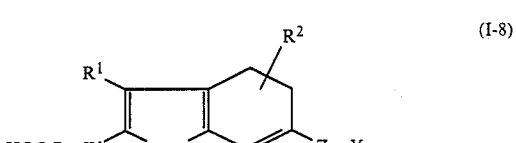

(I-8)

TABLE 1

| No. | Y—Z | $R^1$ | $R^2$ | W |
|-----|-----|-------|-------|---|
| 1-1 | ImidMe | H | H | Direct bond |
| 1-2 | ImidMe | H | H | —CH₂— |
| 1-3 | ImidMe | H | H | =CH— |
| 1-4 | ImidMe | H | H | —CH₂—CH₂— |
| 1-5 | ImidMe | H | H | —CH=CH— |
| 1-6 | ImidMe | Me | H | Direct Bond |
| 1-7 | ImidMe | Me | H | —CH₂— |
| 1-8 | ImidMe | Me | H | =CH— |
| 1-9 | ImidMe | Me | H | —CH₂—CH₂— |
| 1-10 | ImidMe | Me | H | —CH=CH— |

TABLE 1-continued

| No. | Y—Z | R¹ | R² | W |
|---|---|---|---|---|
| 1-11 | ImidMe | H | 4-Me | Direct bond |
| 1-12 | ImidMe | H | 4-Me | —CH₂— |
| 1-13 | ImidMe | H | 4-Me | =CH— |
| 1-14 | ImidMe | H | 4-Me | —CH=CH— |
| 1-15 | ImidMe | H | 4-Me | —CH₂—CH₂— |
| 1-16 | ImidMe | CH₃ | 4-Me | Direct bond |
| 1-17 | 1-ImidEt | H | H | Direct bond |
| 1-18 | 1-ImidEt | H | H | —CH₂— |
| 1-19 | 1-ImidEt | H | H | =CH— |
| 1-20 | 1-ImidPr | H | H | Direct bond |
| 1-21 | α-ImidBz | H | H | Direct bond |
| 1-22 | 2,4-diCl—α-ImidBz | H | H | Direct bond |
| 1-23 | 2-F—α-ImidBz | H | H | Direct bond |
| 1-24 | 2-MeO—α-ImidBz | H | H | Direct bond |
| 1-25 | 2,4-diMeO—α-ImidBz | H | H | Direct bond |
| 1-26 | 2,4,6-triMeO—α-ImidBz | H | H | Direct bond |
| 1-27 | 2-Me—α-ImidBz | H | H | Direct bond |
| 1-28 | 2-MeO—4-Me—α-ImidBz | H | H | Direct bond |
| 1-29 | 2,4,6-triMe—α-ImidBz | H | H | Direct bond |
| 1-30 | Np—CH(Imid)— | H | H | Direct bond |
| 1-31 | 4-F—α-ImidBz | H | H | Direct bond |
| 1-32 | 4-MeO—α-ImidBz | H | H | Direct bond |
| 1-33 | 2-Me—1-ImidPr | H | H | Direct bond |
| 1-34 | 2,2-diMe—1-ImidPr | H | H | Direct bond |
| 1-35 | Imid—CH(cHx)— | H | H | Direct bond |
| 1-36 | 2-ImidEt | H | H | Direct bond |
| 1-37 | 2-ImidEt | H | H | —CH₂— |
| 1-38 | 2-ImidEt | H | H | =CH— |
| 1-39 | 1-Me—2-ImidEt | H | H | Direct bond |
| 1-40 | 2-ImidPr | H | H | Direct bond |
| 1-41 | 1-iPr—2-ImidEt | H | H | Direct bond |
| 1-42 | 2-iPr—2-ImidEt | H | H | Direct bond |
| 1-43 | 1-Ph—2-ImidEt | H | H | Direct bond |
| 1-44 | 2-Ph—2-ImidEt | H | H | Direct bond |
| 1-45 | 2-ImidVin | H | H | Direct bond |
| 1-46 | 2-ImidPen | H | H | Direct bond |
| 1-47 | 1-Me—2-ImidVin | H | H | Direct bond |
| 1-48 | β-ImidSty | H | H | Direct bond |
| 1-49 | 1-Ph—2-ImidVin | H | H | Direct bond |
| 1-50 | PyrMe | H | H | Direct bond |
| 1-51 | PyrMe | H | H | —CH₂— |
| 1-52 | PyrMe | H | H | =CH— |
| 1-53 | PyrMe | H | H | —CH₂—CH₂— |
| 1-54 | PyrMe | H | H | —CH=CH— |
| 1-55 | PyrMe | H | H | —CH₂—CH(Me)— |
| 1-56 | PyrMe | H | H | —CH=C(Me)— |
| 1-57 | PyrMe | CH₃ | H | Direct bond |
| 1-58 | PyrMe | CH₃ | H | —CH₂— |
| 1-59 | PyrMe | CH₃ | H | =CH— |
| 1-60 | PyrMe | CH₃ | H | —CH=CH— |
| 1-61 | PyrMe | H | 5-CH₃ | Direct bond |
| 1-62 | PyrMe | CH₃ | 5-CH₃ | Direct bond |
| 1-63 | 1-PyrEt | H | H | Direct bond |
| 1-64 | α-PyrBz | H | H | Direct bond |
| 1-65 | α-PyrBz | H | H | —CH₂— |
| 1-66 | α-PyrBz | H | H | =CH— |
| 1-67 | 2-PyrEt | H | H | Direct bond |
| 1-68 | 1-Me—2-PyrEt | H | H | Direct bond |
| 1-69 | 2-PyrPr | H | H | Direct bond |
| 1-70 | 1-Ph—2-PyrEt | H | H | Direct bond |
| 1-71 | 2-Ph—2-PyrEt | H | H | Direct bond |
| 1-72 | 2-PyrVin | H | H | Direct bond |
| 1-73 | 1-Me—2-PyrVin | H | H | Direct bond |
| 1-74 | 2-PyrPen | H | H | Direct bond |
| 1-75 | 1-Ph—2-PyrVin | H | H | Direct bond |
| 1-76 | β-PyrSty | H | H | Direct bond |

TABLE 2

| No. | Y—Z | R¹ | R² | W |
|---|---|---|---|---|
| 2-1 | ImidMe | H | H | Direct bond |
| 2-2 | ImidMe | H | H | —CH₂— |
| 2-3 | ImidMe | H | H | —CH₂—CH₂— |
| 2-4 | ImidMe | H | H | —CH=CH— |
| 2-5 | ImidMe | CH₃ | H | Direct bond |
| 2-6 | ImidMe | CH₃ | H | —CH₂— |
| 2-7 | ImidMe | CH₃ | H | —CH₂—CH₂— |
| 2-8 | ImidMe | CH₃ | H | —CH=CH— |
| 2-9 | ImidMe | H | 4-CH₃ | Direct bond |
| 2-10 | ImidMe | H | 4-CH₃ | —CH₂— |
| 2-11 | ImidMe | H | 4-CH₃ | —CH=CH— |
| 2-12 | ImidMe | H | 4-CH₃ | —CH₂—CH₂— |
| 2-13 | ImidMe | CH₃ | 4-CH₃ | Direct bond |
| 2-14 | 1-ImidEt | H | H | Direct bond |
| 2-15 | 1-ImidEt | H | H | —CH₂— |
| 2-16 | 1-ImidPr | H | H | Direct bond |
| 2-17 | α-ImidBz | H | H | Direct bond |
| 2-18 | 2,4-diCl—α-ImidBz | H | H | Direct bond |
| 2-19 | 2-F—α-ImidBz | H | H | Direct bond |
| 2-20 | 2-MeO—α-ImidBz | H | H | Direct bond |
| 2-21 | 2,4-diMeO—α-ImidBz | H | H | Direct bond |
| 2-22 | 2,4,6-triMeO—α-ImidBz | H | H | Direct bond |
| 2-23 | 2-Me—α-ImidBz | H | H | Direct bond |
| 2-24 | 2-MeO—4-Me—α-ImidBz | H | H | Direct bond |
| 2-25 | 2,4,6-triMe—α-ImidBz | H | H | Direct bond |
| 2-26 | NP—CH(Imid)— | H | H | Direct bond |
| 2-27 | 4-F—α-ImidBz | H | H | Direct tond |
| 2-28 | 4-MeO—α-ImidBz | H | H | Direct bond |
| 2-29 | 2-Me—1-ImidPr | H | H | Direct bond |
| 2-30 | 2,2-diMe—1-ImidPr | H | H | Direct bond |
| 2-31 | Imid—CH(cHx)— | H | H | Direct bond |
| 2-32 | 2-ImidEt | H | H | Direct bond |
| 2-33 | 2-ImidEt | H | H | —CH₂— |
| 2-34 | 1-Me—2-ImidEt | H | H | Direct bond |
| 2-35 | 2-ImidPr | H | H | Direct bond |
| 2-36 | 1-iPr—2-ImidEt | H | H | Direct bond |
| 2-37 | 2-iPr—2-ImidEt | H | H | Direct bond |
| 2-38 | 1-Ph—2-ImidEt | H | H | Direct bond |
| 2-39 | 2-Ph—2-ImidEt | H | H | Direct bond |
| 2-40 | 2-ImidVin | H | H | Direct bond |
| 2-41 | 2-ImidPen | H | H | Direct bond |
| 2-42 | 1-Me—2-ImidVin | H | H | Direct bond |
| 2-43 | β-ImidSty | H | H | Direct bond |
| 2-44 | 1-Ph—2-ImidVin | H | H | Direct bond |
| 2-45 | PyrMe | H | H | Direct bond |
| 2-46 | PyrMe | H | H | —CH₂— |
| 2-47 | PyrMe | H | H | —CH₂—CH₂— |
| 2-48 | PyrMe | H | H | —CH=CH— |
| 2-49 | PyrMe | H | H | —CH₂—CH(Me)— |
| 2-50 | PyrMe | H | H | —CH=CMe— |
| 2-51 | PyrMe | CH₃ | H | Direct bond |
| 2-52 | PyrMe | CH₃ | H | —CH₂— |
| 2-53 | PyrMe | CH₃ | H | —CH=CH— |
| 2-54 | PyrMe | H | 5-CH₃ | Direct bond |
| 2-55 | PyrMe | CH₃ | 5-CH₃ | Direct bond |
| 2-56 | 1-PyrEt | H | H | Direct bond |
| 2-57 | α-PyrBz | H | H | Direct bond |
| 2-58 | α-PyrBz | H | H | —CH₂— |
| 2-59 | 2-PyrEt | H | H | Direct bond |
| 2-60 | 1-Me—2-PyrEt | H | H | Direct bond |
| 2-61 | 2-PyrPr | H | H | Direct bond |
| 2-62 | 1-Ph—2-PyrEt | H | H | Direct bond |
| 2-63 | 2-Ph—2-PyrEt | H | H | Direct bond |
| 2-64 | 2-PyrVin | H | H | Direct bond |
| 2-65 | 1-Me—2-PyrVin | H | H | Direct bond |
| 2-66 | 2-PyrPen | H | H | Direct bond |
| 2-67 | 1-Ph—2-PyrVin | H | H | Direct bond |
| 2-68 | β-PyrSty | H | H | Direct bond |

TABLE 3

| No. | Y—Z | R¹ | R² | W |
|---|---|---|---|---|
| 3-1 | ImidMe | H | H | Direct bond |
| 3-2 | ImidMe | H | H | —CH₂— |
| 3-3 | ImidMe | CH₃ | H | Direct bond |
| 3-4 | ImidMe | CH₃ | H | —CH₂— |
| 3-5 | ImidMe | H | 4-CH₃ | Direct bond |
| 3-6 | ImidMe | H | 4-CH₃ | —CH₂— |
| 3-7 | ImidMe | CH₃ | 4-CH₃ | Direct bond |
| 3-8 | 1-ImidEt | H | H | Direct bond |
| 3-9 | α-ImidBz | H | H | Direct bond |
| 3-10 | 2-MeO—α-ImidBz | H | H | Direct bond |
| 3-11 | 2,4,6-triMe—α-ImidBz | H | H | Direct bond |
| 3-12 | 4-F—α-ImidBz | H | H | Direct bond |
| 3-13 | 4-MeO—α-ImidBz | H | H | Direct bond |
| 3-14 | 2-ImidEt | H | H | Direct bond |
| 3-15 | 2-Ph—2-ImidEt | H | H | Direct bond |
| 3-16 | PyrMe | H | H | Direct bond |

TABLE 3-continued

| No. | Y—Z | R¹ | R² | W |
|---|---|---|---|---|
| 3-17 | PyrMe | H | H | —CH₂— |
| 3-18 | PyrMe | CH₃ | H | Direct bond |
| 3-19 | PyrMe | CH₃ | H | —CH₂— |
| 3-20 | 2-PyrEt | H | H | Direct bond |

TABLE 4

| No. | Y—Z | R¹ | R² | W |
|---|---|---|---|---|
| 4-1 | ImidMe | H | H | Direct bond |
| 4-2 | Imide | H | H | —CH₂— |
| 4-3 | ImidMe | CH₃ | H | Direct bond |
| 4-4 | α-ImidBz | H | H | Direct bond |
| 4-5 | 2-MeO—α-ImidBz | H | H | Direct bond |
| 4-6 | 2,4,6-triMe—α-ImidBz | H | H | Direct bond |
| 4-7 | 4-F—α-ImidBz | H | H | Direct bond |
| 4-8 | 4-MeO—α-ImidBz | H | H | Direct bond |
| 4-9 | 2-ImidEt | H | H | Direct bond |
| 4-10 | 2-Ph—2-ImidEt | H | H | Direct bond |
| 4-11 | PyrMe | H | H | Direct bond |
| 4-12 | PyrMe | H | H | —CH₂— |
| 4-13 | PyrMe | CH₃ | H | Direct bond |
| 4-14 | PyrMe | CH₃ | H | —CH₂— |

TABLE 5

| No. | Y—Z | R¹ | R² | W |
|---|---|---|---|---|
| 5-1 | ImidMe | H | H | Direct bond |
| 5-2 | ImidMe | H | H | —CH₂— |
| 5-3 | ImidMe | CH₃ | H | Direct bond |
| 5-4 | ImidMe | CH₃ | 4-CH₃ | Direct bond |
| 5-5 | α-ImidBz | H | H | Direct bond |
| 5-6 | 2-MeO—α-ImidBz | H | H | Direct bond |
| 5-7 | 2-ImidEt | H | H | Direct bond |
| 5-8 | 2-ImidVin | H | H | Direct bond |
| 5-9 | PyrMe | H | H | Direct bond |
| 5-10 | PyrMe | CH₃ | H | Direct bond |
| 5-11 | PyrMe | CH₃ | H | —CH₂— |
| 5-12 | 2-PyrEt | H | H | Direct bond |

TABLE 6

| No. | Y—Z | R¹ | R² | W |
|---|---|---|---|---|
| 6-1 | ImidMe | H | H | Direct bond |
| 6-2 | ImidMe | H | H | —CH₂— |
| 6-3 | ImidMe | CH₃ | H | Direct bond |
| 6-4 | α-ImidBz | H | H | Direct bond |
| 6-5 | 2-MeO—α-ImidBz | H | H | Direct bond |
| 6-6 | 2-ImidEt | H | H | Direct bond |
| 6-7 | 2-Ph—2-ImidEt | H | H | Direct bond |
| 6-8 | 2-ImidVin | H | H | Direct bond |
| 6-9 | PyrMe | H | H | Direct bond |
| 6-10 | PyrMe | CH₃ | H | Direct bond |
| 6-11 | PyrMe | CH₃ | H | —CH₂— |
| 6-12 | 2-PyrEt | H | H | Direct bond |

TABLE 7

| No. | Y—Z | R¹ | R² | W |
|---|---|---|---|---|
| 7-1 | ImidMe | H | H | Direct bond |
| 7-2 | ImidMe | H | H | —CH₂— |
| 7-3 | ImidMe | CH₃ | H | Direct bond |
| 7-4 | ImidMe | H | 6-CH₃ | Direct bond |
| 7-5 | ImidMe | H | 6-CH₃ | —CH₂— |
| 7-6 | α-ImidBz | H | H | Direct bond |
| 7-7 | 2-MeO—α-ImidBz | H | H | Direct bond |
| 7-8 | 2-ImidEt | H | H | Direct bond |
| 7-9 | PyrMe | H | H | Direct bond |
| 7-10 | PyrMe | H | H | —CH₂— |
| 7-11 | PyrMe | CH₃ | H | Direct bond |
| 7-12 | α-PyrBz | H | H | Direct bond |

TABLE 8

| No. | Y—Z | R¹ | R² | W |
|---|---|---|---|---|
| 8-1 | ImidMe | H | H | Direct bond |
| 8-2 | ImidMe | H | H | —CH₂— |
| 8-3 | ImidMe | CH₃ | H | Direct bond |
| 8-4 | 2-MeO—α-ImidBz | H | H | Direct bond |
| 8-5 | 2-ImidEt | H | H | Direct bond |
| 8-6 | PyrMe | H | H | Direct bond |
| 8-7 | PyrMe | CH₃ | H | Direct bond |
| 8-8 | α-PyrBz | H | H | Direct bond |
| 8-9 | α-PyrBz | H | H | —CH₂— |

Of the above Compounds, preferred compounds are Compounds No. 1-1, 1-2, 1-6, 1-16, 1-17, 1-21, 1-24, 1-27, 1-29, 1-36, 1-44, 1-45, 1-50, 1-57, 1-58, 1-62, 1-67, 2-1, 2-5, 2-6, 2-13, 2-17, 2-18, 2-19, 2-20, 2-23, 2-32, 2-39, 2-45, 2-51, 2-52, 3-1, 3-3, 3-14, 3-16, 3-18, 3-20, 4-1, 4-4, 4-9, 4-11, 5-1, 5-4, 5-7, 5-9, 5-10, 6-1, 6-3, 6-6, 6-9, 7-1, 7-8, 7-9, 8-1, 8-5 and 8-6. Of these, more preferred compounds are Compounds No. 1-1, 1-6, 1-36, 1-50, 1-57, 1-67, 2-1, 2-5, 2-17, 2-32, 2-45, 3-1, 3-16, 4-1, 4-4, 4-9 and 5-1 and the most preferred compounds are Compounds No. 1-1 and 2-1, i.e.:

1-1. 4,5,6,7-tetrahydro-2-(1-imidazolyl)methylthianaphthene-6-carboxylic acid 2-1. 4,5-dihydro-2-(1-imidazolyl)methylthianaphthene-6-carboxylic acid Also preferred are pharmaceutically acceptable salts, esters and amides, particularly salts and esters of the above compounds, notably the alkali metal (especially sodium) salts and lower alkyl (especially methyl) esters.

In general terms, the compounds of the present invention may be prepared by reacting a compound of formula (II):

$$\text{(II)}$$

(in which $R^1$, $R^2$, n and the broken lines are as defined above; one of $B^1$ and $B^2$ represents the group of formula —W—COOH represented by $A^1$ or $A^2$ or such a group in which the carboxy group is protected; and the other of $B^1$ and $B^2$ represents an active group) with an imidazolyl or pyridyl compound to introduce the imidazolyl or pyridyl group represented by Y into said compound and, if necessary, subjecting the resulting compound to reduction and/or hydrolysis and/or deprotection.

In more detail, the compounds of the invention may be prepared as described in relation to any of the following Methods A–F.

Method A

In this method, a compound of formula (Ia):

$$\text{(Ia)}$$

[in which $R^1$, $R^2$, W, n and the broken lines are as defined above; $Y^1$ represents an imidazolyl group; and $Z^1$ represents a methylene, ethylene or trimethylene group which is unsubstituted or has at least one substituent selected from the group consisting of substituents (b), defined above; said group of formula —$Z^1$—$Y^1$ being at any one of the 2-, 5- and 6-positions of the thianaphthene system and said group of formula —W—COOH being at any one of said 2-, 5- and 6-positions not occupied by said group of formula —$Z^1$—$Y^1$], that is to say a compound of formula (Ia1):

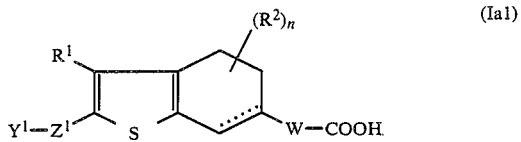

a compound of formula (Ia2):

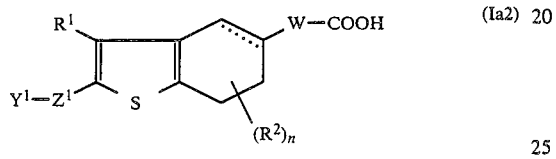

or a compound of formula (Ia3):

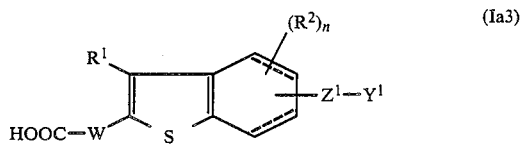

(in which $R^1$, $R^2$, n, W, $Y^1$, $Z^1$ and the broken and dotted lines are as defined above), may be produced by reacting a compound of formula (III):

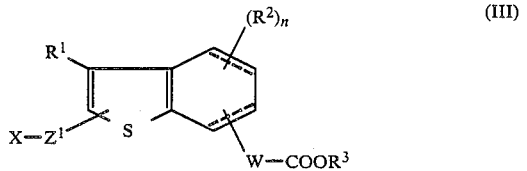

(in which $R^1$, $R^2$, W, n, $Z^1$ and the broken lines are as defined above; $R^3$ represents a carboxy-protecting group; and X represents a halogen atom, a lower alkanesulfonyloxy group or an arylsulfonyloxy group; said group of formula —$Z^1$—X being at any one of the 2-, 5- and 6-positions of the thianaphthene system and said group of formula —W—$COOR^3$ being at any one of said 2-, 5- and 6-positions not occupied by said group of formula —$Z^1$—X) with a compound of formula (IV):

$Y^1H$  (IV)

(in which $Y^1$ is as defined above), i.e. imidazole, or with an alkali metal (e.g. lithium, sodium or potassium) salt thereof and, if necessary, hydrolizing the resulting compound.

In the above formulae (II), (Ia) and (III), the provisions relating to $A^2$ in the compounds of formula (I) apply, Mutatis mutandis, to the corresponding group $B^2$, —$Z^1$—$Y^1$, —W—COOH, —$Z^1$—X or —W—$COOR^3$, i.e. when it is at the 5-position, there should be a single bond between the 6- and 7-positions, and, when it is at the 6-position, there should be a single bond between the 4- and 5-positions. The same applies in the respective formulae given hereafter.

Where X represents a halogen atom, this is preferably a chlorine, bromine or iodine atom. Where X represents a lower alkanesulfonyloxy group, this is preferably a $C_1$-$C_4$ alkanesulfonyloxy group, for example a methanesulfonyloxy or ethanesulfonyloxy group. Where X represents an arylsulfonyloxy group, the aryl part may be as defined in relation to the substituted or unsubstituted aryl groups represented by $R^1$ and $R^2$, and preferred such arylsulfonyloxy groups include the benzenesulfonyloxy and p-toluenesulfonyloxy groups.

Where the carboxy group in the group of formula —W—COOH is protected, it is preferably protected by conversion to an ester group, particularly a lower alkyl ester, and $R^3$ is for example a methyl, ethyl, propyl, isopropyl, butyl, isobutyl or t-butyl group.

The reaction between the compound of formula (III) and the compound of formula (IV) is preferably effected in the presence of a solvent, the nature of which is not critical, provided that it has no adverse effect upon the reaction. Examples of suitable solvents include: halogenated hydrocarbons, particularly halogenated aliphatic hydrocarbons, such as methylene chloride, chloroform or carbon tetrachloride; alcohols, such as methanol, ethanol or t-butanol; aromatic hydrocarbons, such as benzene, toluene or xylene; nitriles, such as acetonitrile; and lower aliphatic acid amides, such as dimethylformamide.

The reaction will take place over a wide range of temperatures and the particular temperature chosen is not critical to the invention. However, we generally find it convenient to carry out the reaction at a temperature in the range from 10° C. to the boiling point of the solvent employed. The time required for the reaction will vary, depending upon many factors, notably the nature of the reagents and the reaction temperature; however, within the range of temperatures indicated above, a period of from 1 to 20 hours will normally suffice.

Where the resulting compound is to be hydrolized, this may be effected by conventional means by contacting the ester obtained in the above reaction with a hydrolizing agent, which may be an acid or a base. There is no particular restriction upon the nature of the acid or base to be employed as hydrolizing agent, and any such compound commonly used for hydrolysis may equally be used in the present reaction. However, examples of suitable hydrolizing agents include: mineral acids, such as hydrochloride acid, hydrobromic acid and sulfuric acid; and alkali metal hydroxides, such as sodium hydroxide or potassium hydroxide.

The reaction is normally carried out in the presence of a solvent, the nature of which is not critical, provided that it has no adverse effect upon the reaction. Generally, we prefer to use as solvent an alcohol, such as methanol or ethanol, or a mixture of such an alcohol and water.

The reaction will take place over a wide range of temperatures and there is no particular limitation on the precise temperature employed. We generally find it convenient to carry out the reaction at a temperature within the range from room temperature to 110° C. The time required for the reaction may vary widely, depending upon many factors, notably the reaction temperature and the nature of the hydrolizing agent used.

However, at temperatures within the range suggested above, a period of from 10 minutes to 6 hours will normally suffice.

After completion of the reaction, the desired product may be recovered from the reaction mixture by conventional recovery techniques and then, if required, it may be further purified by such conventional techniques as recrystallization, distillation or the various chromatography techniques, notably column chromatography.

Method B

Thianaphthene compounds of formula (Ia), defined in Method A above, may also be produced by reacting a compound of formula (V):

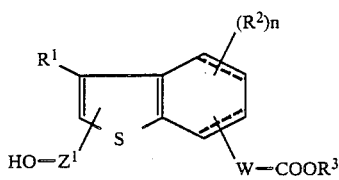

(V)

(in which $R^1$, $R^2$, $R^3$, W, $Z^1$, n and the broken lines are as defined above; said group of formula $-Z^1-OH$ being at any one of the 2-, 5- and 6-positions of the thianaphthene system and said group of formula $-W-COOR^3$ being at any one of said 2-, 5- and 6-positions not occupied by said group of formula $-Z^1-OH$) with a thionyldiimidazole compound of formula (VI):

$$Y^1-S(=O)-Y^1 \qquad (VI)$$

(in which $Y^1$ is as defined above) and, if necessary, hydrolizing the resulting compound.

As explained in Method A, the provisos relating to $A^2$ apply *Mutatis Mutandis* to whichever of said groups $-Z^1-OH$ and $-W-COOR^3$ occupies the 5- or 6- position.

The reaction of the compound of formula (V) with the thionyldiimidazole compound of formula (VI) is preferably effected in the presence of a solvent, the nature of which is not critical, provided that is has no adverse effect upon the reaction. Examples of suitable solvents include: halogenated hydrocarbons, particularly halogenated aliphatic hydrocarbons, such as methylene chloride or chloroform; ethers, such as diethyl ether, tetrahydrofuran or dioxane; and aromatic hydrocarbons, such as benzene, toluene or xylene. Although not essential, the reaction is facilitated by carrying it out in the presence of a base, preferably an organic base and more preferably a tertiary amine, such as 4-dimethylaminopyridine.

The reaction will take place over a wide range of temperatures and there is no particular limitation on the precise temperature chosen. We generally find it convenient to carry out the reaction at a temperature within the range from 0° C. to the boiling point of the solvent employed. The time required for the reaction may vary widely, depending upon many factors, notably the nature of the reagents and the reaction temperature. However, at a temperature within the range suggested above, a period of from 1 minute to 12 hours will normally suffice.

After completion of the reaction, the reaction mixture is preferably poured into water and then treated by conventional means to recover the desired compound. If necessary, this may be further purified by conventional means, for example recrystallization, distillation or the various chromatography techniques, notably column chromatography.

If hydrolysis is required, this may be carried out before or after recovery and/or purification by the conventional method described in Method A.

Method C

Compounds of formula (Ic):

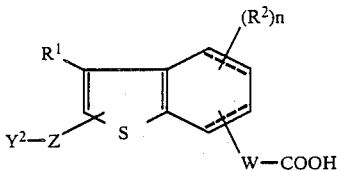

(Ic)

(in which $R^1$, $R^2$, W, Z, n and the broken lines are as defined above; and $Y^2$ represents a pyridyl group; said group of formula $-Z-Y^2$ being at any one of the 2-, 5- and 6-positions of the thianaphthene system and said group of formula $-W-COOH$ being at any one of said 2-, 5- and 6-positions not occupied by said group of formula $-Z-Y^2$) can be produced by reacting a compound of formula (VII):

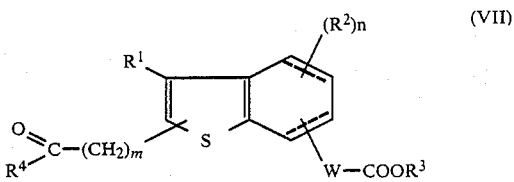

(VII)

[in which $R^1$, $R^2$, $R^3$, W, n and the broken lines are as defined above; $R^4$ represents a hydrogen atom or any of the groups defined as substituents (b), i.e. a $C_1-C_4$ alkyl group, a $C_3-C_6$ cycloalkyl group, a $C_6-C_{10}$ aryl group, a substituted $C_6-C_{10}$ aryl group having at least one of substituents (a) or a heterocyclic group; and m represents the cypher 0 or the integer 1 or 2; said group of formula $-(CH_2)_m-C(=O)-R^4$ being at any one of the 2-, 5- and 6-positions of the thianaphthene system and said group of formula $-W-COOR^3$ being at any one of said 2-, 5- and 6-positions not occupied by said group of formula $-(CH_2)_m-C(=O)-R^4$] with a lithium compound of formula (VIII):

$$Y^2-Li \qquad (VIII)$$

(in which $Y^2$ is as defined defined above), reducing or dehydrating the resulting compound and then, if desired, hydrolizing the product thus obtained.

The first step of this reaction, i.e. the reaction of the compound of formula (VII) with the lithium compound of formula (VIII) converts the group of formula $-(CH_2)_m-C(=O)-R^4$ in the compound of formula (VII) to a group of formula:

(B)

(in which m, $Y^2$ and $R^4$ are as defined above). This reaction is preferably effected in the presence of a solvent, the nature of which is not critical, provided that it has no adverse effect upon the reaction. Suitable solvents include ethers, particularly diethyl ether or tetrahydrofuran. The reaction will take place over a wide range of temperatures and the precise temperature chosen is not particularly critical, although we generally find it convenient to carry out the reaction at a temperature of from −73° C. to +30° C. The time required for the reaction may vary widely, depending upon many factors, notably the reaction temperature and the nature of the reagents; however, at a temperature within the suggested range, a period of from 30 minutes to 5 hours will normally suffice.

After completion of the reaction, the excess lithium compound (VII) is decomposed, e.g. by adding water or, more preferably, an aqueous solution of a salt, especially an ammonium salt such as ammonium chloride. The reaction mixture is then preferably treated by conventional means to recover the desired compound containing the aforementioned group of formula (B) and then the resulting compound may, if required, be further purified by such conventional means as recrystallization, distillation or the various chromatography techniques, notably column chromatography.

In the next step of the reaction, the compound containing the group of formula (B) defined above is reduced. The reduction is preferably effected by means of hydrogen in the presence of a catalyst, such as palladium-on-carbon or platinum oxide. The reaction is preferably effected in the presence of a mineral acid, such as hydrochloric acid, hydrobromic acid or sulfuric acid. The reaction is also preferably effected in the presence of a solvent, the nature of which is not critical, provided that it has no adverse effect upon the reaction. Examples of suitable solvents include: esters, such as ethyl acetate; aromatic hydrocarbons, such as benzene or toluene; and alcohols, such as methanol or ethanol. After completion of the reaction, the resulting product may be recovered from the reaction mixture by conventional means, to give a compound of formula (Ic) in which Z represents a methylene, ethylene or trimethylene group which is unsubstituted or has one or more of substituents (b).

Where m represents the integer 1, the resulting compound can be dehydrated to give a compound of formula (Ic) in which Z represents a vinylene group. This reaction is preferably effected in the presence of an organic solvent, the nature of which is not critical, provided that it has no adverse effect upon the reaction. Examples of suitable organic solvents include: aromatic hydrocarbons, such as benzene, toluene or xylene; and ethers, such as dioxane or tetrahydrofuran. The dehydration reaction is preferably effected by the addition of a catalytic amount of a strong acid, for example an organic sulfonic acid such as p-toluenesulfonic acid or a mineral acid such as hydrochloric acid, hydrobromic acid or sulfuric acid. The water produced in the reaction is removed, preferably in the course of the reaction, to assist the reaction to go to completion, and preferably by azeotropic distillation with heating.

If necessary, the product is then subjected to hydrolysis as described in Method A. After completion of the reaction, the desired product may be recovered from the reaction mixture by conventional means, to give a compound of formula (Ic) in which Z represents a vinylene group, which may be unsubstituted or have at least one of substituents (b).

If required, the resulting compound prepared as described above may be further purified by such conventional techniques as recrystallization or the various chromatography techniques, notably column chromatography.

Method D

Compounds of formula (Id):

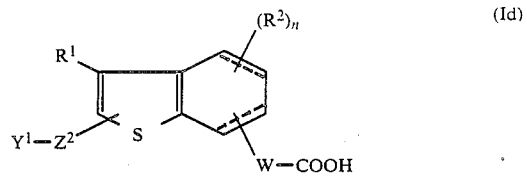

[in which $R^1$, $R^2$, W, $Y^1$, n and the broken lines are as defind above; and $Z^2$ represents a vinylene group or a vinylene group having at least one of substituents (b) defined above, that is to say an alkyl group, a cycloalkyl group, a substituted or unsubstituted aryl group or a heterocyclic group; said group of formula $—Z^2—Y^1$ being at any one of the 2-, 5- and 6-positions of the thianaphthene system and said group of formula $—W—COOH$ being at any one of said 2-, 5- and 6-positions not occupied by said group of formula $—Z^2—Y^1$] can be prepared by reacting a compound of formula (VIII):

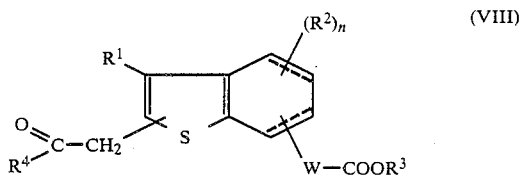

[in which $R^1$, $R^2$, $R^3$, $R^4$, W, n and the broken lines are as defined above; said group of formula $—CH_2—C(=O)—R^4$ being at any one of the 2-, 5- and 6-positions of the thianaphthene system and said group of formula $—W—COOR^3$ being at any one of said 2-, 5- and 6-positions not occupied by said group of formula $—CH_2—C(=O)—R^4$], i.e. a compound of formula (VII) (see Method C) in which m is 1, with a thionyldiimidazole compound of formula (VI):

$$Y^1—S(=O)—Y^1 \qquad (VI)$$

(in which $Y^1$ is as defined above—see Method B) and, if necessary, hydrolizing the resulting compound.

The reaction of these compounds may be carried out employing the same reaction conditions and subsequent treatment as described in Method B.

Method E

A thianaphthene derivative of formula (Ie):

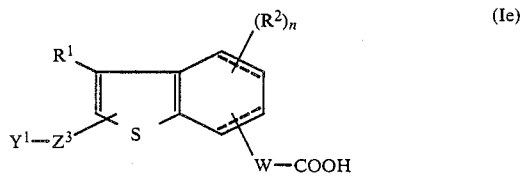

[in which $R^1$, $R^2$, W, $Y^1$, n and the broken lines are as defined above; and $Z^3$ represents an ethylene, trimethylene or vinylene group or such a group having at least one substituent selected from the group consisting of substituents (b), that is to say the alkyl, cycloalkyl, substituted and unsubstituted aryl and heterocyclic groups defined above; said group of formula —$Z^3$—$Y^1$ being at any one of the 2-, 5- and 6-positions of the thianaphthene system and said group of formula —W—COOH being at any one of said 2-, 5- and 6-positions not occupied by said group of formula —$Z^3$—$Y^1$] can be prepared by reacting a compound of formula (IX):

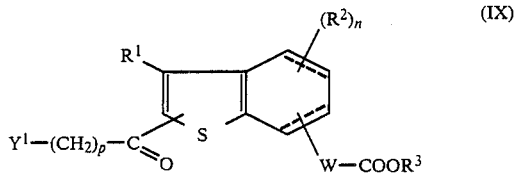

[in which $R^1$, $R^2$, $R^3$, $Y^1$, W, n and the broken lines are as defined above; and p is 1 or 2; said group of formula —C(=O)—$(CH_2)_p$—$Y^1$ being at any one of the 2-, 5- and 6-positions of the thianaphthene system and said group of formula —W—$COOR^3$ being at any one of said 2-, 5- and 6-positions not occupied by said group of formula —C(=O)—$(CH_2)_p$—$Y^1$] with a reducing agent or with an organolithium compound of formula (X):

$$R^5Li \qquad (X)$$

or with a Grignard reagent of formula (XI):

$$R^5MgX' \qquad (XI)$$

[in which $R^5$ represents any one of the groups defined above as substituents (b), that is to say a $C_1$-$C_4$ alkyl group, a $C_3$-$C_6$ cycloalkyl group, a $C_6$-$C_{10}$ aryl group, a substituted $C_6$-$C_{10}$ aryl group or a heterocyclic group; and X' represents a halogen atom, for example a chlorine, bromine or iodine atom] to give a compound of formula (XII):

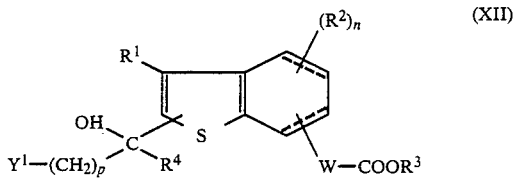

[in which $R^1$, $R^2$, $R^3$, W, $Y^1$, n, p and the broken lines are as defined above; said group of formula —(OH)C($R^4$)—$(CH_2)_p$—$Y^1$ being at any one of the 2-, 5- and 6-positions of the thianaphthene system and said group of formula —W—$COOR^3$ being at any one of said 2-, 5- and 6-positions not occupied by said group of formula —(OH)C($R^4$)—$(CH_2)_p$—$Y^1$], and then reducing and/or dehydrating said compound of formula (XII) and, if desired, hydrolizing the resulting product.

Where, in the first step of this reaction, the compound of formula (IX) is reacted with a reducing agent, the reducing agent is preferably a metal hydride, such as sodium borohydride or sodium cyanoborohydride. The reaction is preferably effected in the presence of a solvent, the nature of which is not critical, provided that it has no adverse effect on the reaction. Suitable solvents include, for example: ethers, such as diethyl ether or tetrahydrofuran; and alcohols, such as methanol. The reaction will take place over a wide range of temperatures and the particular temperature chosen is not critical to the invention. In general, we find it convenient to carry out the reaction at a temperature in the range from 0° C. to the boiling temperature of the solvent employed. The time required for the reaction may vary widely, depending upon many factors, notably the nature of the reagents and the reaction temperature; however, at a temperature within the suggested range, a period of from 30 minutes to 5 hours will normally suffice. After completion of the reaction, the reaction mixture may be treated by conventional means to recover the desired product, after which the product, the compound of formula (XII), may be further purified by such conventional techniques as recrystallization, distillation or the various chromatograhy techniques, notably column chromatography.

Alternatively, in the first step of the reaction, the compound of formula (IX) may be reacted with the organolithium compound of formula (X). This reaction is preferably effected in the presence of a solvent, the nature of which is not critical, provided that it has no adverse effect upon the reaction. Suitable solvents include ethers, such as diethyl ether or tetrahydrofuran. The reaction will take place over a wide range of temperatures and the precise temperature chosen is not critical to the present invention. In general, we find it convenient to carry out the reaction at a temperature in the range from −73° C. to +30° C. The time required for the reaction may vary widely, depending upon many factors, notably the nature of the reagents and the reaction temperature; however, at a temperature within the suggested range, a period of from 30 minutes to 5 hours will normally suffice. After completion of the reaction, we prefer to decompose excess organolithium compound by adding water or, more preferably, an aqueous solution of a salt, especially an ammonium salt such as ammonium chloride, to the reaction mixture. After this the mixture may be treated by conventional means to recover the desired compound of formula (XII) which may then, if required, be further purified by such conventional techniques as distillation, recrystallization or the various chromatography techniques, notably column chromatography.

As a further alternative, the compound of formula (IX) may be reacted with a Grignard reagent of formula (XI). This reaction is preferably effected in the presence of a solvent, the nature of which is not critical, provided that it has no adverse effect upon the reaction and is essentially inert to the Grignard reagent; examples of suitable solvents include such ethers as diethyl ether and tetrahydrofuran. The reaction will take place over a wide range of tempertures and the particular temperature chosen is not critical to the invention. We generally find it conveient to carry out the reaction at a temperature in the range from 0° C. to the boiling temperature of the solvent employed. The time required for the reaction may vary widely, depending upon many factors, notably the nature of the reagents and the reaction temperature; however, at temperatures within the suggested range, a period of from 30 minutes to 10 hours will normally suffice. After completion of the reaction, we prefer to decompose excess Grignard reagent (XI) by adding water or, more preferably, an aqueous solution of a salt, especially an ammonium salt such as ammonium chloride, to the reaction mixture. The mixture may then be treated by conventional means to recover the desired compound of formula (XII), which may then, if required, be further purified by such conventional techniques as distillation, recrystallizaton or the various chromatograhy techniques, notably column chromatography.

The resulting compound of formula (XII), however prepared, is then subjected to reduction and/or dehydration. If desired, the compound of formula (XII) may then be subjected to the same reduction or dehydration reactions as described in relation to Method C. However, a more preferred sequence of reactions is as follows.

First, the compound of formula (XII) is reacted with an alkali metal hydride, for example sodium hydride, by stirring the compound with the hydride, preferably in the presence of a suitable solvent. The nature of the solvent is not critical, provided that it has no adverse effect upon the reaction. Suitable solvents include: ethers, and such as diethyl ether or tetrahydrofuran; and aromatic hydrocarbons, such as benzene or toluene. The reaction temperature is not critical, and we generally find it convenient to carry out the reaction at a temperature in the range of from 0° C. to the boiling point of the solvent employed. Subsequently, carbon disulfide and a lower alkyl halide, e.g. a methyl halide such as methyl iodide, are added. These are then allowed to react to give a compound of formula (XIII):

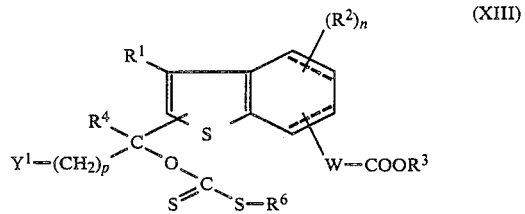

(XIII)

[in which $R^1$, $R^2$, $R^3$, $R^4$, W, $Y^1$, n, p and the broken lines are as defined above; and $R^6$ represents a lower alkyl group, preferably a methyl group; each of the groups of formula —W—$COOR^3$ and —($R^4$)-C(—$OCS_2R^6$)—$(CH_2)_p$—$Y^1$ being at any one of the 2-, 5- and 6-positions, provided that they are not both at the same position]. The reaction will take place over a wide range of temperatures and the precise temperature chosen is not particularly critical; however, we generally find it convenient to carry out the reaction at a temperature within the range from 0° C. to the boiling point of the solvent employed. The time required for the reaction may vary widely, depending upon the nature of the reagents and the reaction temperature; however, at a temperature in the suggested range, a period of from 10 minutes to 1 hour will normally suffice. The reaction is preferably effected in the same reaction medium as was used for the reaction with the alkali metal hydride.

The resulting compound is then reduced, preferably with tributyltin hydride, or dehydrated and, if necessary, hydrolized, to give the desired compound of formula (Ie).

Free radical reduction of the compound of formula (XIII) with tributyltin hydride is preferably effected in the presence of an organic solvent, the nature of which is not critical, provided that it does not interfere with the reaction. Examples of suitable solvents include: ethers, such as diethyl ether or tetrahydrofuran; and aromatic hydrocarbons, such as benzene or toluene; a single one of these solvents or a mixture of any two or more thereof may be employed. The reaction is preferably also effected in the presence of $\alpha,\alpha'$-azobisisobutyronitrile. The reaction is preferably effected with heating, suitably under reflux, to give the desired compound of formula (Ie) in which Z represents an ethylene or trimethylene group which is unsubstituted or has at least one of substituents (b). The time required for the reaction may vary widely, depending upon many factors, notably the reaction temperature, but a period of from 10 to 30 hours will normally suffice.

Alternatively, the compound of formula (XIII) may be dehydrated. This is preferably effected by the addition of a catalytic amount of a strong acid, for example an organic sulfonic acid such as p-toluenesulfonic acid or a mineral acid such as hydrochloric acid, hydrobromic acid or sulfuric acid. The reaction is preferably effected in the presence of an organic solvent, the nature of which is not critical, provided that it does not interfere with the reaction. Suitable solvents include, for example: aromatic hydrocarbons, such as benzene, toluene or xylene; and ethers, such as dioxane or tetrahydrofuran. The water produced in the reaction is preferably removed in the course of the reaction to assist the reaction to go to completion. Removal of the water is preferably effected by means of azeotropic distillation. The resulting product is a compound of formula (Ie) in which Z represents a vinylene group which is unsubstituted or has at least one of substituents (b).

If required, the resulting product may be subjected to hydrolysis, as described in relation to Method A.

The resulting compounds may be separated from their respective reaction mixtures by conventional means and, if required, may be further purified by such conventional techniques as recrystallization or the various chromatography techniques, notably column chromatography.

Method F

Tetrahydrothianaphthene derivatives of formula (If):

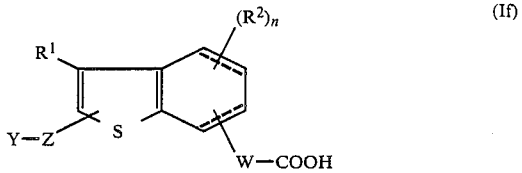

(If)

(in which $R^1$, $R^2$, W, Y, Z and n are as defined above; each of said groups of formula —Z—Y and —W—COOH being at any one of the 2-, 5- and 6-positions, provided that they are not both at the same position) may be prepared from the corresponding dihydrothianaphthene derivative (i.e. having a double bond between the 4- and 5- or the 6- and 7-positions) by reductive hydrogenation. The starting material may have been prepared by any of the forgoing Methods A–E.

The reduction process is preferably effected in the presence of a solvent, the nature of which is not critical, provided that it has no adverse effect upon the reaction. Examples of suitable solvents include: esters, such as ethyl acetate; aromatic hydrocarbons, such as benzene or toluene; alcohols, such as methanol or ethanol; and ethers, such as tetrahydrofuran or dioxane. The reaction takes place in the presence of hydrogen and of a catalyst, preferably palladium-on-carbon or platinum oxide.

After completion of the reaction, the resulting product may be recovered from the reaction mixture by conventional means and, if required, before or after recovery may be subjected to hydrolysis as described in Method A. The product of formula (If) may then, if desired, be further purified by such conventional techniques as distillation, recrystallization or the various chromatography techniques, notably column chromatography.

The starting materials employed in the above Methods may be prepared by a variety of methods well known for producing compounds of this type. By way of example, the following Methods G-P may be used.

Method G

In this method, the starting materials of formulae (III), (V) and (VII) in which Z represents an optionally substituted methylene group, W represents a direct bond and the group —W—COOR$^3$ is at the 5- or 6-position, that is to say compounds of formulae (IIIa), (Va) and (VIIa), may be prepared as illustrated by the following reaction scheme:

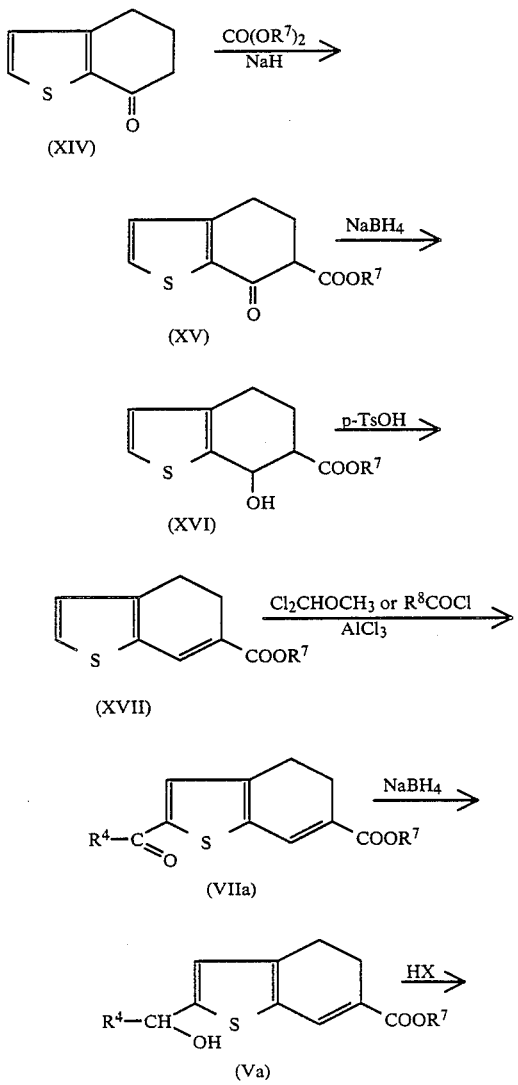

-continued

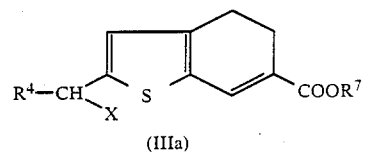
(IIIa)

In the above formulae, $R^4$ is as defined above; $R^7$ represents a carboxy-protecting group (e.g. as illustrated in relation to the group $R^3$ defined above); and $R^8$ represents an alkyl, cycloalkyl or substituted or unsubstituted aryl group as defined in relation to the corresponding groups represented by substituents (b).

The corresponding compounds of formulae (VIIb), (Vb) and (IIIb):

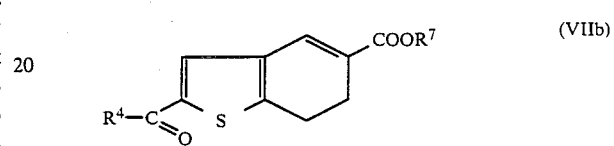
(VIIb)

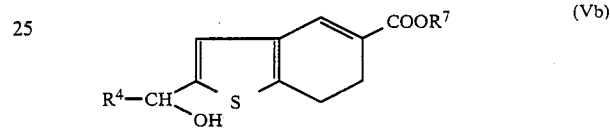
(Vb)

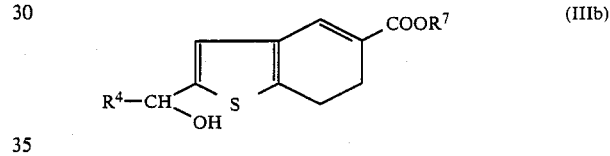
(IIIb)

(in which $R^4$, $R^7$ and X are as defined above), i.e. with the group —COOR$^7$ at the 5-position, may be prepared by precisely the same reaction sequence as illustrated above but starting with a compound of formula (XIVa):

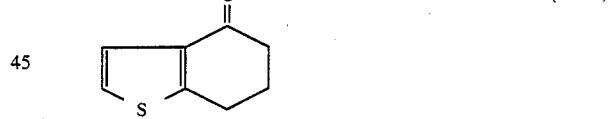
(XIVa)

in place of the compound of formula (XIV).

In the first step of this reaction, the starting material of formula (XIV) [or (XIVa)] is reacted with a dialkyl carbonate of formula CO(OR$^7$)$_2$ in the presence of a metal hydride, e.g. sodium hydride, to prepare the compound of formula (XV). This is then reacted with a reducing agent, for example sodium borohydride, to reduce the ketonic oxygen to a hydroxy group in the compound of formula (XVI). This is then reacted with a dehydrating agent, for example p-toluenesulfonic acid (p-TsOH), preferably under reflux and preferably in solution in, for example, benzene, to give the compound of formula (XVII). This is then subjected to a Friedel-Crafts reaction with a compound of formula Cl$_2$CHOCH$_3$ or R$^8$COCl in the presence of aluminum chloride to give the acyl compound (VIIa) [or (VIIb)]. If desired, this may be reduced, for example with sodium borohydride, to give the corresponding alcohol (Va) [or (Vb)] and, again if desired, this may be halogenated or sulfonylated by conventional means to give the halogen or sulfonyl derivative of formula (IIIa) [or (IIIb)].

Method H

Starting materials of formulae (III) and (V) in which $Z^1$ represents an optionally substituted ethylene group and the group —$COOR^7$ is at the 5- or 6-position, that is to say compounds of formulae (IIIc) and (Vc), and compounds of formula (VII) in which m is 1, $R^4$ is a hydrogen atom, W represents a direct bond and the group $COOR^3$ is at the 5- or 6-position, that is to say compounds of formula (VIId), may be prepared as illustrated by the following reaction scheme:

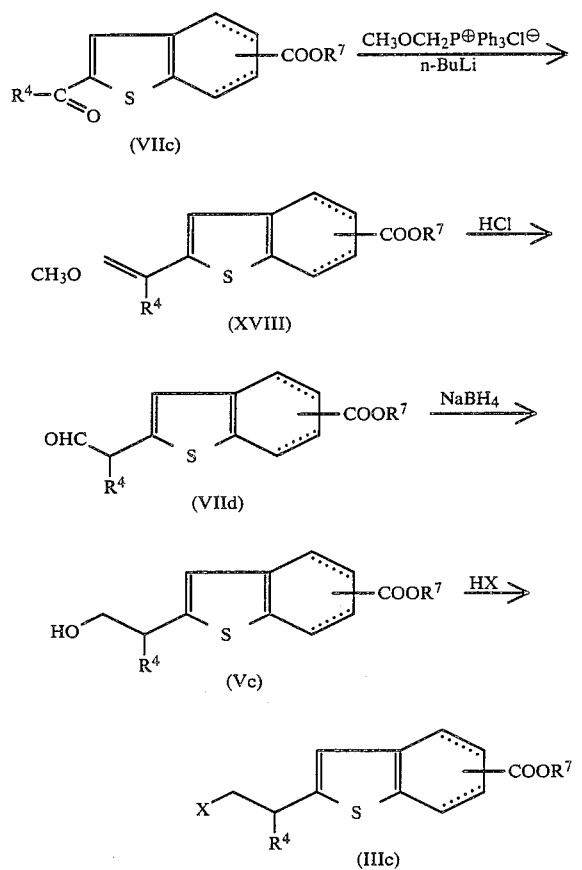

In the above formulae, $R^4$, $R^7$ and X are as defined above; the group —$COOR^7$ is at the 5- or 6-position; and the dotted lines mean that, where —$COOR^7$ is at the 5-position, there is a double bond between the 4- and 5-positions and a single bond between the 6- and 7-positions, and, where —$COOR^7$ is at the 6-position, there is a double bond between the 6- and 7-positions and a single bond between the 4- and 5-positions.

In the first step of this reaction, the compound of formula (VIIc) [i.e. a compound of formula (VIIa) or (VIIb) prepared as described in Method G] is subjected to a Wittig reaction with a compound of formula $CH_3OCH_2P^+Ph_3Cl^-$ (Ph is phenyl) in the presence of, for example, butyllithium (n-BuLi) to give the compound of formula (XVIII). This is then hydrolized to give the aldehyde of formula (VIId), e.g. by means of aqueous hydrochloric acid. If desired, this aldehyde may be reduced, for example with sodium borohydride, to give the alcohol (Vc) and this may be halogenated or sulfonylated to give the compound of formula (IIIc).

Method I

In this method, a compound of formula (IX) in which W represents a direct bond and the group —$COOR^3$ is at the 5- or 6-position, i.e. a compound of formula (IXa), may be prepared as illustrated in the following reaction scheme:

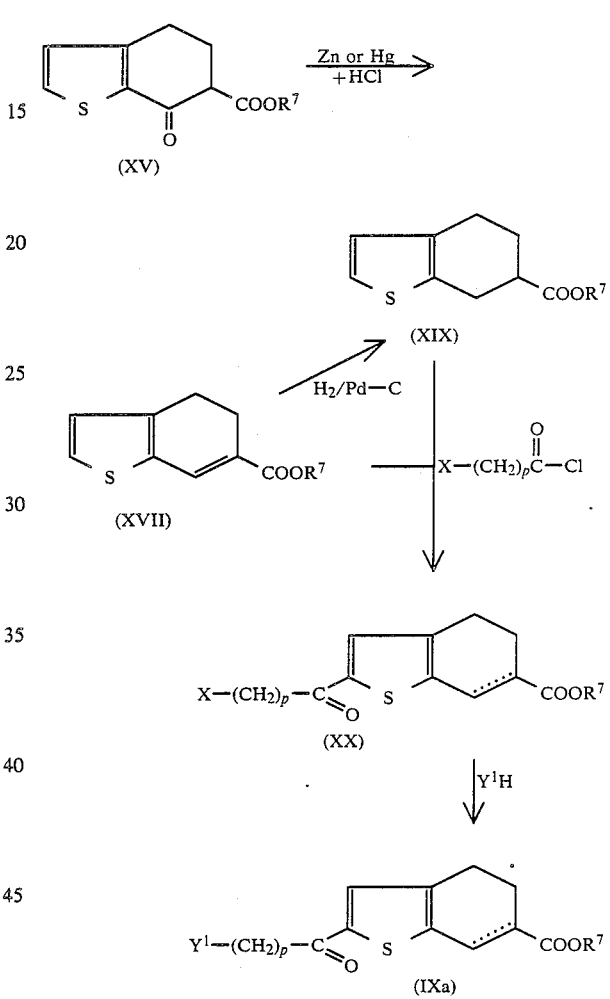

In the above formulae, $R^7$, X, $Y^1$ and p are as defined above. The dotted line means a single or double bond between the 6- and 7-positions.

The starting material is either a compound of formula (XV) or a compound of formula (XVII)—see Method G.

Where the starting material is a compound of formula (XV), this is subjected to a Clemmensen reduction using a metal, such as zinc or mercury, and an acid, such as hydrochloric acid or acetic acid, to give a compound of formula (XIX). Alternatively, the compound of formula (XIX) may be prepared from the compound of formula (XVII) by catalytic hydrogenation, using, for example, palladium-on-carbon or platinum oxide as the catalyst.

The compound of formula (XVII) or (XIX) (which differ only in the presence or absence of a double bond between the 6- and 7-positions) is then subjected to a Friedel-Crafts reaction with a compound of formula X—(CH$_2$)$_p$C(=O)—Cl to give the acyl compound of formula (XX). This is then reacted with imidazole (Y$^1$H) to give the desired starting material of formula (IXa).

Compounds of formula (IXb):

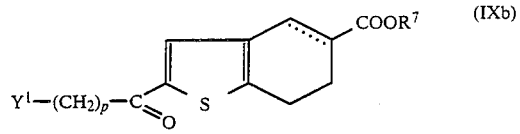
(IXb)

(in which R$^7$, Y$^1$, p and the dotted line are as defined above) may be prepared by the same sequence of reactions as illustrated above, but starting with the corresponding compound of formula (XVa) or (XVIIa):

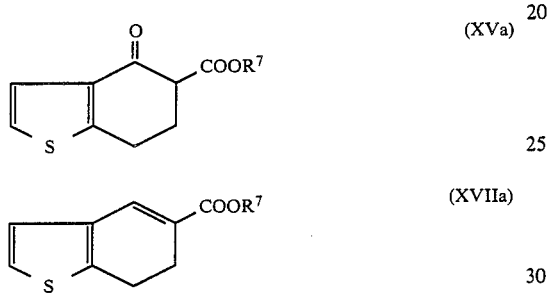
(XVa)

(XVIIa)

(in which R$^7$ is as defined above).

Method J

Starting materials of formulae (VIIe), (Vd) and (IIId), that is to say compounds of formula (VII), (V) and (III) in which W represents a methine group at the 6-position (and hence the broken lines both represent single bonds), m is 0 and Z$^1$ represents a methylene group which is unsubstituted or has at least one of substituents (b), may be prepared as illustrated by the following reaction scheme:

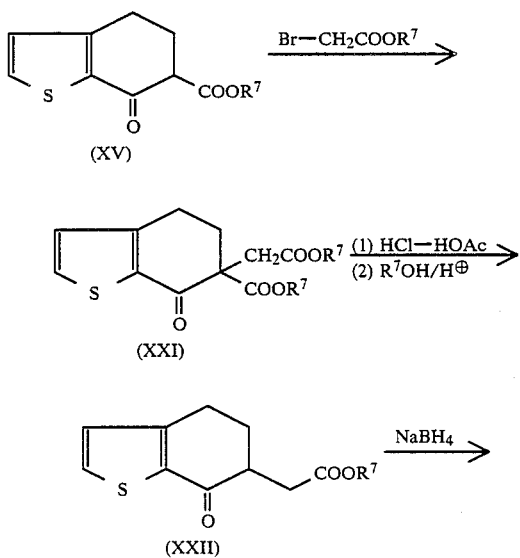

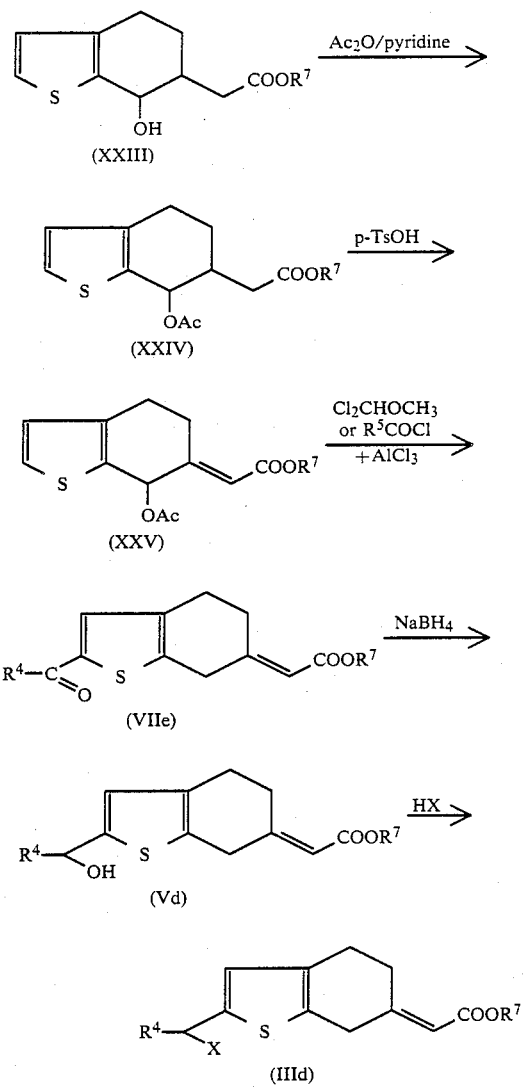

In the above formulae, R$^4$, R$^5$, R$^7$ and X are as defined above. In the compound of formula (XXI), the two groups represented by R$^7$ may be the same or different. Ac represents the acetyl group.

In the first step of this process, the compound of formula (XV) is reacted with a haloacetic, preferably bromoacetic, acid ester Br—CH$_2$COOR$^7$, to prepare the compound of formula (XXI). This is then subjected to hydrolysis, decarboxylation and then esterification to give the compound of formula (XXII). Reduction of this compound of formula (XXII) by conventional means, e.g. with sodium borohydride, yields the hydroxy compound of formula (XXIII), which is then acetylated, e.g. with acetic anhydride, preferably in the presence of a base (such as pyridine), to give the acetoxy compound of formula (XXIV). Reaction of this compound with a strong acid, such as p-toluenesulfonic acid, eliminates acetic acid and yields the methine compound of formula (XXV). This is then subjected to a Friedel-Crafts reaction to introduce the group R$^4$—C(=O)— and give the compound of formula (VIIe). If desired, this may be reduced, e.g. with sodium borohydride, to give the alcohol of formula (Vd), which may then, if desired, be halogenated or sulfonylated to give the compound of formula (IIId).

Compounds corresponding to those of formulae (VIIe), (Vd) and (IIId) but in which the methine group represented by W is replaced by a methylene group can be prepared by subjecting the compound of formula (XXV) to catalytic hydrogenation, e.g. in the presence of a catalyst such as palladium-on-carbon or platinum oxide, and then subjecting the resulting compound to the subsequent reactions in place of the compound of formula (XXV).

Additionally, corresponding compounds having the group —W—COOR⁷ (in which W represents a methine group or a methylene group) at the 5-position may be prepared by carrying out the same series of reactions, but commencing with a compound of formula (XVa):

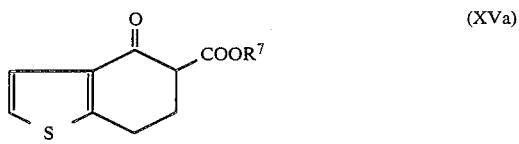

(in which R⁷ is as defined above) in place of the compound of formula (XV).

Method K

Starting materials of formula (III) where W is a direct bond, there is a double bond between the 4- and 5-positions and Z¹ represents a methylene group, that is to say compounds of formula (IIIe), may be prepared as illustrated in the following reaction scheme:

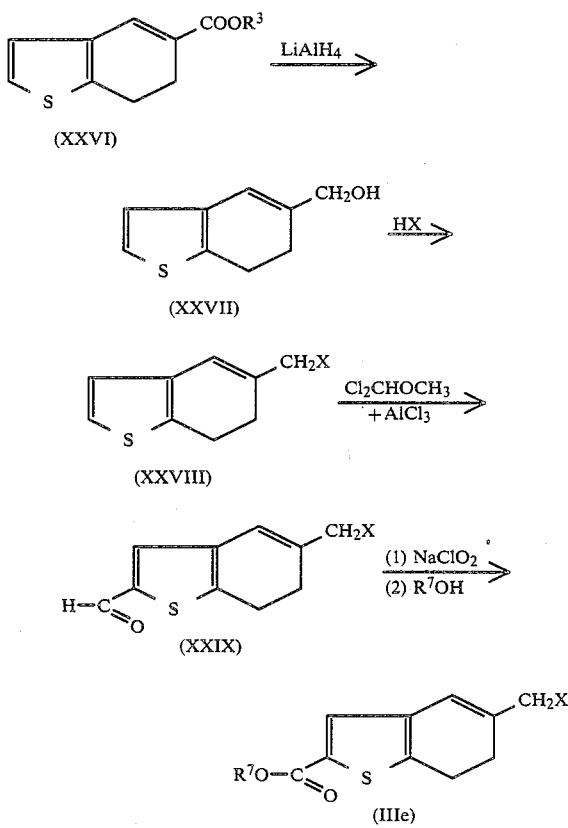

In the above formulae, R³, R⁷ and X are as defined above.

In the first step of this scheme, the compound of formula (XXVI) is reduced with a suitable reducing agent, such as lithium aluminum hydride, to give the compound of formula (XXVII). This is then halogenated or sulfonylated by conventional means to give the compound of formula (XXVIII). The compound of formula (XXVIII) is then subjected to a Friedel-Crafts reaction to introduce a formyl group at the 2-position and give the compound of formula (XXIX), which is then oxidized (e.g. with sodium chlorite) and esterified to give the compound of formula (IIIe).

Compounds corresponding to those of formula (IIIe) but in which the double bond is between the 6- and 7-positions and the group —CH₂X is at the 6-position may be prepared by following the same sequence of reactions as described above but starting with a compound corresponding to that of formula (XXVI) but in which the double bond is between the 6- and 7-positions and the group of formula —COOR³ is at the 6-position.

Also, tetrahydrothianaphthene derivatives (i.e. having single bonds both between the 4- and 5-positions and between the 6- and 7-positions) and in which the group —CH₂X is at either the 5- or the 6-position may be prepared by hydrogenating the compound of formula (XXVI) or its analog having the double bond between the 6- and 7-positions and the group —COOR³ at the 6-position, preferably employing palladium-on-carbon or platinum oxide as the catalyst.

Method L

Compounds of formula (III) in which W represents a direct bond, Z¹ represents an optionally substituted ethylene group, there is a double bond between the 4- and 5-positions and the group —W—COOR³ is at the 5-position, that is to say compounds of formula (IIIf), may be prepared as illustrated by the following reaction scheme:

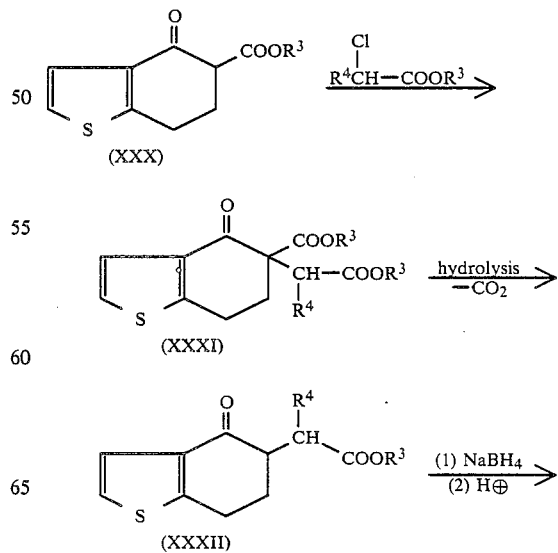

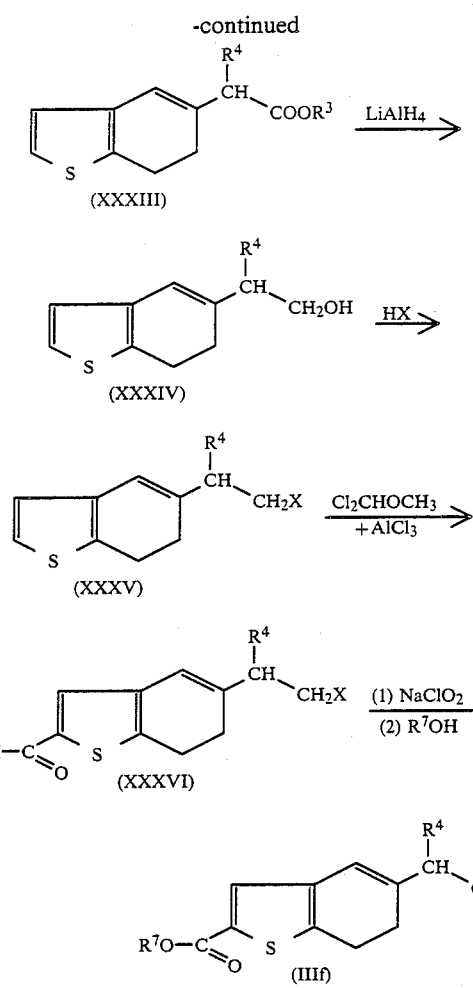

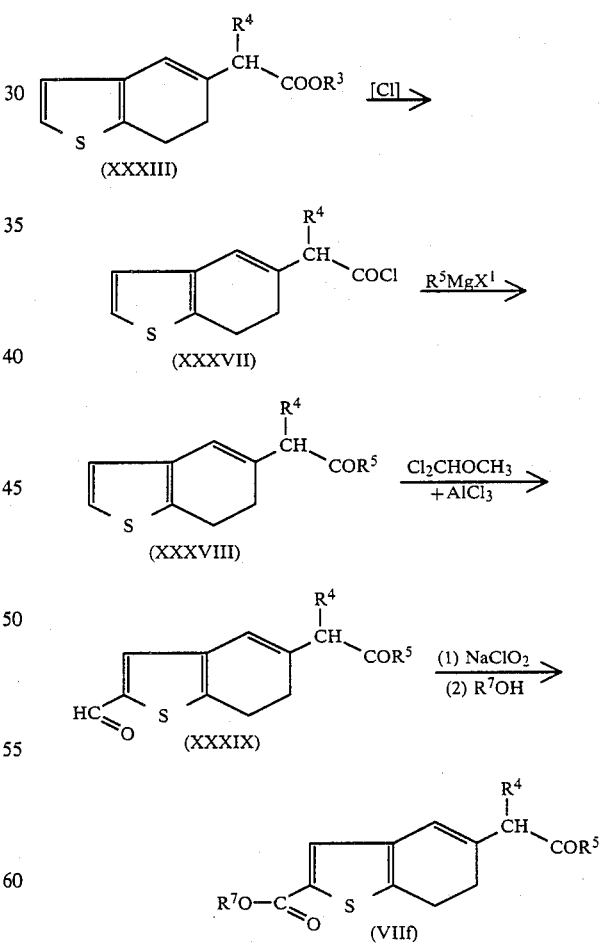

In the above formulae, $R^3$, $R^4$, $R^7$ and X are as defined above. In the compound of formula (XXXI), the two groups represented by $R^3$ may be the same or different.

In the first step of this reaction, an elongated side chain is introduced into the compound of formula (XXX) by reacting it with an optionally substituted haloacetic (preferably chloroacetic) acid or ester thereof, $R^4CH(Cl)$—$COOR^3$, to give the compound of formula (XXXI). This is then hydrolized and decarboxylated to give the compound of formula (XXXII), which is reduced, preferably with sodium borohydride, and dehydrated with a strong acid (e.g. p-toluenesulfonic acid) to give the compound of formula (XXXIII). This is then again reduced, this time preferably with lithium aluminum hydride, to give the compound of formula (XXXIV), which is then halogenated or sulfonylated to give the compound of formula (XXXV). This is subjected to a Friedel-Crafts reaction to give the compound of formula (XXXVI), which is then oxidized, preferably with sodium chlorite, and esterified, to give the desired compound of formula (IIIf).

If desired, a compound corresponding to the compound of formula (IIIf) but in which the double bond is between the 6- and 7-positions and the group of formula —$CH(R^4)$—$CH_2X$ is at the 6-position may be prepared by the same sequence of reactions but starting with a compound corresponding to the compound of formula (XXX) in which the ketonic oxygen is at the 7-position (instead of the 4-position) and the group —$COOR^3$ is at the 6-position (instead of the 5-position).

If desired, the corresponding tetrahydrothianaphthene derivatives having single bonds both between the 4- and 5-positions and between the 6- and 7-positions and having the group —$CH(R^4)$—$CH_2X$ at the 5- or the 6-position may be prepared by subjecting the compound of formula (XXXIII) or its analog having the double bond between the 6- and 7-positions and the group —$CH(R^4)$—$COOR^3$ at the 6-position to catalytic hydrogenation, preferably employing palladium-on-carbon or platinum oxide as the catalyst, to reduce the 4,5 or 6,7 double bond and then subjecting the resulting compound to the same sequence of reactions as the compound of formula (XXXIII).

Method M

Compounds of formula (VII) in which W represents a direct bond, the group —W—$COOR^7$ is at the 2-position, m is 0, the —$CH_2$— group is optionally substituted, the resulting group —$CH(R^4)$—$COR^5$ is at the 5-position and there is a double bond between the 4- and the 5-positions, that is to say compounds of formula (VIIf), may be prepared as illustrated in the following reaction scheme:

In the above formulae, $R^3$, $R^4$, $R^5$, $R^7$ and X' are as defined above.

In the first stage of this process, the compound of formula (XXXIII) (which may have been prepared as described above in relation to Method L) is converted into its corresponding acid halide, preferably the acid chloride, the compound of formula (XXXVII), by reaction with a halogenating agent, e.g. thionyl chloride or phosphorus pentachloride. This is then reacted with a Grignard reagent, $R^5MgX'$, to give the ketonic compound (XXXVIII), which is then subjected to a Friedel-Crafts reaction, to give the compound of formula (XXXIX). The resulting compound is then first oxidized, e.g. with sodium chlorite, and then esterified, to give the desired compound of formula (VIIf).

A compound corresponding to the compound of formula (VIIf), but in which the double bond is between the 6- and 7-positions and the group of formula —CH($R^4$)—COR$^5$ is at the 6-position, may be prepared by carrying out the same sequence of reactions as described above but starting with a compound corresponding to the compound of formula (XXXIII) but with the double bond between the 6- and 7-positions and the group of formula —CH($R^4$)—COOR$^3$ at the 6-position (this itself may be prepared as described in relation to the corresponding compound in Method L).

The corresponding tetrahydrothianaphthene compounds having double bonds both between the 4- and 5-positions and between the 6- and 7-positions and having the group of formula —CH($R^4$)COR$^5$ at either the 5- or the 6-position may be prepared by the same reactions as described above, except that the starting material of formula (XXXIII) or its analog having the double bond between the 6- and 7-positions and the group of formula —CH($R^4$)—COOR$^3$ at the 6-position is hydrogenated (preferably in the presence of palladium-on-carbon or platinum oxide as catalyst) and the resulting hydrogenated compound is then subjected to the above reaction sequence.

Method N

Compounds of formula (IX) in which W represents a direct bond, p is 0, the double bond is between the 4- and 5-positions and the group —COOR$^3$ is at the 2-position, that is to say compounds of formula (IXb), may be prepared as illustrated by the following reaction scheme:

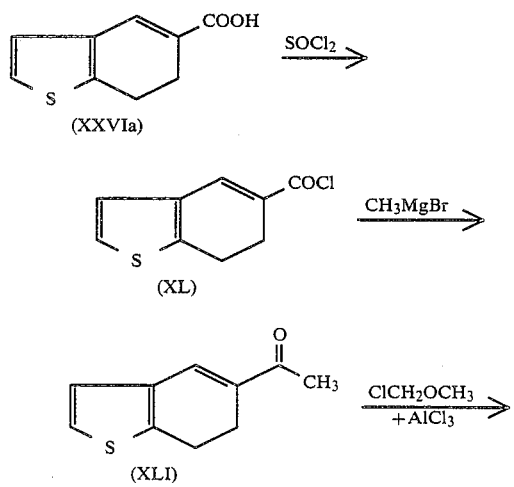

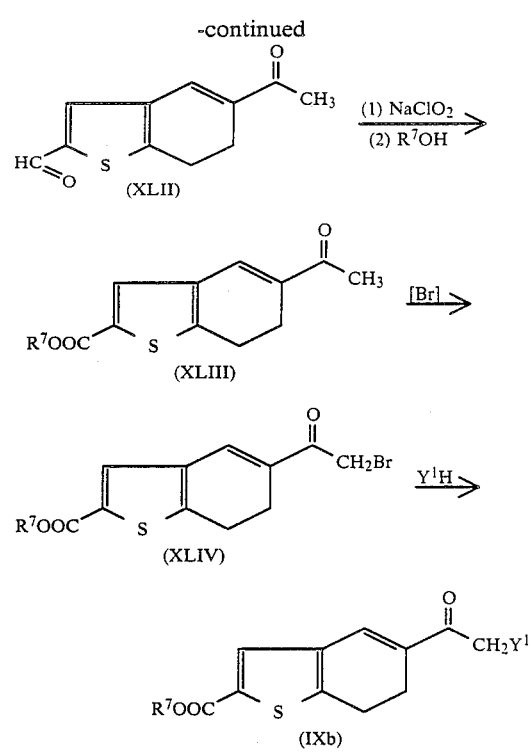

In the above formulae, $R^7$ and $Y^1$ are as defined above.

In the first step of this reaction, the compound of formula (XXVIa) is converted to its acid halide, e.g. the acid chloride (XL), by reaction with a halogenating agent, for example thionyl chloride, phosphorus pentachloride or phosphorus oxychloride. The resulting acid halide (XL) is then subjected, in turn, to the following reactions: reaction with a Grignard reagent of formula CH$_3$MgBr to give the ketonic compound (XLI); a Friedel-Crafts reaction to give the aldehyde (XLII); oxidation, preferably with sodium chlorite, and then esterification to give the ester (XLIII); bromination to give the bromide (XLIV); and finally reaction with imidazole (Y$^1$H) to give the compound of formula (IXb).

The corresponding compound in which the double bond is between the 6- and 7-positions and the group —C(=O)—CH$_2$Y$^1$ is at the 6-position may be prepared by the same sequence of reactions, but starting with a compound corresponding to the compound of formula (XXVIa) but in which the double bond is between the 6- and 7-positions and the group —COOH is at the 6-position.

The corresponding tetrahydrothianaphthene compounds having single bonds both between the 4- and 5-positions and between the 6- and 7-positions and having the group —C(=O)—CH$_2$Y$^1$ at either the 5-position or the 6-position may be prepared by hydrogenating the compound of formula (XXVIa) or its analog having the double bond between the 6- and 7-positions and the carboxyl group at the 6-position, preferably using palladium-on-carbon or platinum oxide as the catalyst.

Method O

Compounds of formula (III) in which W represents a vinylene group, the group —W—COOR$^3$ is at the 2-position, there is a double bond between the 4- and 5-positions, $Z^1$ represents a methylene group and the group —CH$_2$X (i.e. —Z$^1$—X) is at the 5-position, that is to say compounds of formula (IIIg), may be prepared by a Wittig reaction from the compound of formula (XXIX) (see Method K), as shown in the following reaction:

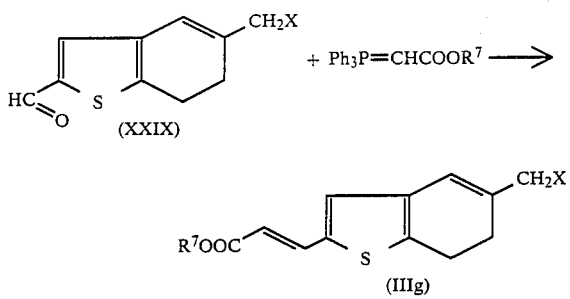

The corresponding compound having a double bond between the 6- and 7-positions and having the group —CH$_2$X at the 6-position may be prepared by the same reaction but starting with an analog of the compound of formula (XXIX) in which the double bond and the group —CH$_2$X are at those positions.

Similarly, tetrahydrothianaphthene derivatives having double bonds both between the 4- and 5-positions and between the 6- and 7-positions and having the group —CH$_2$X at either the 5-position or the 6-position may be prepared by first hydrogenating the compound of formula (XXIX) or its aforementioned analog before carrying out the Wittig reaction.

Method P

Compounds of formula (III) in which W represents a methylene group, the group —W—COOR$^3$ is at the 2-position, a double bond is present between the 4- and 5-positions, Z$^1$ represents a methylene group and the group —CH$_2$X (i.e. —Z$^1$—X) is at the 5-position, that is to say compounds of formula (IIIh), may be prepared as illustrated by the following reaction scheme:

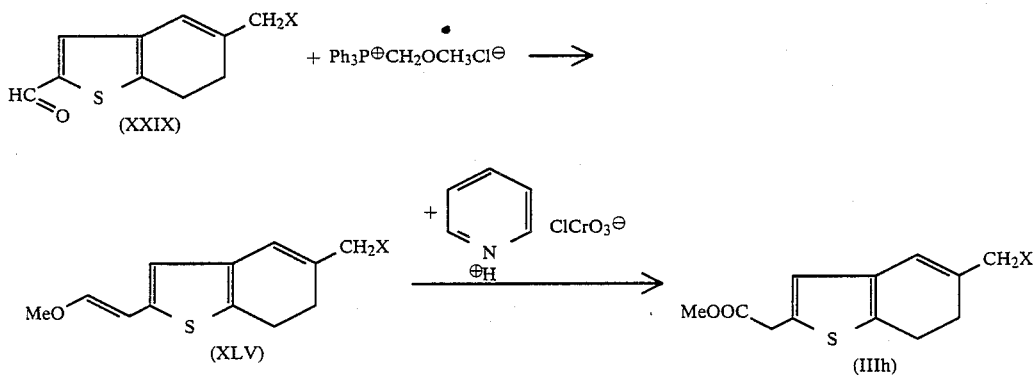

In the above formulae, X and Ph are as defined above.

In the first step of this reaction, the compound of formula (XXIX) is subjected to a Wittig reaction to form a double bond in the side chain of the 2-position and give the compound of formula (XLV). This is then oxidized, suitably with pyridinium chlorochromate, to give the desired compound of formula (IIIh).

Compounds corresponding to the compounds of formula (IIIh) but in which there is a double bond between the 6- and 7-positions and in which the group —CH$_2$X is at the 6-position may be prepared by the same sequence of reactions, but starting with an analog of the compound of formula (XXIX) in which the double bond is present between the 6- and 7-positions and the group —CH$_2$X is present at the 6-position.

Corresponding tetrahydrothianaphthene derivatives having single bonds both between the 4- and 5-positions and between the 6- and 7-positions and having the group —CH$_2$X at either the 5-position or the 6-position may be prepared by first halogenating the compound of formula (XXIX) or its aforementioned analog prior to carrying out the Wittig reaction and then the oxidation.

In all of the foregoing Methods G–P, starting materials in which R$^1$ and/or R$^2$ represents an alkyl group may be prepared by exactly the same methods but employing corresponding starting materials having one or more alkyl substituents at the appropriate position.

Where starting materials are prepared as esters, these can, if desired, be converted before use by conventional hydrolysis reactions to the free acid.

The compounds of the present invention may contain one or more asymmetric carbon atoms and thus can exist in the form of various optical isomers. If required, individual optical isomers may be prepared by employing specific isomers of the starting materials and/or by stereospecific synthesis techniques. Alternatively, if a mixture of isomers is prepared by any of the above reactions, the individual isomers can be obtained by conventional optical resolution techniques. Alternatively, a mixture of the isomers may be employed. Although all of the isomers are represented above by a single structural formula, the present invention envisages both the individual isolated isomers as well as mixtures thereof.

The compounds of the present invention have been found to have excellent ability to inhibit blood platelet aggregation and to inhibit the activity of TXA$_2$ synthetase, as a result of which they have excellent anti-thrombotic activity, as demonstrated by pharmacological tests, including those reported hereafter.

Thus, the compounds of the invention have shown 100% inhibition of collagen-induced platelet aggregation in rabbit platelet-rich plasma at concentrations of the order of 10$^{-5}$ g/ml and 50% inhibition of the biosynthesis of TXA$_2$ at molar concentrations of the order of 10$^{-8}$. On the other hand, the inhibitory activities against cyclooxygenase and prostacyclin synthetase are very weak, thus indicating that the compounds of the present invention are relatively inactive against other enzymes of metabolic importance, which is an advantage. In in vivo experimental systems, the compounds of the present invention have demonstrated, on oral administration, considerable preventive effect against mortality from thrombotic disorders in mice and rabbits induced by intravenous injection of arachidonic acid. These tests are all well recognized as providing good experimental models to demonstrate anticipated activity in human beings.

In particular, the lack of activity against cyclooxygenase and protacyclin synthetase demonstrate that the compounds of the invention do not inhibit the synthesis of other prostaglandin derivatives.

Accordingly, the compounds of the present invention are expected to be valuable for the therapy and prophylaxis of diseases and disorders caused by an imbalance in the blood level of $TXA_2$, for example inflammation, hypertension, thrombosis, cerebral haemorrhages and asthma, and are expected to be especially useful in the treatment or prophylaxis of thromboembolisms in mammals, including humans. For example, they are expected to be useful in the treatment and prophylaxis of myocardial infarction, cerebral vascular thrombosis and ischemic peripheral blood vessel diseases, as well as in the treatment and prophylaxis of postoperative thrombosis and to accelerate the dilation of transplated blood vessels after an operation.

The compounds of the invention may be administered by any suitable route, oral or parenteral, and may be formulated accordingly, for example: for oral administration as tablets, capsules, powders, granules or syrups; or, for parenteral administration, as suppositories or as injectible solutions or suspensions for subcutaneous or intravenous injection.

The compounds of the invention may be formulated with conventional pharmaceutical carriers or diluents or may be administered as such.

The amount of the compound of the invention to be administered will vary, depending upon the nature and severity of the disease or disorder to be treated, the age, body weight, symptoms and condition of the patient and the mode of administration. However, by way of guidance, the dose for an adult human being would be expected to be from 50 to 1800 mg per day, which is preferably administered in divided doses, e.g. about 2 or 3 times per day.

The preparation of certain compounds of the invention is further illustrated by the following Examples 1-45, whilst the preparation of certain of the starting materials used in these Examples is illustrated in the subsequent Preparations. The biological activity of the compounds of the invention is illustrated in Experiments 1 and 2. In the nuclear magnetic resonance spectra, tetramethylsilane was used as the internal standard in all Examples.

EXAMPLE 1

Methyl 4,5-dihydro-2-(1-imidazolyl)methylthianaphthene-6-carboxylate

1(a). 0.14 g of sodium borohydride was added to a solution of 0.75 g of methyl 2-formyl-4,5-dihydrothianaphthene-6-carboxylate in a mixture of 4 ml each of methanol and tetrahydrofuran at 3° C., and the mixture was stirred for 30 minutes. At the end of this time, the reaction mixture was concentrated by evaporation under reduced pressure. The residue was extracted with aqueous ethyl acetate, and the extract was washed with an aqueous solution of sodium chloride, dried over anhydrous sodium sulfate, filtered and evaporated to dryness under reduced pressure, to give 0.75 g of methyl 4,5-dihydro-2-hydroxymethylthianaphthene-6-carboxylate.

1(b). 0.73 ml of a solution of thionyl chloride in 10 ml of methylene chloride was added dropwise to a solution of 2.98 g of imidazole and 20 mg of 4-dimethylaminopyridine in 60 ml of methylene chloride, and the mixture was stirred for 30 minutes. A solution of 0.75 g of methyl 4,5-dihydro-2-hydroxymethylthianaphthene-6-carboxylate [prepared as described in step (a) above] in 10 ml of methylene chloride was added dropwise to the solution, and the reaction mixture was stirred overnight at room temperature. The reaction mixture was then concentrated by evaporation under reduced pressure. The residue was extracted with a mixture of a saturated aqueous solution of sodium bicarbonate and ethyl acetate. The extract was washed 5-6 times with water, dried over anhydrous sodium sulfate, filtered and concentrated by evaporation under reduced pressure. The resulting syrupy substance was purified by column chromatography through silica gel, eluted with a 50:1:1 by volume mixture of ethyl acetate, ethanol and triethylamine, to give 0.21 g of the title compound as an oily substance.

Nuclear Magnetic Resonance Spectrum ($CDCl_3$) δ ppm: 3.80 (3H, singlet); 5.22 (2H, singlet).

EXAMPLE 2

Sodium 4,5-dihydro-2-(1-imidazolyl)methylthianaphthene-6-carboxylate and its hydrate 0.21 g of methyl 4,5-dihydro-2-(1-imidazolyl)methyl-thianaphthene-6-carboxylate (prepared as described in Example 1) was hydrolyzed in a solution of sodium hydroxide in aqueous ethanol. The ethanol was distilled off under reduced pressure. The resulting aqueous solution was washed with diethyl ether and then evaporated to dryness. The resulting solid residue was reprecipitated from methanol-diethyl ether, to afford 0.12 g of the title compound as a pale yellow amorphous powder.

Infrared Absorption Spectrum (Nujol-trade markmull) $\nu_{max}cm^{-1}$: 1650, 1550.

Elemental analysis: Calculated for $C_{13}H_{11}N_2O_2SNa.H_2O$: C, 51.99%; H, 3.79%; N, 9.33%; S, 10.68%. Found: C, 52.11%; H, 3.78%; N, 9.43%; S, 10.25%.

The amorphous solid obtained as described above was recrystallized from 80% v/v aqueous methanol-acetone to give the corresponding anhydride as pale yellow needles (m.p. >300° C.).

Elemental Analysis: Calculated for $C_{13}H_{11}N_2O_2SNa$: C, 55.31%; H, 3.93%; N, 9.92%; S, 11.36%. Found: C, 55.53%; H, 3.96%; N, 10.08%; S, 11.24%.

EXAMPLE 3

Methyl 4,5-dihydro-2-[α-(1-imidazolyl)benzyl]thianaphthene-6-carboxylate 0.40 g of methyl 2-benzoyl-4,5-dihydrothianaphthene-6-carboxylate was reduced with sodium borohydride in the same manner as described in Example 1(a), and then an imidazolyl group was introduced by the method described in Example 1(b). The reaction mixture was then concentrated by evaporation under reduced pressure. The residue was extracted with a mixture of a saturated aqueous solution of sodium bicarbonate and ethyl acetate. The extract was washed 5-6 times with water, dried over anhydrous sodium sulfate, filtered and concentrated by evaporation under reduced pressure. The resulting crude oily substance thus obtained was subjected to column chromatography through sillica gel, using ethyl acetate as the eluent, to afford 0.21 g of the title compound.

Nuclear Magnetic Resonance Spectrum (CDCl$_3$) δ ppm: 3.79 (3H, singlet); 6.65 (2H, singlet).

EXAMPLE 4

Sodium 4,5-dihydro-2-[α-(1-imidazolyl)benzyl]thianaphthene-6-carboxylate trihydrate 0.21 g of methyl 4,5-dihydro-2-[α-(1-imidazolyl)benzyl]thianaphthene-6-carboxylate (prepared as described in Example 3) was hydrolyzed in a solution of sodium hydroxide in aqueous ethanol. The ethanol was then distilled off under reduced pressure. The resulting aqueous solution was washed with diethyl ether and then evaporated to dryness. The resulting powder was reprecipitated from ethanol-diethyl ether to afford 70 mg of the title compound as a colorless, amorphous powder.

Infrared Absorption Spectrum (Nujol mull) $\nu_{max}$cm$^{-1}$: 1690, 1460.

Elemental analysis: Calculated for $C_{19}H_{15}N_2O_2SNa \cdot 3H_2O$: C, 55.33%; H, 5.13%; N, 6.79%; S, 7.77%. Found: C, 55.23%; H, 4.85%; N, 7.05%; S, 7.79%.

EXAMPLE 5

Methyl 2-[2-(1-imidazolyl)ethyl]-4,5-dihydrothianaphthene-6-carboxylate

5(a) Methyl 2-[2-(1-imidazolyl)-1-oxoethyl]-4,5-dihydrothianaphthene-6-carboxylate A Friedel-Crafts reaction was carried out using 15.0 g of methyl 4,5-dihydrothianaphthene-6-carboxylate, 20.6 g of aluminum chloride and 8.3 ml of bromoacetyl chloride. The reaction mixture was then poured into ice-water and stirred for 1 hour. The mixture was then extracted with methylene chloride. The extract was washed with aqueous sodium chloride, dried over anhydrous sodium sulfate, filtered and then evaporated to dryness under reduced pressure, to obtain a crude crystalline substance containing methyl 2-(2-bromo-1-oxoethyl)-4,5-dihydrothianaphthene-6-carboxylate. The crude crystalline substance thus obtained was dissolved in a mixture of 300 ml of methanol and 150 ml of tetrahydrofuran. 18.4 g of imidazole were added to the resulting solution, and the mixture was heated under reflux for 2 hours. At the end of this time, the reaction mixture was concentrated by evaporation under reduced pressure. The residue was dissolved in ethyl acetate, and the resulting solution was washed in turn with a saturated aqueous solution of sodium bicarbonate and with an aqueous solution of sodium chloride. The solution was then filtered and concentrated by evaporation under reduced pressure. The resulting residue was subjected to silica gel column chromatography, using a 40:1:1 by volume mixture of ethyl acetate, ethanol and triethylamine as the eluent, to afford 20.16 g of the title compound as an oily substance.

Nuclear Magnetic Resonance Spectrum (CDCl$_3$) δ ppm: 3.85 (3H, singlet); 5.20 (2H, singlet).

5(b) Methyl 2-[2-(1-imidazolyl)-1-methylthio(thiocarbonyl)oxyethyl]-4,5-dihydrothianaphthene-6-carboxylate 2.01 g of methyl 2-[2-(1-imidazolyl)-1-oxoethyl]-4,5-dihydrothianaphthene-6-carboxylate [prepared as described in step (a) above] were reduced with sodium borohydride in the same manner as described in Example 1(a), to obtain 1.72 g of an alcohol. This was dissolved in tetrahydrofuran, 0.30 g of sodium hydride was added at 3° C. to the resulting solution, and the mixture was stirred at 50° C. for 1 hour. The mixture was then cooled by allowing it to stand at room temperature. 1.7 ml of carbon disulfide and 1.76 ml of methyl iodide were added in that order, and the mixture was stirred at room temperature for 20 minutes. At the end of this time, the reaction mixture was poured into a mixture of ice-water and 0.39 ml of glacial acetic acid and extracted with ethyl acetate. The extract was washed in turn with a saturated aqueous solution of sodium bicarbonate and with an aqueous solution of sodium chloride. The solution was then dried over anhydrous sodium sulfate and concentrated by evaporation under reduced pressure. The resulting residue was subjected to silica gel column chromatography, using an 8:1:1 by volume mixture of ethyl acetate, ethanol and triethylamine as eluent, to afford 1.03 g of the title compound as an oily substance.

Nuclear Magnetic Resonance Spectrum (CDCl$_3$) δ ppm: 2.40 (3H, singlet); 3.79 (3H, singlet).

5(c) Methyl 2-[2-(1-imidazolyl)ethyl]-4,5-dihydrothianaphthene-6-carboxylate 1.00 g of methyl 2-[2-(1-imidazolyl)-1-methylthio(thiocarbonyl)oxyethyl]-4,5-dihydrothianaphthene [prepared as described in step (b) above] was dissolved in a mixture of 15 ml of tetrahydrofuran and 10 ml of toluene. 10 ml of tributyltin hydride was added to the solution in the presence of a catalytic amount of azobisisobutyronitrile, and the mixture was heated under reflux for 1 day under an atmosphere of nitrogen. At the end of this time, the reaction mixture was condensed by distilling off the solvent under reduced pressure, and a solution of the residue in acetonitrile was washed with hexane. The acetonitrile was then removed by distillation under reduced pressure, and the residue was subjected to silica gel column chromatography using a 30:1:1 by volume mixture of ethyl acetate, ethanol and triethylamine as the eluent, to afford 0.51 g of the title compound as an oily substance.

Nuclear Magnetic Resonance Spectrum (CDCl$_3$) δ ppm: 3.16 (2H, triplet); 3.80 (2H, singlet); 4.19 (2H, triplet); 7.42 (1H, singlet).

EXAMPLE 6

Sodium 2-[2-(1-imidazolyl)ethyl]-4,5-dihydrothianaphthene-6-carboxylate 0.45 g of methyl 2-[2-(1-imidazolyl)ethyl]4,5-dihydrothianaphthene-6-carboxylate (prepared as described in Example 5) was hydrolyzed with sodium hydroxide in the same manner as described in Example 2, to obtain a solid, which was reprecipitated from methanol and diethyl ether, to afford 0.37 g of the title compound as a colorless, amorphous powder.

Infrared Absorption Spectrum (Nujol mull) $\nu_{max}cm^{-1}$: 1630, 1560.

Elemental analysis: Calculated for $C_{14}H_{13}N_2O_2SNa$: C, 56.75%; H, 4.42%; N, 9.45%; S, 10.82%. Found: C, 56.58%; H, 4.70%; N, 9.44%; S, 10.59%.

EXAMPLE 7

Methyl 4,5,6,7-tetrahydro-2-(1-imidazolyl)methylthianaphthene-6-carboxylate

Using the same procedure as described in Example 1, 0.20 g of the title compound was obtained as an oily substance from 0.34 g of 2-formyl-4,5,6,7-tetrahydrothianaphthene-6-carboxylate.

Nuclear Magnetic Resonance Spectrum (CDCl₃) δ ppm: 3.77 (3H, singlet); 5.20 (2H, singlet).

EXAMPLE 8

Sodium 4,5,6,7-tetrahydro-2-(1-imidazolyl)methylthianaphthene-6-carboxylate 0.30 g of methyl 4,5,6,7-tetrahydro-2-(1-imidazolyl)methylthianaphthene-6-carboxylate (prepared as described in Example 7) was hydrolyzed with sodium hydroxide in the same manner as described in Example 2, to obtain a solid, which was reprecipitated from ethanol-diethyl eyther, to afford 0.19 g of the title compound as a colorless, amorphous powder.

Infrared Absorption Spectrum (Nujol mull) $\nu_{max}cm^{-1}$: 1560.

Elemental analysis: Calculated for $C_{13}H_{13}N_2O_2SNa$: C, 54.92%; H, 46.09%; N, 9.85%; S, 11.28%. Found: C, 54.68%; H, 45.87%; N, 9.91%; S, 11.45%.

EXAMPLE 9

Methyl 2-[2-(1-imidazolyl)ethyl]-4,5,6,7-tetrahydrothianaphthene-6-carboxylate

9(a) Methyl 2-[2-(1-imidazolyl)-1-oxoethyl]-4,5,6,7-tetrahydrothianaphthene-6-carboxylate Using the same procedure as described in Example 5(a), 0.54 g of the title compound was obtained as an oily substance from 0.80 g of methyl 4,5,6,7-tetrahydrothianaphthene-6-carboxylate.

Nuclear Magnetic Resonance Spectrum (CDCL₃) δ ppm: 3.74 (3H, singlet); 5.22 (2H, singlet).

9(b) Methyl 2-[2-(1-imidazolyl)-1-methylthio(thiocarbonyl)oxyethyl]-4,5,6,7-tetrahydrothianaphthene-6-carboxylate Using the same procedure as described in Example 5(b), 0.42 g of the title compound was obtained as an oily substance from 0.54 g of the ketone prepared as described in step (a) above.

Nuclear Magnetic Resonance Spectrum (CDCl₃) δ ppm: 2.38 (3H, singlet); 3.77 (3H, singlet).

9(c) Methyl 2-[2-(1-imidazolyl)ethyl]-4,5,6,7-tetrahydrothianaphthene-6-carboxylate 0.41 g of the xanthate ester [prepared as described in step (b) above] was subjected to a free radical reduction with tributyltin hydride in the same manner as described in Example 5(c), to obtain 0.28 g of the title compound.

Nuclear Magnetic Resonance Spectrum (CDCl₃) δ ppm: 3.18 (2H, triplet); 3.79 (3H, singlet); 4.20 (2H, triplet).

EXAMPLE 10

2-[2-(1-Imidazolyl)ethyl]-4,5,6,7-tetrahydrothianaphthene-6-carboxylic acid hydrochloride A solution of 0.25 g of methyl 2-[2-(1-imidazolyl)ethyl]-4,5,6,7-tetrahydrothianaphthene-6-carboxylate (prepared as described in Example 9) in a mixture of 5 ml of concentrated hydrochloric acid and 5 ml of glacial acetic acid was heated under reflux for 4 hours. At the end of this time, the reaction mixture was evaporated to dryness by distilling off the solvent under reduced pressure, and the resulting solid residue was recrystallized from a mixture of ethanol and diethyl ether, to afford 0.19 g of the title compound as a colorless, amorphous powder.

Infrared Absorption Spectrum (Nujol mull) $\nu_{max}cm^{-1}$: 1720.

Elemental analysis: Calculated for $C_{14}H_{16}N_2O_2S \cdot HCl$: C, 53.76%; H, 5.48%; N, 8.96%; S, 10.25%; Cl, 11.33%. Found: C, 53.72%; H, 5.73%; N, 9.01%; S, 9.95%; Cl, 11.30%.

EXAMPLE 11

4,5,6,7-Tetrahydro-2-(1-imidazolyl)methyl-6-methoxycarbonylmethylidenethianaphthene Using the same procedure as described in Example 1, 0.39 g of the title compound was obtained as an oily substance from 1.50 g of 2-formyl-4,5,6,7-tetrahydro-6-methoxycarbonylmethylidenethianaphthene.

Nuclear Magnetic Resonance Spectrum (CDCl₃) δ ppm: 3.68 (3H, singlet); 5.20 (2H, singlet); 6.25 (1H, singlet); 6.73 (1H, singlet).

EXAMPLE 12

Sodium salt of 4,5,6,7-tetrahydro-2-(1-imidazolyl)methyl-6-carboxymethylidenethianaphthene 0.29 g of 4,5,6,7-tetrahydro-2-(1-imidazolyl)methyl-6-methoxycarbonylmethylidenethianaphthene (prepared as described in Example 11) was hydrolyzed with sodium hydroxide in the same manner as described in Example 2 to obtain a solid, which was reprecipitated from ethanol-diethyl ether, to afford 0.20 g of the title compound as a pale yellow, amorphous powder.

Infrared Absorption Spectrum (Nujol mull) $\nu_{max}cm^{-1}$: 1580.

Elemental analysis: Calculated for $C_{14}H_{13}N_2O_2SNa$: C, 56.75%; H, 4.42%; N, 9.45%; S, 10.82%. Found: C, 57.03%; H, 4.18%; N, 9.40%; S, 11.08%.

EXAMPLE 13

Methyl 4,5,6,7-tetrahydro-2-[(3-pyridyl)methyl]thianaphthene-6-carboxylate

13(a) Methyl 4,5-dihydro-2-[(hydroxy)(3-pyridyl)methyl]thianaphthene-6-carboxylate 12 ml of a 15% w/v solution of butyllithium in hexane were added to a solution of 2.17 ml of 3-bromopyridine in 40 ml of diethyl ether at −78° C. under an atmosphere of nitrogen, and the mixture was stirred for 30 minutes. A solution of 2.5 g of methyl 2-formyl-4,5-dihydrothianaphthene-6-carboxylate in a mixture of 20 ml each of diethyl ether and tetrahydrofuran was then added dropwise thereto. The mixxture was then warmed up to room temperature over a period of about one hour and then poured into an aqueous solution of ammonium chloride. The mixture was extracted with ethyl acetate, and the extract was washed with an aqueous solution of sodium chloride, dried over anhydrous sodium sulfate and concentrated by evaporation under reduced pressure. The residue was subjected to silica gel column chromatography, using ethyl acetate was the eluent, to afford 1.61 g of the title compound as an oily substance.

Nuclear Magnetic Resonance Spectrum (CDCl$_3$) δ ppm: 3.80 (3H, singlet); 5.94 (1H, singlet); 6.65 (1H, singlet).

13(b) Methyl 4,5,6,7-tetrahydro-2-[3-pyridyl)methyl]thianaphthene-6-carboxylate 1.0 g of methyl 4,5-dihydro-2-[(hydroxy)(3-pyridyl)methyl]thianaphthene-6-carboxylate [prepared as described in step (a) above] in solution in ethanol was reduced in the presence of 3.48 ml of a 1N aqueous solution of hydrochloric acid over 2.0 g of a 10% w/w palladium-on-carbon catalyst and in an atmosphere of hydrogen. When the reduction was complete, the reaction mixture was adjusted to a pH value of 8 by the addition of an aqueous solution of sodium bicarbonate. The mixture was then filtered, and the filtrate was concentrated by evaporation under reduced pressure. The resulting residue was dissolved in ethyl acetate, and the solution was washed with an aqueous solution sodium chloride. The solution was then dried over anhydrous sodium sulfate, filtered and concentrated by evaporation under reduced pressure. The resulting residue was purified by silica gel column chromatography, using a 1:2 by volume mixture of hexane and ethyl acetate as the eluent, to afford 0.15 g of the title compound as an oily substance.

Nuclear Magnetic Resonance Spectrum (CDCl$_3$) δ ppm: 3.71 (3H, singlet); 4.08 (2H, singlet); 6.44 (1H, singlet).

EXAMPLE 14

4,5,6,7-Tetrahydro-2-[(3-Pyridyl)methyl]thianaphthene-6-carboxylate hydrochloride 0.15 g of methyl 4,5,6,7-tetrahydro-2-[(3-pyridyl)methyl]thianaphthene-6-carboxylate (prepared as described in Example 13) was dissolved in a mixture of 2 ml each of concentrated hydrochloric acid and glacial acetic acid, and the mixture was heated under reflux for 9 hours. At the end of this time, the reaction mixture was evaporated to dryness under reduced pressure, and the resulting residue was recrystallized from ethanol-diethyl ether, to afford 0.12 g of the title compound as colorless needles, melting at 205°–208° C.

Elemental analysis: Calculated for C$_{15}$H$_{15}$NO$_2$S.HCl: C, 58.15%; H, 5.21%; N, 4.52%; S, 10.35%; Cl, 11.48%. Found: C, 57.89%; H, 5.45%; N, 4.50%; S, 10.41%; Cl, 11.55%.

EXAMPLE 15

Methyl 2-[2-(1-imidazolyl)vinylene]-4,5-dihydrothianaphthene-6-carboxylate 1.02 g of methyl 2-[2-(1-imidazolyl)-1-oxoethyl]4,5-dihydrothianaphthene-6-carboxylate [prepared as described in Example 5(a)] was reduced with sodium borohydride in the same manner as described in Example 1 to obtain 0.87 g of the corresponding alcohol. A solution of this alcohol in 100 ml of toluene was heated under reflux for 2 hours in the presence of 0.59 g of p-toluenesulfonic acid monohydrate. At the end of this time, the reaction mixture was poured into a saturated aqueous solution of sodium bicarbonate and extracted with ethyl acetate. The extract was washed with an aqueous solution of sodium chloride, dried over anhydrous sodium sulfate, filtered and concentrated by evaporation under reduced pressure. The resulting residue was subjected to silica gel column chromatography, using a 40:1:1 by volume mixture of ethyl acetate, ethanol and triethylamine as the eluent, to afford 0.58 of the title compound as an oily substance.

Nuclear Magnetic Resonance Spectrum (CDCl$_3$) δ ppm: 3.79 (3H, singlet);
6.5–7.3 (6H, multiplet); 7.75 (1H, singlet).

EXAMPLE 16

Sodium 2-[2-(1-imidazolyl)vinylene]-4,5-dihydrothianaphthene-6-carboxylate 0.38 g of methyl 2-[2-(1-imidazolyl)vinylene]-4,5-dihydrothianapthene-6-carboxylate (prepared as described in Example 15) was hydrolyzed with sodium hydroxide in the same manner as described in Example 2, and a solid product was reprecipitated from a mixture of ethanol and diethyl ether, to afford 0.29 g of the title compound as a colorless, amorphous powder.

Infrared Absorption Spectrum (Nujol mull) $\nu_{max}$cm$^{-1}$: 1635, 1560.

Elemental analysis: Calculated for C$_{14}$H$_{11}$N$_2$O$_2$SNa: C, 57.14%; H, 3.77%; N, 9.52%; S, 10.89%. Found: C, 56.89%; H, 3.88%, N, 9.56%; S, 11.21%.

EXAMPLE 17

6-[4,5,6,7-Tetrahydro-2-(1-imidazolyl)methylthianaphthene]carboxylic acid hydrochloride A solution of 2.90 g of methyl 4,5,6,7-tetrahydro-2-(1-imidazolyl)methylthianaphthene-6-carboxylate (prepared as described in Example 7) in 30 ml of concentrated hydrochloric acid and 30 ml of glacial acetic acid was heated under reflux for 3 hours. At the end of this time, the reaction mixture was evaporated to dryness under reduced pressure, and the residue was treated to give a crude crystalline substance, which was then recrystallized from 95% v/v aqueous ethanol-acetone to give 22.55 g of the title compound as colorless needles, melting at 197°–198° C.

Infrared Absorption Spectrum (KBr) $\nu_{max}$$^{cm-1}$: 1720.

Elemental Analysis: Calculated for C$_{13}$H$_{14}$N$_2$O$_2$S.HCl: C, 52.26%; H, 5.06%; N, 9.38%; S, 10.73%; Cl, 11.87%. Found: C, 52.15%; H, 5.09%; N, 9.31%; S, 10.63%; Cl, 11.77%.

EXAMPLE 18

Methyl 6,7-dihydro-2-[(1-imidazolyl)methyl]thianaphthene-5-carboxylate

A solution of 0.78 ml of thionyl chloride in 4 ml of methylene chloride was added to a solution of 2.91 g of imidazole in methylene chloride, and the mixture was stirred for 30 minutes. A solution of 0.96 g of methyl 6,7-dihydro-2-(hydroxymethyl)thianaphthene-5-carboxylate in 15 ml of methylene chloride was then added dropwise thereto. The reaction mixture was stirred for 15 hours at room temperature, after which time the solvent was removed by distillation under reduced pressure. The residue obtained was dissolved in ethyl acetate, and the solution was washed, in turn, with an aqueous solution of sodium bicarbonate and with an aqueous solution of sodium chloride. It was then dried over anhydrous sodium sulfate. The solvent was then removed by evaporation under reduced pressure, and the residue was subjected to silica gel column chromatography, using a 20:1:1 by volume mixture of ethyl acetate, ethanol and triethylamine as the eluent, to give 0.76 g of the title compound. This product was recrystallized from acetone-hexane to afford pale yellow needles, melting at 87.0°–89.0° C.

EXAMPLE 19

Sodium 5-{6,7-dihydro-2-[(1-imidazolyl)methyl]thianaphthene}carboxylate hemihydrate 0.13 g of methyl 6,7-dihydro-2-[(1-imidazolylmethyl]thianaphthene-5-carboxylate (prepared as described in Example 18) was hydrolysed with sodium hydroxide in ethanol by conventional means. The ethanol was distilled off under reduced pressure, and the residual aqueous phase was washed with diethyl ether and then evaporated to dryness under reduced pressure. The resulting product was recrystallized from methanol-acetone to afford 0.10 g of the title compound as pale green needles, not melting at 260° C.

Elemental analysis: Calculated for $C_{13}H_{11}N_2O_2SNa.\frac{1}{2}H_2O$: C, 53.60%; H, 4.15%; N, 9.62%; S, 11.01%. Found: C, 53.77%; H, 3.97%; N, 9.19%; S, 11.10%.

EXAMPLE 20

Methyl 4,5,6,7-tetrahydro-2-[(1-imidazolyl)methyl]thianaphthene-5-carboxylate 0.30 g of methyl 6,7-dihydro-2-[(1-imidazolyl)methyl]thianaphthene-5-carboxylate (prepared as described in Example 18) was catalytically hydrogenated in the presence of 1.0 g of 10% w/w palladium-on-carbon and 1.15 ml of 1N aqueous hydrochloric acid in a hydrogen atmosphere. At the end of this time, the reaction mixture was adjusted to a pH value of 8 by the addition of an aqueous solution of sodium bicarbonate; it was then filtered. The filtrate was concentrated by evaporation under reduced pressure, and the residue was dissolved in ethyl acetate. The resulting solution was washed with an aqueous solution of sodium chloride and dried over anhydrous sodium sulfate. It was then filtered and concentrated by evaporation under reduced pressure, to afford 0.12 g of the title compound as an oily substance.

Nuclear Magnetic Resonance Spectrum (CDCl$_3$) δ ppm: 3.70 (3H, singlet); 5.14 (2H, singlet); 6.65 (1H, singlet).

EXAMPLE 21

5-{4,5,6,7-tetrahydro-2-[(1-imidazolyl)methyl]thianaphthene}carboxylic acid hydrochloride ¼ hydrate A solution of 0.12 g of methyl 4,5,6,7-tetrahydro-2-[(1-imidazoly)methyl]thianaphthene-5-carboxylate (prepared as described in Example 20) in 3 ml of concentrated hydrochloric acid and 3 ml of glacial acetic acid was heated under reflux for 4 hours. At the end of this time, the reaction mixture was evaporated to dryness by distillation of the solvent under reduced pressure. The residue was recrystallized from a mixture of ethanol and diethyl ether, to afford 0.09 g of the title compound as colorless scaley crystals, melting at 213.0°–215.0° C.

Elemental analysis: Calculated for $C_{13}H_{14}N_2O_2S.HCl.\frac{1}{4}H_2O$: C, 51.48%; H, 5.15%; N, 9.23%; S, 10.57%; Cl, 11.69%. Found: C, 51.17%; H, 5.16%; N, 9.09%; S, 10.40%; Cl, 11.82%.

EXAMPLE 22

Methyl 6,7-dihydro-2-[α(1-imidazolyl)benzyl]thianaphthene-5-carboxylate

A solution of 1.22 ml of thionyl chloride in 10 ml of methylene chloride was added to a solution of 4.92 g of imidazole in 20 ml of methylene chloride and, after 30 minutes, a solution of 1.67 g of methyl 2-[(hydroxy)(phenyl)methyl]thianaphthene-5-carboxylate in 30 ml of methylene chloride was added dropwise thereto under a nitrogen atmosphere. After 10 minutes, the reaction mixture was concentrated and treated in the same manner as described in Example 18. The residue obtained was subjected to silica gel column chromatography, using ethyl acetate as the eluent, to afford 1.26 g of the title compound as a pale brown, oily substance.

Nuclear Magnetic Resonance Spectrum (CDCl$_3$) δ ppm: 3.77 (3H, singlet); 6.64 and 6.70 (each 1H, both singlets).

EXAMPLE 23

Sodium 5-{6,7-dihydro-2-[α(1-imidazolyl)benzyl]thianaphthene}carboxylate dihydrate Using the same procedure as described in Example 19, 0.15 g of methyl 6,7-dihydro-2-[(1-imidazoly)benzyl]thianaphthene-5-carboxylate (prepared as described in Example 22) was hydrolyzed with sodium hydroxide, and the product was reprecipitated from a mixture of ethanol and diethyl ether, to afford 0.09 g of the title compound as a colorless, amorphous powder.

Infrared Absorption Spectrum (Nujol mull) $\nu_{max}$ cm$^{-1}$: 1550.

Elemental analysis: Calculated for $C_{19}H_{15}N_2OSNa.2H_2O$: C, 57.86%; H, 4.86%; N, 7.10%; S, 8.13%. Found: C, 57.49%; H, 4.11%; N, 6.89%; 3, 8.01%.

EXAMPLE 24

Methyl 4,5,6,7-tetrahydro-2-[(3-pyridyl)methyl]thianaphthene-5-carboxylate

24(a) Methyl 6,7-dihydro-2-[(hydroxy)(3-pyridyl)methyl]thianaphthene-5-carboxylate 12 ml of a 15% w/v solution of butyllithium in hexane was added to a solution of 2.17 ml of 3-bromopyridine in 40 ml of diethyl ether at −78° C. under an atmosphere of nitrogen, and the mixture was stirred for 30 minutes. A solution of 2.5 g of methyl 2-formyl-6,7-dihydrothianaphthene-5-carboxylate in a mixture of 20 ml each of diethyl ether and tetrahydrofuran was added dropwise thereto. The reaction mixture was then warmed up to room temperature over a period of about one hour and poured into an aqueous solution of ammonium chloride. It was then extracted with ethyl acetate. The extract was washed with an aqueous solution of sodium chloride, dried over anhydrous sodium sulfate and concentrated by evaporation under reduced pressure. The residue was subjected to silica gel column chromatography, using ethyl acetate as the eluent, to afford 1.61 g of the title compound as a pale brown, oily substance.

Nuclear Magnetic Resonance Spectrum (CDCl$_3$) δ ppm: 3.74 (3H, singlet); 5.95 (1H, singlet). 6.67 (1H, singlet).

24(b) Methyl 4,5,6,7-tetrahydro-2-[(3-pyridyl)methyl]thianaphthene-5-carboxylate 1.0 g of methyl 6,7-dihydro-2-[(hydroxy)(3-pyridyl)methyl]thianaphthene-5-carboxylate [prepared as described in step (a) above] was catalytically reduced in the presence of 2 g of 10% w/w palladium-on-carbon and of 3.48 ml of a 1N solution of hydrochloric acid under an atmosphere of hydrogen. The reaction mixture was then treated as described in Example 20. The product was subjected to silica gel column chromatography, using a 1:2 by volume mixture of hexane and ethyl acetate as the eluent, to afford 0.12 g of the title compound as a pale brown, oily substance.

Nuclear Magnetic Resonance Spectrum (CDCl$_3$) δ ppm: 3.71 (3H, singlet); 4.03 (2H, singlet); 6.47 (1H, singlet).

EXAMPLE 25

5-{2-[(3-pyridyl)methyl]-4,5,6,7-tetrahydrothianaphthene}carboxylic acid hydrochloride ¼ hydrate A solution of 0.12 g of methyl 4,5,6,7-tetrahydro-2-[(3-pyridyl)methyl]thianaphthene-5-carboxylate [prepared as described in Example 24(a)] in a mixture of 2 ml each of concentrated hydrochloric acid and glacial acetic acid was heated under reflux for 10 hours. At the end of this time, the reaction mixture was evaporated to dryness. The residue obtained was recrystallized from a mixture of ethanol and diethyl ether, to afford 0.10 g of the title compound as colorless needles, melting at 227°–229° C.

Elemental analysis: Calculated for C$_{15}$H$_{15}$NO$_2$.HCl.¼ H$_2$O: C, 57.32%; H, 5.29%; N, 4.46%; S, 10.20%; Cl, 11.28%. Found: C, 57.70%; H, 5.38%; N. 4.23%; S, 10.03%; Cl, 11.50%.

EXAMPLE 26

Methyl 2-[2-(1-imidazolyl)ethyl]-6,7-dihydrothianaphthene-5-carboxylate

A solution of 200 mg of imidazole in 4 ml of dimethylformamide was added dropwise to a suspension of 70 mg of sodium hydride (as a 55% w/w suspension in mineral oil) in 2 ml of dimethylformamide at room temperature under an atmosphere of nitrogen. After 15 minutes, a solution of 0.19 g of methyl 2-(2-methanesulfonyloxyethyl)-6,7-dihydrothianaphthene-5-carboxylate in 4 ml of dimethylformamide was added dropwise thereto, and the mixture was stirred at room temperature for one hour. At the end of this time, the reaction mixture was poured into ice-water and stirred for 1 hour. It was then extracted with ethyl acetate. The extract was washed well with water, dried over anhydrous sodium sulfate, filtered and concentrated by evaporation under reduced pressure. The resulting residue was subjected to silica gel column chromatography, using a 10:1:1 by volume mixture of ethyl acetate, ethanol and triethylamine as the eluent, to afford 90 mg of the title compound as a pale brown, oily substance.

Nuclear Magnetic Resonance Spectrum (CDCl$_3$) δ ppm: 3.80 (3H, singlet); 6.56 (1H, singlet).

EXAMPLE 27

Sodium 5-2-[2-(1-imidazolyl)ethyl]-6.7-dihydrothianaphthene carboxylate

Using the same procedure as described in Example 19, 30 g mg of methyl 2-[2-(1-imidazolyl)ethyl]-6,7-dihydrothianaphthene-5-carboxylate (prepared as described in Example 26) were hydrolyzed with sodium hydroxide, and the product was recrystallized from a mixture of ethanol and diethyl ether, to afford 20 mg of the title compound as colorless needles, melting at 180°–183° C. (with decomposition).

EXAMPLE 28

4,5,6,7-Tetrahydro-2-[(1-imidazoyl)methyl]-5-methoxycarbonylmethylidenethianaphthene Using the same procedure as described in Example 18, 0.29 g of the title compound was obtained as a pale brown, oily substance from 1.24 g of 4,5,6,7-tetrahydro-2-hydroxymethyl-5-methoxycarbonylmethylidenethianaphthene.

Nuclear Magnetic Resonance Spectrum (CDCl$_3$) δ ppm: 3.71 (3H, singlet); 5.16 (2H, singlet); 6.24 (1H, singlet); 6.70 (1H, singlet).

EXAMPLE 29

Sodium salt of [2-(1-imidazolyl)methyl]-5-carboxymethylidenethianaphthene

Using the same procedure as described in Example 19, 0.29 g of 4,5,6,7-tetrahydro-2-[(1-imidazolyl)methyl]-5-methoxycarbonylmethylidenethianaphthene (prepared as described in Example 28) was hydrolyzed with sodium hydroxide, and the product was recrystallized from a mixture of ethanol and diethyl ether, to afford 0.20 g of the title compound as a pale yellow powder, melting at 233°–235° C. (with decomposition).

EXAMPLE 30

Methyl 2-[1-(1-(1-imidazolyl)-2,2-dimethylpropyl]-6,7-dihydrothianaphthene-5-carboxylate Using the same procedure as described in Example 22, 0.95 g of the title compound was obtained as a pale brown oily substance from 1.05 g of methyl 2-(2,2-dimethyl-1-hydroxypropyl)-6,7-dihydrothianaphthene-5-carboxylate.

Nuclear Magnetic Resonance Spectrum (CDCl$_3$) δ ppm: 1.06 (9H, singlet); 3.80 (3H, singlet); 6.91 (1H, singlet).

EXAMPLE 31

Sodium 5-{6,7-dihydro-2-[1-(1-imidazolyl)-2,2-dimethylpropyl]-thianaphthene}carboxylate 3/2 hydrate Using the same procedure as described in Example 19, 0.95 g of methyl 2-[1-(1-imidazolyl)-2,2-dimethylpropyl]-6,7-dihydrothianaphthene-5-carboxylate was hydrolyzed, and the product was reprecipitated from a mixture of methanol and diethyl ether, to afford 0.71 g of the title compound as a colorless, amorphous powder.

Infrared Absorption Spectrum (Nujol mull) ν$_{max}$cm$^{-1}$: 1620, 1560.

Elemental analysis: Calculated for C$_{17}$H$_{19}$N$_2$O$_2$SNa.3/2H$_2$O: C, 55.88%; H, 6.07%; N, 7.67%; S, 8.77%. Found: C, 55.56%; H, 5.76%; N, 7.24%; S, 8.62%.

EXAMPLE 32

Methyl 6,7-dihydro-2-[(cyclohexyl)(1-imidazolyl)methyl]-thianaphthene-5-carboxylate Using the same procedure as described in Example 22, 0.41 g of the title compound was obtained as a pale brown, oily substance from 1.42 g of methyl 6,7-dihydro-2-[(cyclohexyl)(hydroxy)methyl]thianaphthene-5-carboxylate (prepared as described in Preparation 25).

Nuclear Magnetic Resonance Spectrum (CDCl$_3$) δ ppm: 3.77 (3H, singlet).

EXAMPLE 33

Sodium 5-{6,7-dihydro-2-[(cyclohexyl)(1-imidazolyl)methyl]-thianaphthene}carboxylate 3/2 hydrate Using the same procedure as described in Example 19, 0.41 g of methyl 6,7-dihydro-2-[(cyclohexyl)(1-imidazolyl)methyl]thianaphthene-5-carboxylate (prepared as described in Example 32) was hydrolyzed, and the product was reprecipitated from a mixture of methanol and diethyl ether, to afford 0.25 g of the title compound as a colorless, amorphous powder.

Infrared Absorption Spectrum (Nujol mull) ν$_{max}$cm$^{-1}$: 1625, 1560.

Elemental analysis: Calculated for C$_{19}$H$_{21}$N$_2$O$_2$SNa.3/2H$_2$O: C, 58.30%; H, 6.18%; N, 7.16%; S, 8.19%. Found: C, 58.39%; H, 6.19%; N, 6.92%; S, 8.31%.

EXAMPLE 34

Methyl 4,5,6,7-tetrahydro-2-[(cyclohexyl)(1-imidazolyl)methyl]thianaphthene-5-carboxylate Using the same procedure as described in Example 22, 0.39 g of the title compound was obtained as a pale brown, oily substance from 0.52 g of methyl 4,5,6,7-tetrahydro-2-[(cyclohexyl)(hydroxy)methyl]thianaphthenecarboxylate [prepared in a manner similar to that described in Example 24(a), but employing methyl 2-formyl-6,7-dihydrothianaphthene-5-carboxylate as the starting material].

Nuclear Magnetic Resonance Spectrum (CDCl$_3$) δ ppm: 3.70 (3H, singlet); 6.63 (1H, singlet).

EXAMPLE 35

5-{4,5,6,7-Tetrahydro-2-[(cyclohexyl)(1-imidazolyl)methyl]thianaphthene}carboxylic acid hydrochloride hydrate Using the same procedure as described in Example 21, 0.38 g of methyl 4,5,6,7-tetrahydro-2-[(cyclohexyl)(1-imidazolyl)methyl]thianaphthene-5-carboxylate was hydrolyzed, and the product was recrystallized from a mixture of methanol and diethyl ether, to afford 0.19 g of the title compound as colorless needless, melting at 202°–204° C.

Elemental analysis: Calculated for C$_{19}$H$_{24}$N$_2$O$_2$S.HCl.H$_2$O: C, 57.20%; H, 6.82%; N, 7.02%; S, 8.05%; Cl, 8.89%. Found: C, 56.77%; H, 6.69%; N, 7.45%; S, 8.25%; Cl, 9.10%.

EXAMPLE 36

Methyl 5-(1-imidazolyl)methyl-4,5,6,7-tetrahydrothianaphthene-2-carboxylate

A solution of 0.35 g of imidazole in 10 ml of dimethylformamide was added dropwise at room temperature to a suspension of 0.12 g of sodium hydride (as a 55% w/w suspension in mineral oil) in 10 ml of dimethylformamide under an atmosphere of nitrogen. After 30 minutes, a solution of 0.78 g of methyl 5-methanesulfonyloxymethyl-4,5,6,7-tetrahydrothianaphthene-2-carboxylate (prepared as described in Preparation 46) in 20 ml of dimethylformamide was added dropwise thereto, and the mixture was allowed to react for 2 hours whilst heating at 50° C. At the end of this time, the reaction mixture was poured into ice-water containing 0.17 ml of glacial acetic acid. The mixture was then adjusted to a pH value of 8 by the addition of an aqueous solution of sodium bicarbonate and extracted with ethyl acetate. The extract was washed with an aqueous solution of sodium chloride, dried over anhydrous sodium sulfate, filtered and concentrated by evaporation under reduced pressure. The resulting residue was subjected to silica gel column chromatography, eluted with a 20:1:1 by volume mixture of ethyl acetate, ethanol and triethylamine), to afford 0.49 g of the title compound as an oily substance Nuclear Magnetic Resonance Spectrum (CDCl$_3$) δ ppm: 3.85 (3H, singlet); 3.95 (2H, doublet, J=6.0 Hz); 6.85–7.6 (4H, multiplet).

EXAMPLE 37

2-[5-(1-Imidazolyl)methyl-4,5,6,7-tetrahydrothianaphthene]carboxylic acid hydrochloride 0.47 g of methyl 5-(1-imidazolyl-methyl)-4,5,6,7-tetrahydrothianaphthene-2-carboxylate (prepared as described in Example 36) was dissolved in a mixture of 5 ml each of glacial acetic acid and concentrated hydrochloric acid, and the mixture was heated under reflux for 6 hours. At the end of this time, the reaction mixture was evaporated to dryness under reduced pressure, and the resulting residue was reprecipitated from a mixture of isopropyl alcohol and diethyl ether, to afford 0.47 g of the title compound as a colorless, amorphous powder.

Infrared Absorption Spectrum (KBr) $\nu_{max}$cm$^{-1}$: 1680.

Elemental analysis: Calculated for $C_{13}H_{14}N_2O_2S\cdot HCl$: C, 52.26%, H, 5.06%; N, 9.38%; S, 10.73%; Cl, 11.87%. Found: C, 52.38%; H, 5.13%; N, 9.16%; S, 10.55%; Cl, 12.01%.

EXAMPLE 38

Methyl 5-(1-imidazolyl)methyl-6,7-dihydrothianaphthene-2-carboxylate

Using the same procedure as described in Example 36, 0.39 g of the title compound was obtained as an oily substance from 0.63 g of methyl 5-methanesulfonyloxymethyl-6,7-dihydrothianaphthene-2-carboxylate (prepared as described in Preparation 34).

Nuclear Magnetic Resonance Spectrum (CDCl$_3$) δ ppm: 3.88 (3H, singlet); 4.63 (2H, singlet); 6.5–7.6 (5H, multiplet).

EXAMPLE 39

2-[5-(1-Imidazolyl)methyl-6,7-dihydrothianaphthene]-carboxylic acid hydrochloride Using the same procedure as described in Example 37, 0.27 g of the title compound was obtained as a colorless, amorphous powder from 0.31 g of methyl 5-(1-imidazolyl)methyl-6,7-dihydrothianaphthene-2-carboxylate (prepared as described in Example 38).

Infrared Absorption Spectrum (KBr) $\nu_{max}$cm$^{-1}$: 1690.

Elemental analysis: Calculated for $C_{13}H_{12}N_2O_2S\cdot HCl$: C, 52.61%; H, 4.42%; N, 9.44%; S, 10.80%; Cl, 11.95%. Found: C, 52.77%; H, 4.44%; N, 9.20%; S, 11.03%; Cl, 12.01%.

EXAMPLE 40

Methyl 6-(1-imidazolyl)methyl-4,5,6,7-tetrahydrothianaphthene-2-carboxylate

Using the same procedure as described in Example 36, 0.87 g of the title compound was obtained as a colorless, amorphous powder from 1.00 g of methyl 6-methanesulfonyloxymethyl-4,5,6,7-tetrahydrothianaphthene-2-carboxylate (prepared as described in Preparation 38).

Nuclear Magnetic Resonance Spectrum (CDCl$_3$) δ ppm: 3.83 (3H, singlet); 3.96 (2H, doublet, J=6.0 Hz); 6.9–7.6 (4H, multiplet).

EXAMPLE 41

2-[6-(1-Imidazolyl)methyl-4,5,6,7-tetrahydrothianaphthene]carboxylic acid hydrochloride Using the same procedure as described in Example 37, 0.51 g of the title compound was obtained as a colorless, amorphous powder from 0.74 g of methyl 6-(1-imidazolyl)methyl-4,5,6,7-tetrahydrothianaphthene-2-carboxylate (prepared as described in Example 40).

Infrared Absorption Spectrum (KBr) $\nu_{max}$cm$^{-1}$: 1685.

Elemental analysis: Calculated for $C_{13}H_{14}N_2O_2S\cdot HCl$: C, 52.26%; H, 5.06%; N, 9.38%; S, 10.73%; Cl, 11.87%. Found: C, 52.03%; H, 4.99%; N, 9.53%; S, 10.71%; Cl, 11.72%.

EXAMPLE 42

Methyl 6-(1-imidazolyl)methyl-4,5-dihydrothianaphthene-2-carboxylate

Using the same procedure as described in Example 36, 0.29 g of the title compound was obtained as a colorless, amorphous powder from 0.35 g of methyl 6-methanesulfonyloxymethyl-4,5-dihydrothianaphthene-2-carboxylate (prepared as described in Preparation 42).

Nuclear Magnetic Resonance Spectrum (CDCl$_3$) δ ppm: 3.84 (3H, singlet); 4.68 (2H, singlet); 6.5–7.6 (5H, multiplet).

EXAMPLE 43

2-[6-(1-Imidazolyl)methyl-4,5-dihydrothianaphthene]-carboxylic acid hydrochloride Using the same procedure as described in Example 37, 0.23 g of the title compound was obtained as a colorless, amorphous powder from 0.29 g of methyl 6-(1-imidazolyl)methyl-4,5-dihydrothianaphthene-2-carboxylate (prepared as described in Example 42).

Infrared Absorption Spectrum (KBr) $\nu_{max}$cm$^{-1}$: 1690.

Elemental analysis: Calculated for $C_{13}H_{12}N_2O_2S\cdot HCl$: C, 52.61%; H, 4.42%; N, 9.44%; S, 10.80%; Cl, 11.95%. Found: C, 52.40%; H, 4.32%; N, 9.60%; S, 10.59%; Cl, 11.88%.

EXAMPLE 44

Methyl 5-[2-(1-imidazolyl)ethyl]-4,5,6,7-tetrahydrothianaphthene-2-carboxylate Using the same procedure as described in Example 36, 1.28 g of the title compound was obtained as an oily substance from 1.50 g of methyl 5-methanesulfonyloxymethyl-4,5,6,7-tetrahydrothianaphthene-2-carboxylate (prepared as described in Preparation 30).

Nuclear Magnetic Resonance Spectrum (CDCl$_3$) δ ppm: 3.90 (3H, singlet); 4.05 (2H, triplet, J=6.5 Hz); 6.9–7.6 (4H, multiplet).

EXAMPLE 45

2-{5-[2-(1-Imidazolyl)ethyl]-4,5,6,7-tetrahydrothianaphthene}carboxylic acid hydrochloride Using the same procedure as described in Example 37, 0.27 g of the title compound was obtained as a colorless, amorphous powder from 1.00 g of methyl 5-[2-(1-imidazolyl)ethyl]-4,5,6,7-tetrahydrothianaphthene-2-carboxylate (prepared as described in Example 44).

Infrared Absorption Spectrum (KBr) $\nu_{max}$cm$^{-1}$: 1690

Elemental analysis: Calculated for $C_{14}H_{16}N_2O_2S.HCl$: C, 53.76%; H, 5.48%; N, 8.96%; S, 10.25%; Cl, 11.33%. Found: C, 53.70%; H, 5.51%; N, 9.13%; S, 10.39%; Cl, 11.27%.

PREPARATION 1

Methyl 4,5-dihydrothianaphthene-6-carboxylate

A solution of 20 g of 4,5,6,7-tetrahydro-7-ketothianaphthene in dimethylformamide was added dropwise to a suspension of 6.31 g of sodium hydride (as a 55% w/w suspension in mineral oil) in 100 ml of dimethylformamide at room temperature, and the mixture was stirred for 10 minutes. 33 ml of dimethyl carbonate was then added dropwise to the reaction mixture at 5° C., and the reaction mixture was stirred for 90 minutes. It was then poured into a mixture of ice-water and 8.7 ml of glacial acetic acid and filtered. The precipitate was collected, to give 31.6 g of a crude product containing methyl 4,5,6,7-tetrahydro-4-oxothianaphthene-6-carboxylate. A solution of this crude product in a mixture of 100 ml each of tetrahydrofuran and methanol was cooled to $-15°$ C., and 4.98 g of sodium borohydride was added thereto over a period of one hour. At the end of this time, the reaction mixture was concentrated by evaporation under reduced pressure. The residue was extracted with a mixture of a saturated aqueous solution of sodium bicarbonate and ethyl acetate. The extract was washed 5-6 times with water, dried over anhydrous sodium sulfate, filtered and concentrated by evaporation under reduced pressure. The resulting residue was dissolved in 500 ml of benzene, 2.5 g of p-toluenesulfonic acid monohydrate was added to the solution, and the mixture was subjected to azeotropic distillation by heating for 30 minutes to remove the water produced. At the end of this time, the reaction mixture was poured into a saturated aqueous solution of sodium bicarbonate and extracted with ethyl acetate. The extract was washed with an aqueous solution of sodium chloride, filtered and concentrated by evaporation under reduced pressure. The product was subjected to silica gel column chromatography, using a 1:1 by volume mixture of hexane and ethyl acetate as the eluent, to afford 20.1 g of the title compound as an oily substance.

Nuclear Magnetic Resonance Spectrum (CDCl$_3$) δ ppm: 3.80 (3H, singlet); 6.86 and 7.29 (each 1H, both doublets, J=5.0 Hz); 7.54 (1H, singlet).

PREPARATION 2

Methyl 2-formyl-4,5-dihydrothianaphthene-6-carboxylate 30 ml of a solution of 7.5 g of 4,5-dihydrothianaphthene-6-carboxylate were added dropwise to a suspension of 10.3 g of aluminum chloride in 50 ml of methylene chloride at $-10°$ C. in an atmosphere of nitrogen. After 10 minutes, a solution of 5.24 ml of dichloromethyl methyl ether in 30 ml of methylene chloride was added dropwise thereto over a period of one hour, and the reaction mixture was concentrated by evaporation under reduced pressure. The residue was dissolved in ethyl acetate, and the resulting solution was then washed in turn with a saturated aqueous solution of sodium bicarbonate and with an aqueous solution of sodium chloride. It was then dried over anhydrous sodium sulfate, filtered and concentrated by evaporation under reduced pressure. The residue was subjected to silica gel column chromatography, using a 2:1 by volume mixture of hexane and ethyl acetate as the eluent, to afford 8.21 g of the title compound as an oily substance.

Nuclear Magnetic Resonance Spectrum (CDCl$_3$) δ ppm: 3.83 (3H, singlet); 7.50 and 7.57 (each 1H, both singlets); 9.86 (1H, singlet).

PREPARATION 3

Methyl 2-benzoyl-4,5-dihydrothianaphthene-6-carboxylate

Using the same procedure as described in Preparation 2, 1.65 g of the title compound was obtained as an oily substance from 1.78 g of aluminum chloride, 1.17 ml of benzoyl chloride and 1.30 g of methyl 4,5-dihydrothianaphthene-6-carboxylate.

Nuclear Magnetic Resonance Spectrum (CDCl$_3$) δ ppm: 3.81 (3H, singlet).

PREPARATION 4

Methyl 4,5,6,7-tetrahydrothianaphthene-6-carboxylate 1.63 g of methyl 4,5-dihydrothianaphthene-6-carboxylate was subjected to catalytic reduction in the presence of 1.6 g of 10% w/w palladium-on-carbon in an atmosphere of hydrogen whilst shaking the solution for 4 hours. At the end of this time, the reaction mixture was evaporated to dryness under reduced pressure, and the residue was subjected to silica gel column chromatography using a 10:1 by volume mixture of hexane and ethyl acetate as the eluent, to afford 1.31 g of the title compound as an oily substance.

Nuclear Magnetic Resonance Spectrum (CDCl$_3$) δ ppm: 3.73 (3H, singlet); 6.75 and 7.08 (each 2H, both doublets, J=5.0 Hz).

PREPARATION 5

Methyl 2-formyl-4,5,6,7-tetrahydrothianaphthene-6-carboxylate

Using the same procedure as described in Preparation 2, 0.3 g of the title compound was obtained as an oily substance from 0.50 g of methyl 4,5,6,7-tetrahydrothianaphthene-6-carboxylate (prepared as described in Preparation 4).

Nuclear Magnetic Resonance Spectrum (CDCl$_3$) δ ppm: 3.73 (3H, singlet); 7.45 (1H, singlet); 9.83 (1H, singlet).

PREPARATION 6

4,5,6,7-Tetrahydro-6-methoxycarbonylmethylidenethianaphthene

A solution of 9.57 g of 4,5,6,7-tetrahydro-7-ketothianaphthene in 30 ml of dimethylformamide was added dropwise to a suspension of 3.29 g of sodium hydride (as a 55% w/w suspension in mineral oil) in 30 ml of dimethylformamide in a nitrogen atmosphere. The mixture was cooled to 5° C., 16 ml of dimethyl carbonate was added dropwise thereto and the mixture was stirred at room temperature for one hour. A solution of 6.6 ml of methyl bromoacetate in 10 ml of dimethylformamide was then added, and the mixture was stirred at room temperature for one hour. At the end of this time, the reaction mixture was poured into ice-water and extracted with ethyl acetate. The extract was washed with an aqueous solution of sodium chloride and concentrated by evaporation under reduced pressure. The residue was dissolved in ethyl acetate, and the resulting solution was washed in turn with water, with a saturated aqueous solution of sodium bicarbonate and with an aqueous solution of sodium chloride. The washed solution was then dried over anhydrous sodium sulfate, filtered and concentrated by evaporation under reduced pressure. The residue was dissolved in a mixture of 200 ml each of concentrated hydrochloric acid and glacial acetic acid, and the solution was heated under reflux for 3 hours. The reaction mixture was then evaporated to dryness under reduced pressure, the residue was dissolved in 500 ml of methanol and 2 ml of concentrated sulfuric acid, and the mixture was heated again under reflux for 2 hours. At the end of this time, the product was concentrated by evaporation under reduced pressure. The residue was extracted with a mixture of a saturated aqueous solution of sodium bicarbonate and ethyl acetate. The extract was washed 5-6 times with water, dried over anhydrous sodium sulfate, filtered and concentrated by evaporation under reduced pressure. The resulting residue was subjected to silica gel column chromatography, using a 2:1 by volume mixture of hexane and ethyl acetate as the eluent, to afford 10.13 g of 4,5,6,7-tetrahydro-7-keto-6-methoxycarbonylmethylthianaphthene as an oily substance.

2.0 g of sodium borohydride were added to a solution of 10.13 g of the ketone thus prepared in 200 ml of methanol, and the mixture was stirred at room temperature for 30 minutes. At the end of this time, the reaction mixture was concentrated by evaporation under reduced pressure. The residue was extracted with a mixture of a saturated aqueous solution of sodium bicarbonate and ethyl acetate. The extract was washed 5-6 times with water, dried over anhydrous sodium sulfate, filtered and concentrated by evaporation under reduced pressure. The resulting residue was acetylated with 20 ml of acetic anhydride in 40 ml of pyridine. 0.7 g of p-toluenesulfonic acid monohydrate was added to a solution of the acetylated product in 250 ml of toluene, and the mixture was heated under reflux for 30 minutes. At the end of this time, the product was poured into a saturated aqueous solution of sodium bicarbonate and extracted with ethyl acetate. The extract was washed with an aqueous solution of sodium chloride, filtered and concentrated by evaporation under reduced pressure. The residue was subjected to silica gel column chromatography, using a 5:1 by volume mixture of hexane and ethyl acetate as eluent, to afford 5.50 g of the title compound as an oily substance.

Nuclear Magnetic Resonance Spectrum (CDCl$_3$) δ ppm: 3.65 (3H, singlet); 6.34 (1H, singlet).

PREPARATION 7

2-Formyl-4,5,6,7-tetrahydro-6-methoxycarbonylmethylidenethianaphthene

Using the same procedure as described in Preparation 2, 1.50 g of the title compound was obtained as an oily substance from 2.50 g of 4,5,6,7-tetrahydro-6-methoxycarbonylmethylidenethianaphthene (prepared as described in Preparation 6).

Nuclear Magnetic Resonance Spectrum (CDCl$_3$) δ ppm: 3.72 (3H, singlet); 6.33 (1H, singlet); 7.40 (1H, singlet); 9.81 (1H, singlet).

PREPARATION 8

Ethyl 6-(4,5-dihydrothianaphthene)carboxylate

8(a). A solution of 57 ml of tin tetrachloride in 600 ml of methylene chloride was cooled at −35° C., and then a solution of 60 g of ethyl 4-(3-thienyl)butyrate in 600 ml of methylene chloride was added dropwise under a nitrogen atmosphere over a period of one hour. 20 minutes after the dropwise addition was complete, a solution of 35 ml of dichloromethyl methyl ether in 600 ml of methylene chloride was added dropwise to the resulting mixture over a period of one hour, while maintaining the mixture at a temperature of −35° C., and stirring was continued for a further one hour. At the end of this time, the reaction mixture was treated in a conventional manner to give a crude syrupy substance containing ethyl 4-[3-(2-formyl)thienyl]butyrate.

8(b). 18.5 ml of ethanol were added dropwise to a suspension of 13.86 g of sodium hydride (as a 55% w//w suspension in mineral oil) in 500 ml of toluene under a nitrogen atmosphere at room temperature, and the resulting mixture was then heated to 80° C. A solution of the syrupy substance [obtained as described in step (a) above] in 250 ml of toluene was added all at once and the resulting mixture was allowed to cool at room temperature.

When the reaction mixture was cool, it was treated in a conventional manner to give a syrupy substance, which was then distilled under reduced pressure to give 32.80 g of the title compound boiling at 125°–128° C./2 mmHg (266 Pa).

Nuclear Magnetic Resonance Spectrum (CDCl$_3$) δ ppm: 1.31 (triplet, 7 Hz); 4.24 (7 Hz, quartet); 6.89 and 7.29 (each doublet, 5 Hz); 7.54 (singlet).

PREPARATION 9

Methyl 6,7-dihydrothianaphthene-5-carboxylate

A solution of 20 g of 4,5,6,7-tetrahydro-4-ketothianaphthene in dimethylformamide was added dropwise at room temperature to a suspension of 6.31 g of sodium hydride (as a 55% w/w suspension in mineral oil) in 100 ml of dimethylformamide, and the mixture was stirred for 10 minutes. 33 ml of dimethyl carbonate were added dropwise at 5° C. to the above reaction mixture, and the mixture was then stirred for 90 minutes. The reaction mixture was then poured into a mixture of ice-water and 8.7 ml of glacial acetic acid, and the mixture was filtered to obtain 31.6 g of a crude product containing methyl 4,5,6,7-tetrahydro-4-ketothianaphthene-5-carboxylate. A solution of the crude product in a mixture of 100 ml each of tetrahydrofuran and methanol was cooled to −15° C., and 4.98 g of sodium borohydride was added thereto over a period of one hour. At the end of this time, the reaction mixture was concentrated by evaporation under reduced pressure. The residue was dissolved in ethyl acetate, and the resulting solution was washed with an aqueous solution of sodium chloride, dried over anhydrous sodium sulfate, filtered and then concentrated by evaporation under reduced pressure. The residue was then dissolved in 500 ml of benzene. 2.5 g of p-toluenesulfonic acid monohydrate was added thereto, and the mixture was subjected to azeotropic distillation by heating for 30 minutes to remove the water produced. At the end of this time, the reaction mixture was poured into a saturated aqueous solution of sodium bicarbonate and extracted with ethyl acetate. The extract was washed with an aqueous solution of sodium chloride, dried over anhydrous sodium sulfate, filtered and then concentrated by evaporation under reduced pressure. The resulting residue was subjected to silica gel column chromatography, using a 1:1 by volume mixture of hexane and ethyl acetate as the eluent, to afford 20.1 g of the title compound as an oily substance.

Nuclear Magnetic Resonance Spectrum (CDCl$_3$) δ ppm: 3.78 (3H, singlet); 6.93 and 7.08 (each 1H, both doublets, J=5.0 Hz); 7.52 (1H, singlet).

PREPARATION 10

Methyl 2-formyl-6,7-dihydrothianaphthene-5-carboxylate

A solution of 7.5 g of methyl 6,7-dihydrothianaphthene-5-carboxylate (prepared as described in Preparation 9) in 30 ml of methylene chloride was added dropwise at −10° C. to a suspension of 10.3 g of aluminum chloride in 50 ml of methylene chloride under an atmosphere of nitrogen. After 10 minutes, a solution of 5.24 ml of dichloromethyl methyl ether in 30 ml of methylene chloride was added dropwise thereto over a period of one hour, and the reaction mixture was poured into ice-water and stirred for 1 hour. The mixture was then extracted with methylene chloride. The extract was washed with an aqueous solution of sodium chloride, dried over anhydrous sodium sulfate, filtered and concentrated by evaporation under reduced pressure. The resulting residue was recrystallized from a mixture of ethyl acetate and hexane, to afford 8.21 g of the title compound as pale red needles, melting at 125°–127° C.

PREPARATION 11

Methyl 2-acetyl-6,7-dihydrothianaphthene-5-carboxylate

A solution of 2.0 g of methyl 6,7-dihydrothianaphthene-5-carboxylate (prepared as described in Preparation 9) in 30 ml of methylene chloride was added dropwise at −10° C. to a suspension of 2.75 g of aluminum chloride in 30 ml of methylene chloride. After 10 minutes, a solution of 1.10 ml of acetyl chloride in 10 ml of methylene chloride was added thereto over a period of 30 minutes. At the end of this time, the reaction mixture was treated as described in Preparation 10 from pouring into ice-water to concentration, and the residue obtained was subjected to silica gel column chromatography, using a 3:1 by volume mixture of hexane and ethyl acetate as the eluent. The product was then recrystallized from a mixture of ethyl acetate and hexane, to afford 2.25 g of the title compound as pale yellow needles, melting at 116°–118° C.

PREPARATION 12

Methyl 2-Benzoyl-6,7-dihydrothianaphthene-5-carboxylate

Using the same procedure as described in Preparation 11, 178 g of aluminum chloride, 1.17 ml of benzoyl chloride and 1.30 g of methyl 6,7-dihydrothianaphthene-5-carboxylate (prepared as described in Preparation 9) were reacted together. The reaction mixture was treated as described in Preparation 10 from pouring into ice-water to concentration, and the resulting residue was subjected to silica gel column chromatography, using a 4:1 by volume mixture of hexane and ethyl acetate as the eluent. The product was then recrystallized from a mixture of ethyl acetate and hexane, to afford 1.65 g of the title compound as colorless needles, melting at 99°–101° C.

PREPARATION 13

Methyl 6,7-dihydro-2-(2-methoxyvinyl)thianaphthene-5-carboxylate

A solution of 3.48 g of methyl 2-formyl-6,7-dihydrothianaphthene-5-carboxylate (prepared as described in Preparation 10) in 30 ml of tetrahydrofuran was added dropwise to an ethereal solution of an ylide prepared from 13.42 g of methoxymethyltriphenylphosphoridene chloride and 19.0 ml of a 15% w/v hexane solution of butyllithium under an atmosphere of nitrogen. At the end of this time, the reaction mixture was poured into ice-water, and extracted with diethyl ether. The extract was washed with an aqueous solution of sodium chloride and dried over anhydrous sodium sulfate, and the solvent was removed by evaporation under reduced pressure. The residue was subjected to silica gel column chromatography, using a mixture of hexane and ethyl acetate as the eluent, to afford 1.0 g of the title compound as an oily substance.

Nuclear Magnetic Resonance Spectrum (CDCl$_3$) δ ppm: 3.60 and 3.73 (6H, each singlet).

PREPARATION 14

2-(5-Methoxycarbonyl-6,7-dihydrothianaphthenyl)acetaldehyde

A solution of 1.0 g of methyl 6,7-dihydro-2-(2-methoxyvinyl)thianaphthene-5-carboxylate (prepared as described in Preparation 13) in a mixture of 30 ml of a 1% w/v hydrochloric acid and 60 ml of acetone was heated under reflux for 9 hours. The solvent was removed from the reaction mixture under reduced pressure. The residue was dissolved in ethyl acetate, and the resulting solution was washed in turn with a saturated aqueous solution of sodium bicarbonate and with a saturated aqueous solution of sodium chloride. It was then dried over anhydrous sodium sulfate, and the solvent was removed by evaporation under reduced pressure. The residue was subjected to silica gel column chromatography, using a 2:1 by volume mixture of hexane and ethyl acetate as the eluent, to afford 0.24 g of the title compound as an oily substance.

Nuclear Magnetic Resonance Spectrum (CDCl$_3$) δ ppm: 9.90 (1H).

PREPARATION 15

Methyl 6,7-dihydro-2-(2-hydroxyethyl)thianaphthene-5-carboxylate 42 mg of sodium borohydride were added to a solution of 0.24 g of 2-(5-methoxycarbonyl-6,7-dihydrothianaphthenyl)acetaldehyde (prepared as described in Preparation 14) in a mixture of 10 ml each of methanol and tetrahydrofuran. At the end of this time, the reaction mixture was concentrated by evaporation under reduced pressure. The residue was dissolved in ethyl acetate, and the resulting solution was washed with an aqueous solution of sodium chloride, dried over anhydrous sodium sulfate, filtered and then concentrated by evaporation under reduced pressure. The resulting residue was subjected to silica gel column chromatography, using a 3:2 by volume mixture of hexane and ethyl acetate as the eluent, to afford 0.17 g of the title compound as an oily substance.

Nuclear Magnetic Resonance Spectrum (CDCl₃) δ ppm: 3.80 (3H, singlet); 6.73 (1H, singlet); 7.45 (1H, singlet).

PREPARATION 16

Methyl 2-(2-methanesulfonyloxyethyl)-6,7-dihydrothianaphthene-5-carboxylate

A solution of 0.08 ml of methanesulfonyl chloride in 3 ml of diethyl ether was added to a solution of 0.17 g of methyl 6,7-dihydro-2-(2-hydroxyethyl)thianaphthene-5-carboxylate (prepared as described in Preparation 15) in a mixture of 5 ml of diethyl ether and 0.30 ml of triethylamine, and the mixture was stirred at room temperature for 30 minutes. At the end of this time, the reaction mixture was poured into ice-water, and the mixture was extracted with diethyl ether. The extract was washed in turn with a saturated aqueous solution of sodium bicarbonate and with an aqueous solution of sodium chloride. It was then dried over anhydrous sodium sulfate, filtered and concentrated by evaporation under reduced pressure. The resulting residue was subjected to silica gel column chromatography, using a 2:1 by volume mixture of hexane and ethyl acetate as the eluent, to afford 0.19 g of the title compound as an oily substance.

Nuclear Magnetic Resonance Spectrum (CDCl₃) δ ppm: 2.97 (3H, singlet); 3.78 (3H, singlet).

PREPARATION 17

4,5,6,7-Tetrahydro-4-keto-5-(methoxycarbonylmethyl)-thianaphthene

A solution of 9.57 g of 4,5,6,7-tetrahydro-4-keto-thianaphthene in 30 ml of dimethylformamide was added dropwise to a suspension of 3.29 g of sodium hydride (as a 55% w/w suspension in mineral oil) in 30 ml of dimethylformamide under an atmosphere of nitrogen. The mixture was cooled to 5° C., 16 ml of dimethyl carbonate was added thereto, and the mixture was stirred at room temperature for one hour. A solution of 6.6 ml of methyl bromoacetate in 10 ml of dimethylformamide was added dropwise thereto, and the mixture was stirred for one hour. At the end of this time, the reaction mixture was poured into ice-water and extracted with ethyl acetate. The extract was washed with a saturated aqueous solution of sodium chloride and dried over anhydrous sodium sulfate. The solvent was then removed by evaporation under reduced pressure. The residue was dissolved in a mixture of 200 ml each of concentrated aqueous hydrochloric acid and glacial acetic acid, and the solution was heated under reflux for 3 hours. The reaction mixture was then evaporated to dryness under reduced pressure, and the residue was dissolved in a mixture of 500 ml of methanol and 2 ml of concentrated sulfuric acid. The solution was heated under reflux for 2 hours. At the end of this time, the solvent was removed by evaporation under reduced pressure, and the residue was dissolved in ethyl acetate. The solution was washed in turn with water, with a saturated aqueous sodium bicarbonate and with a saturated aqueous solution of sodium chloride and dried over anhydrous sodium sulfate. The solvent was then removed by evaporation under reduced pressure. The residue was subjected to silica gel column chromatography, using a 2:1 by volume mixture of hexane and ethyl acetate as the eluent, to afford 10.13 g of the title compound as an oily substance.

Nuclear Magnetic Resonance Spectrum (CDCl₃) δ ppm: 3.72 (3H, singlet); 7.06 and 7.38 (each 1H, both doublets, J=6.0 Hz).

PREPARATION 18

4,5,6,7-Tetrahydro-5-(methoxycarbonylmethylidene)-thianaphthene 2.0 g of sodium borohydride was added to a solution of 10.13 g of 4,5,6,7-tetrahydro-4-keto-5-(methoxycarbonylmethyl)thianaphthene (prepared as described in Preparation 17) in 200 ml of methanol, and the mixture was stirred at room temperature for 30 minutes. At the end of this time, the reaction mixture was concentrated by evaporation under reduced pressure. The residue was dissolved in ethyl acetate, and the resulting solution was washed with an aqueous solution of sodium chloride, dried over anhydrous sodium sulfate filtered and then concentrated by evaporation under reduced pressure. The residue was dried thoroughly under reduced pressure and then acetylated with 20 ml of acetic anhydride in 40 ml of pyridine. At the end of this time, the reaction mixture was concentrated by evaporation under reduced pressure. The resulting residue was dissolved in ethyl acetate, and the solution was washed in turn with water, with a saturated aqueous solution of sodium bicarbonate and with a saturated aqueous solution of sodium chloride. It was then filtered and concentrated by evaporation under reduced pressure. The resulting residue was dissolved in 250 ml of toluene, and the solution was heated under reflux in the presence of 0.7 g of p-toluenesulfonic acid monohydrate for 30 minutes. At the end of this time, the reaction mixture was concentrated by evaporation under reduced pressure. The residue was dissolved in ethyl acetate, and the resulting solution was washed with an aqueous solution of sodium chloride, dried over anhydrous sodium sulfate, filtered and then concentrated by evaporation under reduced pressure. The resulting residue was subjected to silica gel column chromatography, using a 5:1 by volume mixture of hexane and ethyl acetate, to afford 5.50 g of the title compound as an oily substance.

Nuclear Magnetic Resonance Spectrum (CDCl₃) δ ppm: 3.17 (2H, singlet); 3.67 (3H, singlet); 6.31 (1H, singlet).

PREPARATION 19

2-Formyl-4,5,6,7-tetrahydro-5-(methoxycarbonylmethylidene)thianaphthene

Following the same procedure as described in Preparation 10, 1.50 g of the title compound was obtained as an oily substance from 2.50 g of 4,5,6,7-tetrahydro-5-(methoxycarbonylmethylidene)thianaphthene (prepared as described in Preparation 17).

Nuclear Magnetic Resonance Spectrum (CDCl₃) δ ppm: 3.70 (3H, singlet); 6.29 (1H, singlet); 7.40 (1H, singlet); 9.75 (1H, singlet).

PREPARATION 20

4,5,6,7-Tetrahydro-2-hydroxymethyl-5-(methoxycarbonylmethylidene)thianaphthene 0.26 g of sodium borohydride was added to a solution of 1.47 g of 2-formyl-4,5,6,7-tetrahydro-5-(methoxycarbonylmethylidene)thianaphthene (prepared as described in Preparation 19) in a mixture of 30 ml each of methanol and tetrahydrofuran. At the end of this time, the reaction mixture was concentrated by evaporation under reduced pressure. The residue was dissolved in ethyl acetate, and the resulting solution was washed with an aqueous solution of sodium chloride, dried over anhydrous sodium sulfate, filtered and then concentrated by evaporation under reduced pressure. The residue was subjected to silica gel column chromatography, using a 3:2 by volume mixture of hexane and ethyl acetate, to afford 1.24 g of the title compound as an oily substance.

Nuclear Magnetic Resonance Spectrum (CDCl$_3$) δ ppm: 3.69 (3H, singlet); 6.24 (1H, singlet); 6.67 (1H, singlet).

PREPARATION 21

Methyl 2-trimethylacetyl-6,7-dihydrothianaphthene-5-carboxylate

Using the same procedure as described in Preparation 11, 1.47 g of the title compound was obtained as an oily substance using 3.8 g of aluminum chloride, 3.0 g of methyl 6,7-dihydrothianaphthene-5-carboxylate (prepared as described in Preparation 9) and 2.7 ml of pivaloyl chloride.

Nuclear Magnetic Resonance Spectrum (CDCl$_3$) δ ppm: 1.40 (9H, singlet); 3.82 (3H, singlet); 7.62 (1H, singlet).

PREPARATION 22

Methyl 2-(2,2-dimethyl-1-hydroxyethyl)-6,7-dihydrothianaphthene-5-carboxylate

Using the same procedure as described in Preparation 15, 1.05 g of the title compound was obtained as an oily substance from 1.47 g of methyl 2-trimethylacetyl-6,7-dihydrothianaphthene-5-carboxylate (prepared as described in Preparation 14).

Nuclear Magnetic Resonance Spectrum (CDCl$_3$) δ ppm: 0.95 (9H, singlet); 3.75 (3H, singlet); 6.65 (1H, singlet).

PREPARATION 23 ;cl Methyl 2-cyclohexylcarbonyl-6,7-dihydrothianaphthene-5-carboxylate Using the same procedure as described in Preparation 11, 2.79 g of the title compound was obtained as an oily substance using 2.56 g of aluminum chloride, 2.0 g of methyl 6,7-dihydrothianaphthene-5-carboxylate (prepared as described in Preparation 9) and 1.93 ml of cyclohexanecarbonyl chloride.

Nuclear Magnetic Resonance Spectrum (CDCl$_3$) δ ppm: 3.83 (3H, singlet); 7.52 (1H, singlet); 7.58 (1H, singlet).

PREPARATION 24

Methyl 2-cyclohexylcarbonyl-5-methoxycarbonyl-4,5,6,7-tetrahydrothianaphthene-5-carboxylate 1.07 g of methyl 2-cyclohexylcarbonyl-6,7-dihydrothianaphthene-5-carboxylate (prepared as described in Preparation 23) in methanol was catalytically reduced over 1.0 g of 10% w/v palladium-on-carbon in the presence of catalytic amounts of acetic acid and in an atmosphere of hydrogen. The reaction mixture was then adjusted to a pH value of 8 by the addition of an aqueous solution of sodium bicarbonate. The resulting solution was filtered, and the filtrate was concentrated by evaporation under reduced pressure. The residue was dissolved in ethyl acetate, and the solution was dried over anhydrous sodium sulfate, filtered and concentrated by evaporation under reduced pressure, to afford 0.58 g of the title compound as an oily substance.

Nuclear Magnetic Resonance Spectrum (CDCl$_3$) δ ppm: 3.75 (1H, singlet); 7.43 (1H, singlet).

PREPARATION 25

Methyl 6,7-dihydro-2-[(cyclohexyl)(hydroxy)methyl]thianaphthene-5-carboxylate

Using the same procedure as described in Preparation 15, 1.42 g of the title compound was obtained as an oily substance from 1.72 g of methyl 2-cyclohexylcarbonyl-6,7-dihydrothianaphthene-5-carboxylate (prepared as described in Preparation 23).

PREPARATION 26

Methyl 4,5,6,7-tetrahydro-2-[(cyclohexyl)(hydroxy)methyl]-thianaphthene-5-carboxylate Using the same procedure described as in Preparation 24, 0.52 of the title compound was obtained as an oily substance from 0.58 g of methyl 6,7-dihydro-2-[(cyclohexyl)(hydroxy)methyl]thianaphthene-5-carboxylate (prepared as described in Preparation 25).

Nuclear Magnetic Resonance Spectrum (CDCl$_3$) δ ppm: 3.73 (3H, singlet); 6.60 (1H, singlet).

PREPARATION 27

5-Hydroxymethyl-4,5,6,7-tetrahydrothianaphthene

A solution of 3.20 g of methyl 4,5,6,7-tetrahydrothianaphthene-5-carboxylate in 35 ml of diethyl ether was added dropwise to a suspension of 0.62 g of lithium aluminum hydride in 30 ml of diethyl ether at below 10° C. After 10 minutes, sodium sulfate decahydrate was added thereto and the mixture was stirred. The reaction mixture was then filtered using a Celite 545 filter aid (Celite is a trade mark), the filtrate was concentrated by evaporation under reduced pressure, and the residue was subjected to silica gel column chromatography, using a 2:1 by volume mixture of hexane and ethyl acetate as the eluent, to afford 2.59 g of the title compound as an oily substance.

Nuclear Magnetic Resonance Spectrum (CDCl$_3$) δ ppm: 3.53 (2H, doublet);
6.68 and 7.00 (each 1H, both doublets, J=6.0 Hz).

PREPARATION 28

5-Methanesulfonyloxymethyl-4,5,6,7-tetrahydrothianaphthene

A solution of 1.00 ml of methanesulfonyl chloride in 10 ml of methylene chloride was added dropwise to a solution of 1.09 g of 5-hydroxymethyl-4,5,6,7-tetrahydrothianaphtene (prepared as described in Preparation 27) in a mixture of 30 ml of methylene chloride and 2.71 ml of triethylamine with ice-water, whilst cooling. The mixture was then stirred at room temperature for 1 hour. At the end of this time, the reaction mixture was poured into ice-water and extracted with methylene chloride. The extract was washed in turn with a saturated aqueous solution of sodium bicarbonate and with an aqueous solution of sodium chloride. It was then dried over anhydrous sodium sulfate, filtered and concentrated by evaporation under reduced pressure. The resulting residue was purified by column chromatography through silica gel, using a 3:1 by volume mixture of hexane and ethyl acetate as the eluent, to afford 1.38 g of the title compound as an oily substance.

Nuclear Magnetic Resonance Spectrum (CDCl$_3$) δ ppm: 2.98 (3H, singlet); 4.16 (2H, doublet, J=5.0 Hz); 6.72 and 7.05 (each 1H, both doublets, J=5.0 Hz).

PREPARATION 29

2-Formyl-5-methanesulfonyloxymethyl-4,5,6,7-tetrahydrothianaphthene

A solution of 1.18 g of 5-methanesulfonyloxymethyl-4,5,6,7-tetrahydrothianaphthene (prepared as described in Preparation 28) in 35 ml of methylene chloride was added dropwise to a suspension of 0.96 g of anhydrous aluminum chloride in 40 ml of methylene chloride at −30° C. under a nitrogen atmosphere. A solution of 0.54 ml of dichloromethyl methyl ether in 20 ml of methylene chloride was then added, and the mixture was thereafter stirred at 0° C. for 2 hours. At the end of this time, the reaction mixture was poured into ice-water, stirred for 1 hour and extracted with methylene chloride. The extract was washed with an aqueous solution of sodium chloride, dried over anhydrous sodium sulfate, filtered and concentrated by evaporation under reduced pressure. The resulting residue was purified by column chromatography through silica gel, using a 1:1 by volume mixture of hexane and ethyl acetate the as eluent, to afford 0.85 g of the title compound as an oily substance.

Nuclear Magnetic Resonance Spectrum (CDCl$_3$) δ ppm: 3.06 (3H, singlet); 4.24 (2H, doublet, J=5.0 Hz); 7.46 (1H, singlet); 9.85 (1H, singlet).

PREPARATION 30

Methyl 5-methanesulfonyloxymethyl-4,5,6,7-tetrahydrothianaphthene-2-carboxylate

A solution of 0.40 g of sodium chlorite in 5 ml of water was added dropwise to a solution of 0.80 g of 2-formyl-5-methanesulfonyloxymethyl-4,5,6,7-tetrahydrothianaphthene (prepared as described in Preparation 29) and 1.77 g of sulfamic acid in 48 ml of a 5:1 v/v mixture of dioxane and water at room temperature. When the dropwise addition was complete, the reaction mixture was concentrated by evaporation under reduced pressure. The residue was dissolved in ethyl acetate, and the solution was washed with an aqueous solution of sodium chloride, dried over anhydrous sodium sulfate and filtered. The filtrate was concentrated by evaporation under reduced pressure and the resulting crude residue was dissolved in 150 ml of methanol. This solution was heated for 7 hours under reflux in the presence of a catalytic amount of concentrated sulfuric acid. At the end of this time, the reaction mixture was concentrated by evaporation under reduced pressure, and the residue was dissolved in ethyl acetate. The resulting solution was washed in turn with water, with an aqueous solution of sodium bicarbonate and with an aqueous solution of sodium chloride. It was then dried over anhydrous sodium sulfate, filtered and concentrated by evaporation under reduced pressure. The resulting residue was subjected to column chromatography through silica gel, using a 3:2 by volume mixture of hexane and ethyl acetate as the eluent, to afford 0.78 g of the title compound as an oily substance.

Nuclear Magnetic Resonance Spectrum (CDCl$_3$) δ ppm:
3.03 (3H, singlet);
3.86 (3H, singlet);
4.22 (2H, doublet);
7.48 (1H, singlet).

PREPARATION 31

5-Hydroxymethyl-6,7-dihydrothianaphthene

Using the same procedure as described in Preparation 27, 1.65 g of the title compound was obtained as an oily substance from 2.07 g of methyl 6,7-dihydrothianaphthene-5-carboxylate.

Nuclear Magnetic Resonance Spectrum (CDCl$_3$) δ ppm: 4.19 (2H, doublet, J=6.0 Hz); 6.41 (1H, triplet, J=1.5 Hz); 6.81 and 7.03 (each 1H, both doublets, J=5.0 Hz).

PREPARATION 32

5-Methanesulfonyloxymethyl-6,7-dihydrothianaphthene

Using the same procedure as described in Preparation 28, 1.07 g of the title compound was obtained as an oily substance from 1.14 g of 5-hydroxymethyl-6,7-dihydrothianaphthene (prepared as described in Preparation 31).

Nuclear Magnetic Resonance Spectrum (CDCl$_3$) δ ppm: 3.02 (3H, singlet); 4.31 (2H, singlet); 6.45 (1H, triplet, J=1.5 Hz); 6.85 and 7.06 (each 1H, both doublets, J=5.0 Hz).

PREPARATION 33

2-Formyl-5-methanesulfonyloxymethyl-6,7-dihydrothianaphthene

Using the same procedure as described in Preparation 29, 0.82 g of the title compound was obtained as an oily substance from 0.99 g of 5-methanesulfonyloxymethyl-6,7-dihydrothianaphthene (prepared as described in Preparation 32).

Nuclear Magnetic Resonance Spectrum (CDCl$_3$) δ ppm: 3.07 (3H, singlet); 4.33 (2H, singlet); 6.46 (1H, triplet, J=1.5 Hz); 7.49 (1H, singlet); 9.89 (1H, singlet).

PREPARATION 34

Methyl 5-methanesulfonyloxymethyl-6,7-dihydrothianaphthene-2-carboxylate

Using the same procedure as described in Preparation 30, 0.69 g of the title compound was obtained as an oily substance from 0.75 g of 2-formyl-5-methanesulfonyloxymethyl-6,7-dihydrothianaphthene (prepared as described in Preparation 33).

Nuclear Magnetic Resonance Spectrum (CDCl$_3$) δ ppm: 3.02 (3H, singlet); 3.88 (3H, singlet); 4.30 (2H, singlet); 6.43 (1H, triplet, J=1.5 Hz); 7.50 (1H, singlet).

PREPARATION 35

6-Hydroxymethyl-4,5,6,7-tetrahydrothianaphthene

Using the same procedure as described in Preparation 27, 3.91 g of the title compound was obtained as an oily substance from 4.85 g of methyl 4,5,6,7-tetrahydrothianaphthene-6-carboxylate (prepared as described in Preparation 4).

Nuclear Magnetic Resonance Spectrum (CDCl$_3$) δ ppm: 3.57 (2H, doublet, J=6.0 Hz); 6.69 and 7.00 (each 1H, both doublets, J=5.0 Hz).

PREPARATION 36

6-Methanesulfonyloxymethyl-4,5,6,7-tetrahydrothianaphthene

Using the same procedure as described in Preparation 2, 4.28 g of the title compound was obtained as an oily substance from 3.50 g of 6-hydroxymethyl-4,5,6,7-tetrahydrothianaphthene (prepared as described in Preparation 35).

Nuclear Magnetic Resonance Spectrum (CDCl$_3$) δ ppm: 2.98 (3H, singlet); 4.17 (2H, doublet, J=6.0 Hz); 6.72 and 7.04 (each 1H, both doublets, J=5.0 Hz).

PREPARATION 37

2-Formyl-6-methanesulfonyloxymethyl-4,5,6,7-tetrahydrothianaphthene

Using the same procedure as described in Preparation 29, 2.92 g of the title compound was obtained as an oily substance from 4.11 g of 6-methanesulfonyloxymethyl-4,5,6,7-tetrahydrothianaphthene (prepared as described in Preparation 26).

Nuclear Magnetic Resonance Spectrum (CDCl$_3$) δ ppm: 3.05 (3H, singlet); 4.24 (2H, doublet, J=5.0 Hz); 7.46 (1H, singlet); 9.85 (1H, singlet).

PREPARATION 38

Methyl 6-methanesulfonyloxymethyl-4,5,6,7-tetrahydrothianaphthene-2-carboxylate

Using the same procedure as described in Preparation 30, 2.19 g of the title compound was obtained as colorless needles melting at 188°–191° C. from 2.32 g of 2-formyl-6-methanesulfonyloxymethyl-4,5,6,7-tetrahydrothianaphthene (prepared as described in Preparation 27).

Nuclear Magnetic Resonance Spectrum (CDCl$_3$) δ ppm: 3.05 (3H, singlet); 3.86 (3H, singlet); 4.20 (2H, doublet, J=5.0 Hz); 7.48 (1H, singlet).

PREPARATION 39

6-Hydroxymethyl-4,5-dihydrothianaphthene

Using the same procedure as described in Preparation 27, 1.19 g of the title compound was obtained as an oily substance from 1.64 g of methyl 4,5-dihydrothianaphthene-6-carboxylate.

Nuclear Magnetic Resonance Spectrum (CDCl$_3$) δ ppm: 4.22 (2H, doublet, J=6.0 Hz); 6.43 (1H, triplet, J=1.5 Hz); 6.71 and 7.02 (each 1H, both doublets, J=5.0 Hz).

PREPARATION 10

6-Methanesulfonyloxymethyl-4,5-dihydrothianaphthene

Using the same procedure as described in Preparation 28, 0.82 g of the title compound was obtained as an oily substance from 1.03 g of 6-hydroxymethyl-4,5-dihydrothianaphthene (prepared as described in Preparation 39).

Nuclear Magnetic Resonance Spectrum (CDCl$_3$) δ ppm: 3.01 (3H, singlet); 4.33 (2H, singlet); 6.48 (1H, triplet, J=1.5 Hz); 6.81 and 7.06 (each 1H, both doublets, J=5.0 Hz).

PREPARATION 41

2-Formyl-6-methanesulfonyloxymethyl-4,5-dihydrothianaphthene

Using the same procedure as described in Preparation 29, 0.49 g of the title compound was obtained as an oily substance from 0.73 g of 6-methanesulfonyloxymethyl-4,5-dihydrothianaphthene (prepared as described in Preparation 40).

Nuclear Magnetic Resonance Spectrum (CDCl$_3$) δ ppm: 3.05 (3H, singlet); 4.31 (1H, singlet); 6.47 (1H, triplet, J=1.5 Hz); 7.50 (1H, singlet); 9.88 (1H, singlet).

PREPARATION 42

Methyl 6-methanesulfonyloxymethyl-4,5-dihydrothianaphthene-2-carboxylate

Using the same procedure as described in Preparation 30, 0.39 g of the title compound was obtained as an oily substance from 0.40 g of 2-formyl-6-methanesulfonyloxymethyl-4,5-dihydrothianaphthene (prepared as described in Preparation 41).

Nuclear Magnetic Resonance Spectrum (CDCl$_3$) δ ppm: 3.02 (3H, singlet); 3.87 (3H, singlet); 4.29 (2H, singlet); 6.42 (1H, triplet, J=1.5 Hz); 7.49 (1H singlet).

PREPARATION 43

5-(2-Hydroxyethyl)-4,5,6,7-tetrahydrothianaphthene

Using the same procedure as described in Preparation 27, 3.75 g of the title compound was obtained as an oily substance from 4.50 g of 5-methoxycarbonylmethyl-4,5,6,7-tetrahydrothianaphthene.

Nuclear Magnetic Resonance Spectrum (CDCl$_3$) δ ppm: 3.85 (2H, quartet, J=6.5 Hz); 6.68 & 7.00 (each 1H, both doublets, J=6.0 Hz).

PREPARATION 44

5-(2-Methanesulfonyloxyethyl)-4,5,6,7-tetrahydrothianaphthene

Using the same procedure as described in Preparation 28, 3.72 g of the title compound was obtained as an oily substance from 3.68 g of 5-(2-hydroxyethyl)-4,5,6,7-tetrahydrothianaphthene (prepared as described in Preparation 43).

Nuclear Magnetic Resonance Spectrum (CDCl$_3$) δ ppm: 2.91 (3H, singlet); 4.25 (2H, triplet, J=6.0 Hz); 6.73 & 7.07 (each 1H, both doublets, J=5.0 Hz).

PREPARATION 45

5-(2-Methanesulfonyloxyethyl)-2-formyl-4,5,6,7-tetrahydrothianaphthene

Using the same procedure as described in Preparation 29, 2.29 g of the title compound was obtained as an oily substance from 3.51 g of 5-(2-methanesulfonyloxyethyl)-4,5,6,7-tetrahydrothianaphthene (prepared as described in Preparation 44).

Nuclear Magnetic Resonance Spectrum (CDCl$_3$) δ ppm: 3.06 (3H, singlet); 4.19 (2H, triplet, J=6.5 Hz); 7.44 (1H, singlet); 9.88 (1H, singlet).

PREPARATION 46

Methyl 5-(2-methanesulfonyloxyethyl)-4,5,6,7-tetrahydrothianaphthene-2-carboxylate Using the same procedure as described in Preparation 30, 1.93 g of the title compound was obtained as an oily substance from 2.13 g of 5-(2-methanesulfonyloxyethyl)-2-formyl-4,5,6,7-tetrahydrothianaphthene (prepared as described in Preparation 45).

Nuclear Magnetic Resonance Spectrum (CDCl$_3$) δ ppm: 3.04 (3H, singlet); 3.88 (3H, singlet); 4.19 (2H, triplet, J=6.5 Hz); 7.50 (1H, singlet).

EXPERIMENT 1

Inhibition of Thromboxane A$_2$ Synthetase

The platelet microsome fraction was separated from rabbit and from human blood by the method of Needleman et al. [Needleman et al., Science, 193, 163 (1976)].

The microsomal TXA$_2$ synthetase activity in the presence of various of the compounds of the invention at various concentrations was assayed by a modification of the method of Kayama et al. [Kayama et al., Prostaglandins, 21, 543 (1981)] by incubating the microsome fractions with labelled 1-[$^{14}$C] arachidonic acid at a concentration of 0.1 mM for 1 minute at 22° C., to a final volume of 0.2 ml. The reaction was terminated by the addition of 50 μM of 0.2M citric acid, and then the mixture was extracted with 1.5 ml of ethyl acetate. The extract was concentrated by evaporation under a stream of nitrogen gas and then subjected to silica gel thin layer chromatography. The developing solvent for the chromatography was a 90:8:1:0.8 by volume mixture of chloroform, methanol, acetic acid and water. The inhibitory activity of the compound tested was estimated by the decrease in the radioactivity of the TXB$_2$ fraction (TXA$_2$ is hydrolysed to the more stable TXB$_2$). The results are shown in the following Tables 1 and 2 as the IC$_{50}$, i.e. the concentration required to inhibit the activity of thromboxane synthetase by 50%.

In addition to the compounds of the invention, we also tested the activity of the known compound Dazoxiben, whose systematic name is 4-[2-(1-imidazolyl)ethoxy]benzoic acid hydrochloride, and which is disclosed in UK Patent Specification No. 2,038,821. The compounds of the invention employed are as follows:

Compound A=4,5,6,7-tetrahydro-2-(1-imidazolyl)methylthianaphthene-6-carboxylic acid hydrochloride (hydrochloride of Compound No. 1-1);

Compound B=sodium 4,5-dihydro-2-(1-imidazolyl)methylthianaphthene-6-carboxylate (sodium salt of Compound No. 2-1);

Compound C=4,5,6,7-tetrahydro-2-(1-imidazolyl)methylthianaphthene-5-carboxylic acid hydrochloride (hydrochloride of Compound No. 3-1).

The results using rabbits platelet microsomes are given in Table 1, whilst the results using human platelet microsomes are given in Table 2.

TABLE 1

| Test Compound | IC$_{50}$ ($\times 10^{-8}$ M) |
| --- | --- |
| A | 2.6 |
| B | 1.3 |
| C | 8.6 |
| Dazoxiben | 10.6 |

TABLE 2

| Test Compound | IC$_{50}$ ($\times 10^{-8}$ M) |
| --- | --- |
| A | 3.0 |
| B | 3.1 |
| Dazoxiben | 76 |

As can be seen from the results given above, the compounds of the invention show a significantly greater activity than does the known compound Dazoxiben and, in particular, as shown in Table 2, the activity of the compounds of the invention against thromboxane synthetase derived from human platelet microsomes is about 20 times higher than the activity of Dazoxiben.

EXPERIMENT 2

Antithrombotic Activity in Rabbits

This test was carried out by a modification of the method of Silver et al. [Science, 183, 1085 (1974)]. The test animals used were male Japanese white rabbits of approximately 3 kg body weight.

Each group of rabbits was administered orally the test compound at an appropriate dose and then, one hour after the oral administration, each was given 1.3 mg/kg of arachidonic acid by intravenous injection. The test animals were observed and sudden deaths during the test period were recorded. The ED$_{50}$ was determined by Probit's method.

Unmedicated rabbits were employed as a control, without administering any test compound, but these were all dead within several minutes after the injection of arachidonic acid, as a result of pulmonary thromboembolisms.

The results, in terms of the ED$_{50}$, are given in the following Table 3. In this Table, the compounds of the invention are identified as in Experiment 1.

TABLE 3

| Test Compound | ED$_{50}$ (mg/kg) |
| --- | --- |
| A | 0.27 |
| B | 0.12 |
| Dazoxiben | 1.1 |

The results given above indicate an activity about 5-10 times higher than that of the known compound Dazoxiben.

The results given above demonstrate that the compounds of the invention inhibit thromboxane synthetase of the blood platelet microsomes of mammals, including humans, and that they further exhibit strong and specific inhibitory activities against the biosynthesis of TXA$_2$. Specifically, the biosynthesis of TXA$_2$ may be inhibited to the extent of 50% by a concentration of the compound of the order of $10^{-8}$ molar. However, the compounds of the invention have very weak inhibitory activities against cyclooxygenase and against prostacyclin synthetase and thus do not inhibit the synthesis of other prostaglandin derivatives.

We claim:

1. A compound of formula (I):

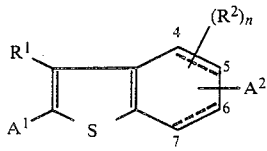

in which:

R[1] and R[2] are independently selected from the group consisting of hydrogen, $C_1$–$C_4$ alkyl, $C_6$–$C_{10}$ carbocyclic aryl and substituted $C_6$–$C_{10}$ carbocyclic aryl having one to three substituents selected from the group consisting of $C_1$–$C_4$ alkyl; $C_1$–$C_4$ alkoxy; $C_2$–$C_6$ straight or branched chain hydrocarbon carboxylic acyloxy; aromatic carboxylic acyloxy; $C_2$–$C_5$ straight or branched chain hydrocarbon carboxylic acylamino; aromatic carboxylic acylamino; trifluoromethyl; halogen; nitro; cyano; amino; $C_1$–$C_4$ alkylamino; dialkylamino in which each alkyl moiety is $C_1$–$C_4$; and carboxy, the aromtic moieties of said aromatic acyloxy and aromatic acylamino being $C_6$–$C_{10}$ carbocyclic aryl;

n is 1 or 2;

A[1] is a group of formula —Z—Y in which Y is a 1-imidazolyl or 2-, 3-, or 4-pyridyl; and Z is a methylene, ethylene, trimethylene or vinylene or a methylene, ethylene, trimethylene or vinylene having one or two substituents selected from the group consisting of $C_1$–$C_4$ alkyl; $C_3$–$C_6$ cycloalkyl; $C_6$–$C_{10}$ carbocyclic aryl; and substituted $C_6$–$C_{10}$ carbocyclic aryl having one to three substituents selected from the group consisting of $C_1$–$C_4$ alkyl, $C_1$–$C_4$ alkoxy and halogen;

A[2] is a group of formula —W—COOH, where W represents a direct bond, a methylene, a methine, an ethylene, a vinylene or substituted methine having one substituent or a substituted methylene, ethylene or vinylene group having one or two substituents, said substituents being selected from the group consisting of $C_1$–$C_4$ alkyl, $C_6$–$C_{10}$ carbocyclic aryl and substituted $C_6$–$C_{10}$ carbocyclic aryl having one to three substituents selected from the group consisting of $C_1$–$C_4$ alkyl, $C_1$–$C_4$ alkoxy and halogen; provided that, when W represents methine, single bonds are present both between the 4- and 5-positions and between the 6- and 7-positions;

A[2] is at the 5- or 6-position on the thianaphthene system;

each broken line represents a single or double carbon-carbon bond between the 4 and 5 or the 6 and 7 positions, provided that, when A[2] is at the 5-position, there is a single bond between the 6 and 7 positions, and that, when A[2] is at the 6-position, there is a single bond between the 4 and 5 positions; or a pharmaceutically acceptable salt, amide or ester thereof.

2. A compound as claimed in claim 1, having the formula (I$^{iii}$):

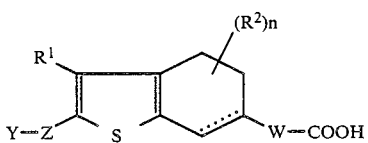

wherein R[1], R[2], W, Y, Z and n are as defined in claim 1 and the dotted line means a double or single bond between the 6- and 7-positions.

3. A compound as claimed in claim 1, having the formula (I$^{iv}$):

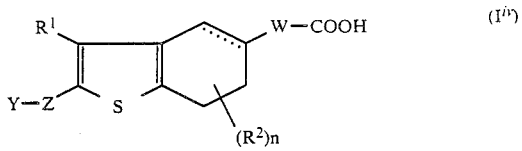

wherein R[1], R[2], W, Y, Z and n are as defined in claim 1 and the dotted line means a double or single bond between the 4- and 5-positions.

4. A compound as claimed in claim 1, in which:

A[1], A[2], Y and the broken lines are as defined in claim 1;

R[1] and R[2] are independently selected from the group consisting of hydrogen and $C_1$–$C_4$ alkyl;

n is 1;

Z represents a methylene, ethylene, trimethylene or vinylene group or a methylene, ethylene, trimethylene or vinylene group having one to three substituent selected from the group consisting of substitutents (b');

W represents a direct bond or a methylene, methine, ethylene or vinylene group; and substituents (b')

$C_1$–$C_4$ alkyl, cyclohexyl, phenyl and substituted phenyl having one to three substituent selected from the group consisting of $C_1$–$C_4$ alkyl, $C_1$–$C_4$ alkoxy and halogen atoms.

5. A compound as claimed in claim 2, in which:

Y and the dotted line are as defined in claim 2;

R[1] and R[2] are independently selected from the group consisting of hydrogen, methyl and ethyl groups;

n is 1;

Z represents a methylene or ethylene group or a methylene or ethylene group having one to three substituent selected from the group consisting of substituents (b");

W represents a direct bond; and substituents (b")

methyl, ethyl, phenyl and substituted phenyl having at least one substituent selected from the group consisting of methyl, ethyl, methoxy, ethoxy and halogen.

6. A compound as claimed in claim 3, in which :

Y and the dotted line are as defined in claim 3;

R[1] and R[2] are independently selected from the group consisting of hydrogen and $C_1$–$C_4$ alkyl;

n is 1;

Z represents a methylene, ethylene, trimethylene or vinylene group or a methylene, ethylene, trimethylene or vinylene group having one to three substituent selected from the group consisting of substituents (b');

W represents a direct bond or a methylen, methine, ethylene or vinylene group; and substituents (b')

$C_1$–$C_4$ alkyl, cyclohexyl, phenyl groups and substituted phenyl having one to three substituent selected from the group consisting of $C_1$–$C_4$ alkyl, $C_1$–$C_4$ alkoxy and halogen.

7. A compound as claimed in claim 6, in which:

Y and the dotted line are as defined in claim 6;

R¹ and R² are independently selected from the group consisting of hydrogen, methyl and ethyl;

n is 1;

Z represents a methylene or ethylene group or a methylene or ethylene group having one to three substituent selected from the group consisting of substituents (b″);

W represents a direct bond; and substituents (b″)

methyl, ethyl, phenyl and substituted phenyl having at least one substituent selected from the group consisting of methyl, ethyl, methoxy, ethoxy and halogen.

8. A compound as claimed in claim 1, which is selected from the group consisting of 4,5,6,7-tetrahydro-2-(1-imidazolyl)methylthianaphthene-6-carboxylic acid or a pharmaceutically acceptable salt, ester and amide thereof.

9. A compound as claimed in claim 1, which is selected from the group consisting of 4,5-dihydro-2-(1-imidazolyl)methylthianaphthene-6-carboxylic acid or a pharmaceutically acceptable salt, ester and amide thereof.

10. A compound as claimed in claim 1, which is selected from the group consisting of 4,5,6,7-tetrahydro-2-(1-imidazolyl)methyl-3-methylthianaphthene-6-carboxylic acid or an pharmaceutically acceptable salt, ester and amide thereof.

11. A compound as claimed in claim 1, which is selected from the group consisting of 4,5,6,7-tetrahydro-2-[2-(imidazol-1-yl)ethyl]thianaphthene-6-carboxylic acid or a pharmaceutically acceptable salt, ester and amide thereof.

12. A compound as claimed in claim 1, which is selected from the group consisting of 4,5,6,7-tetrahydro-2-(3-pyridyl)methylthianaphthene-6-carboxylic acid or a pharmaceutically acceptable salt, ester and amide thereof.

13. A compound as claimed in claim 1, which is selected from the group consisting of 4,5,6,7-tetrahydro-3-methyl-2-(3-pyridyl)methylthianaphthene-6-carboxylic acid or a pharmaceutically acceptable salt, ester and amide thereof.

14. A compound as claimed in claim 1, which is selected from the group consisting of 4,5,6,7-tetrahydro-2-[2-(3-pyridyl)ethyl]thianaphthene-6-carboxylic acid or a pharmaceutically acceptable salt, ester and amide thereof.

15. A compound as claimed in claim 1, which is selected from the group consisting of 4,5-dihydro-2-(1-imidazolyl)methyl-3-methylthianaphthene-6-carboxylic acid or a pharmaceutically acceptable salt, ester and amide thereof.

16. A compound as claimed in claim 1, which is selected from the group consisting of 4,5-dihydro-2-[α-(imidazol-1-yl)benzyl]thianaphthene-6-carboxylic acid or a pharmaceutically acceptable salt, ester and amide thereof.

17. A compound as claimed in claim 1, which is selected from the group consisting of 4,5-dihydro-2-[2-(imidazol-1-yl)ethyl]thianaphthene-6-carboxylic acid or a pharmaceutically acceptable salt, ester and amide thereof.

18. A compound as claimed in claim 1, which is selected from the group consisting of 4,5-dihydro-2-(3-pyridyl)methylthianaphthene-6-carboxylic acid or a pharmaceutically acceptable salt, ester and amide thereof.

19. A compound as claimed in claim 1, which is selected from the group consisting of 4,5,6,7-tetrahydro-2-(1-imidazolyl)methylthianaphthene-5-carboxylic acid or a pharmaceutically acceptable salt, ester and amide thereof.

20. A compound as claimed in claim 1, which is selected from the group consisting of 4,5,6,7-tetrahydro-2-(3-pyridyl)methylthianaphthene-5-carboxylic acid or a pharmaceutically acceptable salt, ester and amide thereof.

21. A compound as claimed in claim 1, which is selected from the group consisting of 6,7-dihydro-2-(1-imidazolyl)methylthianaphthene-5-carboxylic acid or a pharmaceutically acceptable salt, ester and amide thereof.

22. A compound as claimed in claim 1, which is selected from the group consisting of 6,7-dihydro-2-[α-(imidazol-1-yl)benzyl]thianaphthene-5-carboxylic acid or a pharmaceutically acceptable salt, ester and amide thereof.

23. A compound as claimed in claim 1, which is selected from the group consisting of 6,7-dihydro-2-[2-(imidazol-1-yl)ethyl]thianaphthene-5-carboxylic acid or a pharmaceutically acceptable salt, ester and amide thereof.

24. The compound as claimed in claim 8, which is 4,5,6,7-tetrahydro-2-(1-imidazolyl)methylthianaphthene-6-carboxylic acid hydrochloride.

25. The compound as claimed in claim 9, which is sodium 4,5-dihydro-2-(1-imidazolyl)methylthianaphthene-6-carboxylate.

26. The compound as claimed in claim 10, which is 4,5,6,7-tetrahydro-2-(1-imidazolyl)methyl-3-methylthianaphthene-6-carboxylic acid hydrochloride.

27. The compound as claimed in claim 11, which is 4,5,6,7-tetrahydro-2-(2-(imidazol-1-yl)ethyl)thianaphthene-6-carboxylic acid hydrochloride.

28. The compound as claimed in claim 12, which is 4,5,6,7-tetrahydro-2-(3-pyridyl)methylthianaphthene-6-carboxylic acid hydrochloride.

29. The compound as claimed in claim 13, which is 4,5,6,7-tetrahydro-3-methyl-2-(3-pyridyl)methylthianaphthene-6-carboxylic acid hydrochloride.

30. The compound as claimed in claim 14, which is 4,5,6,7-tetrahydro-2-(2-(3-pyridyl)ethyl)thianaphthene-6-carboxylic acid hydrochloride.

31. The compound as claimed in claim 15, which is sodium 4,5-dihydro-2-(1-imidazolyl)methyl-3-methylthianaphthene-6-carboxylate.

32. The compound as claimed in claim 16, which is sodium 4,5-dihydro-2-(α-(imidazol-1-yl)benzyl)-thianaphthene-6-carboxylate.

33. The compound as claimed in claim 17, which is sodium 4,5-dihydro-2-(2-(imidazol-1-yl)ethyl)thianaphthene-6-carboxylate.

34. The compound as claimed in claim 18, which is sodium 4,5-dihydro-2-(3-pyridyl)-methylthianaphthene-6-carboxylate.

35. A pharmaceutical composition comprising an effective amount to inhibit $TXA_2$ biosynthesis of the compound of claim 1 or its pharmaceutically acceptable salt, ester of amide, in a pharmaceutically acceptable carrier.

36. A composition as claimed in claim 35, wherein said compound has the formula ($I^{iii}$):

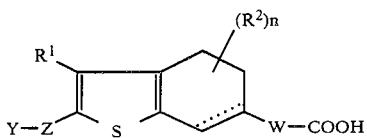

wherein $R^1$, $R^2$, W, Y, Z and n are as defined in claim 35 and the dotted line means a double or single bond between the 6- and 7- positions.

37. A composition as claimed in claim 35, wherein said compound has the formula ($I^{iv}$):

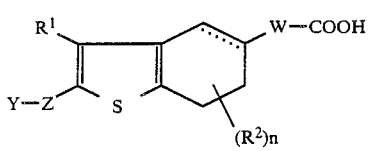

wherein $R^1$, $R^2$, W, Y, Z and n are as defined in claim 35 and the dotted line means a double or single bond between the 4- and 5- positions.

38. A composition as claimed in claim 35, in which:
$A^1$, $A^2$, Y and the broken and lines are as defined in claim 35;
$R^1$ and $R^2$ are independently selected from the group consisting of hydrogen and $C_1$–$C_4$ alkyl;
n is 1;
Z represents a methylene, ethylene, trimethylene or vinylene group or a methylene, ethylene, trimethylene or vinylene group having at least one substituent selected from the group consisting of substituents (b');
W represents a direct bond or a methylene, methine, ethylene or vinylene group; and
substituents (b')
$C_1$–$C_4$ alkyl, cyclohexyl, phenyl and substituted phenyl having at least one substituent selected from the group consisting of $C_1$–$C_4$ alkyl, $C_1$–$C_4$ alkoxy and halogen.

39. A composition as claimed in claim 36, in which:
Y and the dotted line are as defined in claim 36;
$R^1$ and $R^2$ are independently selected from the group consisting of hydrogen, methyl and ethyl;
n is 1;
Z represents a methylene or ethylene group or a methylene or ethylene group having one to three substituent selected from the group consisting of substituents (b'');
W represents a direct bond; and
substituents (b'')
methyl, ethyl, phenyl and substituted phenyl having one to three substituent selected from the group consisting of methyl, ethyl, methoxy, ethoxy and halogen.

40. A composition as claimed in claim 37, in which:
Y and the dotted line are as defined in claim 37;
$R^1$ and $R^2$ are independently selected from the group consisting of hydrogen and $C_1$–$C_4$ alkyl;
n is 1;
Z represents a methylene, ethylene, trimethylene or vinylene group or a methylene, ethylene, trimethylene or vinylene group having one to three substituent selected from the group consisting of substituents (b');

W represents a direct bond or a methylene, methine, ethylene or vinylene group; and
substituents (b')
$C_1$–$C_4$ alkyl, cyclohexyl, phenyl and substituted phenyl having one to three substituent selected from the group consisting of $C_1$–$C_4$ alkyl, $C_1$–$C_4$ alkoxy and halogen.

41. A composition as claimed in claim 40, in which:
Y and the dotted line are as defined in claim 40;
$R^1$ and $R^2$ are independently selected from the group consisting of hydrogen, methyl and ethyl;
n is 1;
Z represents a methylene or ethylene group or a methylene or ethylene group having one to three substituent selected from the group consisting of substituents (b'');
W represents a direct bond; and
substituents (b'')
methyl, ethyl, phenyl and substituted phenyl having one to three substituent selected from the group consisting of methyl, ethyl, methoxy, ethoxy and halogen.

42. A composition as claimed in claim 35, in which said compound is selected from the group consisting of:
4,5,6,7-tetrahydro-2-(1-imidazolyl)methylthianaphthene-6-carboxylic acid;
4,5-dihydro-2-(1-imidazolyl)methylthianaphthene-6-carboxylic acid;
4,5,6,7-tetrahydro-2-(1-imidazolyl)methyl-3-methyl-thianaphthene-6-carboxylic acid;
4,5,6,7-tetrahydro-2[2-(imidazol-1-yl)ethyl]thianaphthene-6-carboxylic acid;
4,5,6,7-tetrahydro-2-(3-pyridyl)methylthianaphthene-6-carboxylic acid;
4,5,6,7-tetrahydro-3-methyl-2-(3-pyridyl)methyl-thianaphthene-6-carboxylic acid;
4,5,6,7-tetrahydro-2-[2-(3-pyridyl)ethyl]thianaphthene-6-carboxylic acid;
4,5-dihydro-2-(1-imidazolyl)methyl-3-methylthianaphthene-6-carboxylic acid;
4,5-dihydro-2-[α-(imidazol-1-yl)benzyl]thianaphthene-6-carboxylic acid;
4,5-dihydro-2-[2-(imidazol-1-yl)ethyl]thianaphthene-6-carboxylic acid;
4,5-dihydro-2-(3-pyridyl)methylthianaphthene-6-carboxylic acid;
4,5,6,7-tetrahydro-2-(1-imidazolyl)methylthianaphthene-5-carboxylic acid;
4,5,6,7-tetrahydro-2-(3-pyridyl)methylthianaphthene-5-carboxylic acid;
6,7-dihydro-2-(1-imidazolyl)methylthianaphthene-5-carboxylic acid;
6,7-dihydro-2-[α-(imidazol-1-yl)benzyl]thianaphthene-5-carboxylic acid;
6,7-dihydro-2-[2-(imidazol-1-yl)ethyl]thianaphthene-5-carboxylic acid;
or a pharmaceutically acceptable salt, ester and amide thereof.

43. A method for the treatment of prophylaxis of thrombosis which comprises administering an effective amount of the compound of claim 1 or its pharmaceutically acceptable salt, ester or amide.

44. A method as claimed in claim 42, in which said compound is selected from the group consisting of:
4,5,6,7-tetrahydro-2-(1-imidazolyl)methylthianaphthene-6-carboxylic acid;
4,5-dihydro-2-(1-imidazolyl)methylthianaphthene-6-carboxylic acid;

4,5,6,7-tetrahydro-2-(1-imidazolyl)methyl-3-methyl-thianaphthene-6-carboxylic acid;

4,5,6,7-tetrahydro-2-[2-(imidazol-1-yl)ethyl]thianaphthene-6-carboxylic acid;

4,5,6,7-tetrahydro-2-(3-pyridyl)methylthianaphthene-6-carboxylic acid;

4,5,6,7-tetrahydro-3-methyl-2-(3-pyridyl)methyl-thianaphthene-6-carboxylic acid;

4,5,6,7-tetrahydro-2-[2-(3-pyridyl)ethyl]thianaphthene-6-carboxylic acid;

4,5-dihydro-2-(1-imidazolyl)methyl-3-methylthianaphthene-6-carboxylic acid;

4,5-dihydro-2-[α-(imidazol-1-yl)benzyl]thianaphthene-6-carboxylic acid;

4,5-dihydro-2-[2-(imidazol-1-yl)ethyl]thianaphthene-6-carboxylic acid;

4,5-dihydro-2-(3-pyridyl)methylthianaphthene-6-carboxylic acid;

4,5,6,7-tetrahydro-2-(1-imidazolyl)methylthianaphthene-5-carboxylic acid;

4,5,6,7-tetrahydro-2-(3-pyridyl)methylthianaphthene-5-carboxylic acid;

6,7-dihydro-2-(1-imidazolyl)methylthianaphthene-5-carboxylic acid;

6,7-dihydro-2-[α-(imidazol-1-yl)benzyl]thianaphthene-5-carboxylic acid;

6,7-dihydro-2-[2-(imidazol-1-yl)ethyl]thianaphthene-5-carboxylic acid;

or a pharmaceutically acceptable salt, ester and amide thereof.

* * * * *